(12) United States Patent
Weiss et al.

(10) Patent No.: US 7,166,277 B1
(45) Date of Patent: Jan. 23, 2007

(54) REMYELINATION OF NEURONS USING MULTIPOTENT NEURAL STEM CELL PROGENY

(75) Inventors: Samuel Weiss, Alberta (CA); Brent Reynolds, Alberta (CA); Joseph P. Hammang, Barrington, RI (US)

(73) Assignee: Neurospheres Holdings Ltd., Calgary (CA)

( * ) Notice: Subject to any disclaimer, the term of this patent is extended or adjusted under 35 U.S.C. 154(b) by 0 days.

(21) Appl. No.: 08/479,796

(22) Filed: Jun. 7, 1995

Related U.S. Application Data

(63) Continuation-in-part of application No. 08/270,412, filed on Jul. 5, 1994, now abandoned, which is a continuation of application No. 07/726,812, filed on Jul. 8, 1991, now abandoned, and a continuation-in-part of application No. 08/385,404, filed on Feb. 7, 1995, now abandoned, which is a continuation of application No. 07/961,813, filed on Oct. 16, 1992, now abandoned, which is a continuation-in-part of application No. 07/726,812, and a continuation-in-part of application No. 08/359,945, filed on Dec. 20, 1994, now abandoned, which is a continuation of application No. 08/221,655, filed on Apr. 1, 1994, now abandoned, which is a continuation of application No. 07/967,622, filed on Oct. 28, 1992, now abandoned, which is a continuation-in-part of application No. 07/726,812, and a continuation-in-part of application No. 08/376,062, filed on Jan. 20, 1995, now abandoned, which is a continuation of application No. 08/010,829, filed on Jan. 29, 1993, now abandoned, which is a continuation-in-part of application No. 07/726,812, and a continuation-in-part of application No. 08/149,508, filed on Nov. 9, 1993, now abandoned, which is a continuation-in-part of application No. 07/726,812, and a continuation-in-part of application No. 08/311,099, filed on Sep. 23, 1994, now abandoned, which is a continuation-in-part of application No. 07/726,812, and a continuation-in-part of application No. 08/338,730, filed on Nov. 14, 1994, now abandoned, which is a continuation-in-part of application No. 07/726,812.

(51) Int. Cl.
*A01N 63/00* (2006.01)
*A01N 65/00* (2006.01)
*C12N 5/00* (2006.01)
*C12N 5/02* (2006.01)

(52) U.S. Cl. .................... 424/93.1; 424/93.7; 435/377; 435/383; 435/384

(58) Field of Classification Search ............... 424/93.1, 424/570, 93.2, 93.21, 325, 368, 366; 435/172.3
See application file for complete search history.

(56) References Cited

U.S. PATENT DOCUMENTS

| | | | |
|---|---|---|---|
| 4,753,635 A | 6/1988 | Sagen et al. | 604/49 |
| 4,980,174 A | 12/1990 | Sagen et al. | 424/563 |
| 5,082,670 A * | 1/1992 | Gage | 424/520 |
| 5,175,103 A | 12/1992 | Lee et al. | 435/172.3 |
| 5,411,883 A | 5/1995 | Boss et al. | 435/240.2 |
| 5,612,211 A | 3/1997 | Wilson et al. | 435/378 |
| 5,753,506 A | 5/1998 | Johe | 435/240.23 |

FOREIGN PATENT DOCUMENTS

| | | |
|---|---|---|
| EP | 0 233 838 | 8/1987 |
| WO | 89/03872 | 5/1989 |
| WO | 90/06757 | 6/1990 |
| WO | 91/02003 | 2/1991 |
| WO | 91/09936 | 7/1991 |
| WO | 91/17242 | 11/1991 |
| WO | 93/01275 | 1/1993 |
| WO | 93/09802 | 5/1993 |
| WO | 94/03199 | 2/1994 |

OTHER PUBLICATIONS

Hunter et al. Dev. Biol. Des. 54(2): 235, 1990.*
Boyles et al. ABC 295(29): 17805, 1990.*
Masters et al Regulatory Peptides 33: 117, 1991.*
Morrison et al. Science 238: 72, 1987.*
Cattaneo et al. (Nature (LOND) 347 (6295). 1990).*
Renfranz et al. (Cell, 66 (4). 1991. 713-730).*
Blakemore et al. (Dev Neurosci 10 (1). 1988), Abstract only.*
Calof et al. (29th annual meeting American Society for Cell Biol. Nov. 5-9, 1989, J Cell Bio. 109 (4 part 2), 1989. 57A), Abstract only.*
Franklin et al. (81st meeting of the British Neuropathological Society, Jan. 10-11, 1991, Neuropathol Appl Neurobiol. 17 (3). 1991. 244), Abstract only.*

(Continued)

*Primary Examiner*—Anne-Marie Falk
(74) *Attorney, Agent, or Firm*—Mintz, Levin, Cohn, Ferris, Glovsky and Popeo, P.C.; Ivor R. Elrifi; Christina K. Stock

(57) ABSTRACT

The invention provides methods for producing myelin forming cells from multipotent self-renewing central nervous system neural stem cells as well as methods of using one or more cells from a multipotent self-renewing central nervous system neural stem cell population to form patches of myelin. Also provided are cell culture systems for forming patches of myelin and methods of treating demyelination diseases in a mammal.

43 Claims, 3 Drawing Sheets

OTHER PUBLICATIONS

Richardson et al. (Cell 53 (2). 1988. 309-320), Abstract only.*
Tohyama et al. (Lab Invest 66 (3). 1992, 303-313).*
Bossart et al. (Anticancer Res. 9 (6) 1989, 1496-1504), Abstract only.*
Jaenisch et al. (Acta Histochemica Supplementband, 42., 1992, 139-147).*
Akiyama et al. Transplantation of clonal neural precursor cells derived from adult human brain establishes functional peripheral myelin in the rat spinal cord pp. 27-39 2001.*
Mehler et al. (1999) Progenitor cell biology: Implications for neural regeneration. Arch. Neurol. 56: 780-784.*
Lo et al., "V-myc Immortalization of Early Rat Neural Crest Cells Yields a Clonal Cell Line which Generates Both Glial and Adrenergic Progenitor Cells," *Developmental Biology*, 145:139-153 (1991).
Almazan et al., "Epidermal Growth Factor and Bovine Growth Hormone Stimulate Differentiation and Myelination of Bran Cell Aggregates in Culture," *Developmental Brain Research*, 21:257-264 (1985).
Anchan et al., "Trophic Factors Influence Proliferation of Germinal Neuroepithelial Cells of the Retina," *J. Cell Biol.*, 109:58a, Abstract No. 308 (1989).
Anchan et al., "EGF and TGF-α Stimulate Retinal Neuroepithelial Cell Proliferation in Virto," *Neuron*, 6(6):923-936 (1991).
Bayer et al., "Neuron production in the Hippocampus and olfactory bulb of the adult rat Brain: addition or replacement?", *Annals NY. Acad. Sci.* 457:163-172 (1985).
BJörklund et al., "Neural Grafting in Animal Models of Neurodegenerative Diseases," *Ann. New York Acad. Sci.*, 457:53-81 (1985).
Bouvier et al., "Basic Fibroblast Growth Factor (bFGF) Promotes the Survival and Proliferation of Mesencephalic Neuronal Precursors in Vitro," *Society for Neuroscience Abstracts*, vol. 18, Abstract No. 403.7 (1992).
Boyles et al., "Accumulation of Apolipoproteins in the Regenerating and Remyelinating Mammalian Peripheral Nerve," *J. Biol. Chem.*, 265(29):17805-17815 (1990).
Calof et al., "Analysis of Neurogenesis in a Mammalian Neuroepithelium: Proliferation and Differentiation of an Olfactory Neuron Precursor in Vitro," *Neuron*, 3:115-127 (1989).
Cattaneo et al., "Identifying and manipulating neuronal stem cells," *TINS*, 14(8): 338-340 (1991).
Cattaneo et al., "Proliferation and differentiation of neuronal stem cells regulated by nerve growth factor," *Nature*, 347:762-765 (1990).
Cepko "Immortalization of neural cells via retrovirus-mediated oncogene transduction," *Ann. Rev. Neurosci.*, 12:47-65 (1989).
Deloulme et al., "Establishment of Pure Neuronal Cultures From Fetal Rat Spinal Cord and Proliferation of the Neuronal Precursor Cells in the Presence of Fibroblast Growth Factor," *Journal of Neuroscience Research*, 29:499-509 (1991).
Dunnett et al., "Dopamine-rich transplants in experimental Parkinsonism," *TINS*, 266-270 (Jul. 1983).
Emerich et al., "Behavioral Effects of Neural Transplantation," *Cell Transplantation*, 1:1-27 (1992).
Faaland et al., "Rapid uptake of tyrphostin into A431 human epidermoid cells is followed by delayed inhibition of epidermal growth factor (EGF)-stimulated EGF receptor tyrosine kinase activity", *Mol. Cell Biol.* 11(5):2697-2703 (1991).
Ferrari et al., "Basic Fibroblast Growth Factor Promotes the Survival and Development of Mesencephalic Neurons in Culture," *Developmental Biology*, 133:140-147 (1989).
Frederickson et al., "Immortal Neuroepithelial Precursor Cell Lines," *Society for Neuroscience Abstracts*, 13:182 Abstract No. 55.6 (1987).
Frederiksen et al., "Proliferation and differentiation of rat neuroepithelial precursor cells in vivo," *The Journal of Neuroscience* 8(4):1144-1151 (1988).
Frederiksen et al., "Immortalization of precursor cells from the mammalian CNS," *Neuron*, 1:439-448 (1988).

Freed et al., "Transplantation of human fetal dopamine cells for Parkinson's disease," *Arch. Neurol.*, 47:505-512 (1990).
Freshney, "Culture of Animal cells—A Manual of Basic Techniques", Alan R. Liss, Inc., N.Y. pp. 190-195.
Freshney, "Culture of Animal Cells—A Manual of Basic Techniques," Alan R. Liss, Inc., N.Y., Chapter 11, pp. 137-153 (1987).
Geller et al., "A defective HSV-1 vector expresses *Escherichia coli* β-galactosidase in cultured peripheral neurons," *Science*, 241:1667-1669 (1988).
Gensburger et al., "Brain basic fibroblast growth factor stimulates the proliferation of rat neuronal precursor cells in vitro," *FEBS Letts*, 217(1):1-5 (1987).
Godfraind et al., "In Vivo Analysis of Glial Cell Phenotypes during a Viral Demyelinating Disease in Mice," *Journal of Cell Biology*, 109(5):2405-2416.
Groves et al., "Repair of demyelinated lesions by transplantation of purified O-2A progenitor cells," *Nature*, 362:453 (1993).
Hall et al., "Stem cells: the generation and maintenance of cellular diversity," *Development*, 106:619-633 (1989).
Hoffman et al., "Transplantation of a polymer-encapsulated cell line genetically engineered to release NGF," *Exp. Neurol.* 122:100-106 (1993).
Hunter et al., "Growth factor responses of enriched bipotential glial progenitors," *Developmental Brain Research*, 54(2):235-248 (1990).
Hunter et al., "Growth factor responses of enriched bipotential glial progenitors," *Biol. Abstr.* 90:7, Abstract No. 78581 (1990).
Hurtig et al., "Postmortem analysis of adrenal-medulla-to-caudate autograft in a patient with Parkinson's disease," *Annals of Neurology*, 25(6):607-614 (1989).
Jiao et al., "Intracerebral transplants of primary muscle cells: a potential 'platform' for transgene expression in the brain," *Brain Research*, 575:143 (1992).
Kaplan, "Neurogenesis in the 3-month-old rat visual cortex," *J. Comp. Neurol.*, 195:323 (1981).
Kawaja et al., "Somatic gene transfer of nerve growth factor promotes the survival of axotomized septal neurons and the regeneration of their axons in adult rats," *J. Neurosci.*, 12(7):2849 (1992).
Korr et al., "Autoradiographic investigation of glial proliferation in the bran of adult mice," *J. Comp. Neurol.*, 150(2):169-176 (1973).
Lendahl et al., "CNS stem cells express a new class of intermediate filament protein," *Cell*, 60 585-595 (1990).
Lin et al., "GDNF: A Glial Line-Derived Neurotrophic Factor Midbrain Dopaminergic Neurons," *Science*, 260:1130 (1993).
Lindvall et al., "Grafts of fetal dopamine neurons survive and improve motor function in Parkinson's disease," *Science*, 247:574-577 (1990).
Lois et al., "Migration of neuroblasts from the lateral ventricle to the olfactory bulb in the adult mammalian CNS", *Society for Neuroscience Abstracts*, vol. 19, Abstract #361.6 (1993).
Luskin et al., Rate and pattern of migration of olfactory bulb interneurons generated postnatally in the subventricular zone, *Society for Neuroscience Abstracts*, vol. 19, Abstract #361.9 (1993).
Masters et al., "Insulin-like growth factor I (IGF-I) receptors and IGF-I action in oligodendrocytes from rat brains," *Regulatory Peptides*, 33(2):117-131 (1991).
Masters et al., "Insulin-like growth factor I (IGF-I) receptors and IGF-I action in oligodendrocytes from rat brains," *Biol. Abstr.* 93:3, Abstract No. 31828 (1992).
McKinnon et al., "FGF modulates the PDGF-driven pathway of oligodendrocyte development," *Neuron* 5:603-614 (1990).
Metcalf, "The hemopoietic regulators—an embarrassment of riches", *Bioassays* 14(12):799-805 (1992).
Morrison et al., "Trophic stimulation of cultured neurons from neonatal rat brain by epidermal growth factor," *Science*, 238:72-75 (1987).
Morshead et al., "Neural stem cells are located in the subependymal region of the adult mammalian forebrain", *Society for Neuroscience Abstracts*, vol. 19, Abstract #360.7 (1993).
Morshead et al., "Postmitotic Death is the Fate of Constitutively Proliferating Cells in the Subependymal Layer of the Adult Mouse Brain," *The Journal of Neuroscience*, 12(1):249-256 (1992).

Murphy et al., "Fibroblast growth factor stimulates the Proliferation and Differentiation of Neural Precursor Cells In Vitro," *Jour. of Neuroscience Research*, 25(4):463-475 (1990).

Mytilineou et al., "Epidermal Growth Factor-Induced Survival and Proliferation of Neuronal Precursor Cells from Embryonic Rat Mesencephalon," *Neuroscience Letters*, 135:62-66 (1992).

Nakafuku et al., "Epidermal growth factor and transforming growth factor-α can induce neuronal differentiation of rat pheochromocytoma PC12 cells under particular culture condition" *FEBS Letts*, 315(3):227-232 (1993).

Notter et al., "Neuronal properties of monkey adrenal medulla in vitro" *Cell Tissue Res.*, 244:69-76 (1986).

Pallage et al., "Long-term effects of nerve growth factor and neural transplants on behavior of rats with medial septal lesions," *Brain Research*, 386:197-208 (1986).

Palmer et al., "Genetically modified skin fibroblasts persist long after transplantation but gradually inactivate introduced genes" *Proc. Nat'l. Acad. Sci. USA*, 88:1330-1334 (1991).

Perlow et al., "Brain grafts reduce motor abnormalities produced by destruction of nigrostriatal dopamine system" *Science*, 204:643-646 (May, 1979).

Piszczkiewicz et al., "Proliferation and Survival of Rat Sensory Neuron Precursors in Vitro," *Society for Neuroscience Abstracts*, 19:1709 Abstract No. 704.7 (1993).

Potten et al., "Stem cells: attributes, cycles, spirals, pitfalls and uncertainties. Lessons for and from the Crypt," *Development*, 110:1001-1020 (1990).

Raff et al., "A glial progenitor cell that develops in vitro into an astrocyte or an oligodendrocyte depending on culture medium", *Nature* 303:390-396 (1983).

Rakic, "Limits of neurogenesis in primates," *Science* 227:1054 (1985).

Ramatowski et al., "Laminin enhances proliferation and migration of EGF-generated CNS stem cell progeny," Society for Neuroscience Abstracts, vol. 19, Abstract #360.10 (1993).

Reh et al., "Age of differentiation determines rat retinal germinal cell phenotype: Induction of differentiation by dissociation," *The Journal of Neuroscience*, 9 (12): 4179-4189 (1989).

Renfranz et al., "Region-specific differentiation of the hippocampal stem cell line HiB5 upon implantation into the developing mammalian brain" *Cell* 66:713-729 (1991).

Reynolds et al., "EGF-responsive stem cells in the mammalian central nervous system," *Neuronal Cell Death and Repair* Ch. 19, pp. 247 ed. Cuello (1993).

Reynolds et al., "A non-transformed, growth factor-dependent stem cell line derived from the embryonic mouse CNS produces neurons, astrocytes and oligodendrocytes," *Restorative Neurology and Neuroscience*, 4 (3) Abstract No. 34.P3 (1992).

Reynolds et al., "A multipoint EGF-responsive striatal embryonic progenitor cell produces neurons and astrocytes," *J. Neurosci.* 12(11):4565-4574 (1992).

Reynolds et al., "EGF- and TGFα- responsive striatal embryonic progenitor cells product both neurons and astrocytes" *Soc. Neurosc. Abstracts*, 16 Abstract No. 474.2 (Oct./Nov. 1990).

Reynolds et al., "Generation of neurons and astrocytes from isolated cells of the adult mammalian central nervous system," *Science*, 255:1707-1710 (1992).

Rohrer et al., "Proliferation and Differentiation of Neuronal Precursor Cells in the Chick Peripheral Nervous System," *Biol. Chem. Hoppe Seyles*, 368(10):1290-1296 (1987).

Ronnett et al., "Human cortical neuronal cell line: establishment from a patient with unilateral megalencephaly," *Science*, 248:603-605 (1990).

Rosenberg et al., "Grafting genetically modified cells to the damages brain: restorative effects of NGF expression," *Science*, 242:1575-1578 (1988).

Sensenbrenner et al., "Proliferation of Neuronal Precursor Cells from the Central Nervous System in Culture," *Reviews in the Neurosciences*, 5:43-53 (1994).

Smart, "The subependymal layer of the mouse brain and its cell production as shown by radioautography after Thymidine-$H^3$ injection", *J. Comp. Neurol.* 116:325 (1961).

Snyder et al., "Multipoint neural cell lines can engraft and participate in development of mouse cerebellum", *Cell* 68:33-51 (1992).

Soreto et al., in Neurochemistry: A Practical Approach, chapter 2, pp. 27-63 (1987).

Steinbusch et al., "Basic fibroblast growth factor enhances survival and sprouting of fetal dopaminergic cells implanted in the denervated reat caudate-putamen: preliminary observations," *Progress in Brain Research*, 82:81-86 (1990).

Temple "Division and differentiation of isolated CNS blast cells in microculture," *Nature*, 340:471-473 (1989).

Travis, "The search for liver stem cells picks up", *Science* 259:1829 (1993).

Van Der Maazen, et al., "Radiosensitivity of Glial Progenitor Cells of the Perinatal and Adult Rat Optic Nerve Studied by an In-vitro Clonogenic Assay", Biosis Abstract No. 91:324328, *Radiother. Oncol 20.* (1991).

Vescovi et al., "Continual proliferation of EGF-dependent progenitor cells of the embryonic human CNS in vitro", Society for Neuroscience Abstracts, vol. 19, Abstract #360.12 (1993).

Walsh et al., "Clonally related cortical cells show several migration patterns", *Science*, 241:1342 (1988).

Watts et al., "Adrenal-caudate transplantation in patients with Parkinson's disease (PD):—1-year follow-up," *Neurology* 39(Suppl.1) Abstract No. PP72 (1989).

Weiss et al., "Synaptogenesis of cultured striatal neurons in serum-free medium: a morphological and biochemical study,"0 *Proc. Natl. Acad. Sci. USA*, 83:2238-2242 (1986).

Williams "Programmed Cell Death: Apoptosis and Oncogenesis," *Cell*, 67:1097 (1991).

Williams et al., "Continuous infusion of nerve growth factor prevents basal forebrain neuronal death after fimbria fornix transection", *P.N.A.S.* 83:9231 (1986).

Widner et al., "Bilateral fetal mesencephalic grafting in two patients with parkinsonism induced by 1-methyl-4-phenyl-1,2,3,6-tetrahydropyridine (MPTP)", *New Eng. J. Med.* 327(22):1556 (1992).

Wolff et al., "Grafting Fibroblasts Genetically Modified to Produce L-dopa in a Rat Model of Parkinson Disease," *PNAS*, 86:9011-9014 (1989).

Wolswijk et al., "Identification of an adult-specific glial progenitor cell" *Development*, 105:387-400 (1989).

Yamada et al., *Growth of cells in hormonally defined media—Book A* Cold Spring Harbor Laboratory, 1982—Cold Spring Harbor conferences on cell proliferation, vol. 9, 131-143.

Nurcombe et al., "Developmental Regulation of Neural Response to FGF-1 and FGF-2 By Heparan Sulfate Proteoglycan," *Science*, 260:103-106 (1993).

Brickman et al., "Heparan Sulfates Mediate the Binding of Basic Fibroblast Growth Factor to a Specific Receptor on Neural Precursor Cells," *Journal of Biological Chemistry*, 270(42):24941-24948 (1995).

Blakemore et al., "Extensive Oligodendrocyte Remyelination Following Injection of Cultured Central Nervous System Cells into Demyelinating Lesions in Adult Central Nervous System," *Developmental Neuroscience*, 10:1-11 (1988).

Pezzoli et al., "Intraventricular Infusion of Epidermal Growth Factor Restores Dopaminergic Pathway in Hemiparkinsonian Rats," *Movement Disorders*, 6(4):281-287 (1991).

Stenevi et al., "Effects of Localized Intracerebral Injections of Nerve Growth Factor on the Regenerative Growth of Lesioned Central Noradrenergic Neurones," *Brian Research*, 69(2):217-234 (1974).

Palella et al., "Expression of Human HPRT mRNA in Brains of Mice Infected with a Recombinant Herpes Simplex Virus-1 Vector," *Gene*, 80:137-144 (1989).

Olson, "Grafts and Growth Factors in CNS: Basic Science with Clinical Promise," *Proceedings of the Xth Meeting of the World Society for Stereotactic and Functional Neurosurgery*, Macbashi: Japan. Oct. 1989, *Stereotact Funct. Neurosurg.*, 54-55:250-167 (1990).

Jackowski, "Neural Injury Repair: Hope for the Future as Barriers to Effective CNS Regeneration Become Clearer," *British Journal of Neurosurgery*, 9:303-317 (1995).

Lubetzki et al., "Gene Transfer of Rat Mature Oligodendrocytes and Glial Progenitor Cells with the LacZ Gene," *Ann. New York Acad. Sci.*, 605:66-70 (1990).

Friedmann, "Gene Therapy for Neurological Disorders," *TIG*, 10(6):210-214 (1994).

Orkin et al., "Report and Recommendations of the Panel to Assess the NIH Investment in Research on Gene," *NIH*, pp. 1-40 (Dec. 7, 1995).

Kumar et al., "Identification of a Set of Genes with Developmental Down-Regulated Expression in the Mouse Brain," *Biochemical and Biophysical Research Comm.*, 185(3):1155-1161 (1992).

Stratagene, 1991 Product Catalog, pp. 115-116.

Sambrook et al., "Molecular Cloning: A Laboratory Manual," 2nd ed., Cold Spring Harbor Press 12.2-12.10 (1989).

\* cited by examiner

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
        (A) LENGTH: 20 base pairs
        (B) TYPE: nucleic acid
        (C) STRANDEDNESS: unknown
        (D) TOPOLOGY: unknown (ii) MOLECULE TYPE: cDNA (xi) SEQUENCE DESCRIPTION: SEQ ID NO:1:

GAGATGCGAC CCTCAGGGAC                                                    20

(2) INFORMATION FOR SEQ ID NO:2:

(i) SEQUENCE CHARACTERISTICS:
        (A) LENGTH: 20 base pairs
        (B) TYPE: nucleic acid
        (C) STRANDEDNESS: unknown
        (D) TOPOLOGY: unknown (ii) MOLECULE TYPE: cDNA (xi) SEQUENCE DESCRIPTION: SEQ ID NO:2:

GTCCCTGAGG GTCGCATCTC                                                    20

(2) INFORMATION FOR SEQ ID NO:3:

(i) SEQUENCE CHARACTERISTICS:
        (A) LENGTH: 19 base pairs
        (B) TYPE: nucleic acid
        (C) STRANDEDNESS: unknown
        (D) TOPOLOGY: unknown (ii) MOLECULE TYPE: cDNA (xi) SEQUENCE DESCRIPTION: SEQ ID NO:3:

TAAATAAAAG ATGCCCTGG                                                     19

(2) INFORMATION FOR SEQ ID NO:4:

(i) SEQUENCE CHARACTERISTICS:
        (A) LENGTH: 19 base pairs
        (B) TYPE: nucleic acid
        (C) STRANDEDNESS: unknown
        (D) TOPOLOGY: unknown (ii) MOLECULE TYPE: cDNA (xi) SEQUENCE DESCRIPTION: SEQ ID NO:4:

CCAGGGCATC TTTTATTTA                                                     19

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: unknown
        (D) TOPOLOGY: unknown (ii) MOLECULE TYPE: cDNA (xi) SEQUENCE DESCRIPTION: SEQ ID NO:5:

```
                                    -continued
GAACTGGGAT GTGGGGCTGG                                                   20

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: unknown
        (D) TOPOLOGY: unknown (ii) MOLECULE TYPE: cDNA (xi) SEQUENCE DESCRIPTION: SEQ ID NO:6:

CCAGCCCCAC ATCCCAGTTC                                                   20

(2) INFORMATION FOR SEQ ID NO:7:

(i) SEQUENCE CHARACTERISTICS:
        (A) LENGTH: 18 base pairs
        (B) TYPE: nucleic acid
        (C) STRANDEDNESS: unknown
        (D) TOPOLOGY: unknown (ii) MOLECULE TYPE: cDNA (xi) SEQUENCE DESCRIPTION: SEQ ID NO:7:

GCCAGCGGCA TCACCTCG                                                     18

(2) INFORMATION FOR SEQ ID NO:8:

(i) SEQUENCE CHARACTERISTICS:
        (A) LENGTH: 18 base pairs
        (B) TYPE: nucleic acid
        (C) STRANDEDNESS: unknown
        (D) TOPOLOGY: unknown (ii) MOLECULE TYPE: cDNA (xi) SEQUENCE DESCRIPTION: SEQ ID NO:8:

CGAGGTGATG CCGCTGGC                                                     18
```

US 7,166,277 B1

REMYELINATION OF NEURONS USING MULTIPOTENT NEURAL STEM CELL PROGENY

CROSS-REFERENCE TO RELATED APPLICATIONS

This application is a continuation-in-part of U.S. Ser. No. 08/270,412, filed Jul. 5, 1994 now abandoned, which is a continuation of U.S. Ser. No. 07/726,812, filed Jul. 8, 1991 now abandoned; a continuation-in-part of U.S. Ser. No. 08/385,404, filed Feb. 7, 1995 now abandoned, which is a continuation of U.S. Ser. No. 07/961,813, filed Oct. 16, 1992 now abandoned, which is a continuation-in-part of U.S. Ser. No. 07/726,812, filed Jul. 8, 1991 now abandoned; a continuation-in-part of U.S. Ser. No. 08/359,945, filed Dec. 20, 1994 now abandoned, which is a continuation of U.S. Ser. No. 08/221,655, filed Apr. 1, 1994 now abandoned, which is a continuation of U.S. Ser. No. 07/967,622, filed Oct. 28, 1992, now abandoned which is a continuation-in-part of U.S. Ser. No. 07/726,812, filed Jul. 8, 1991 now abandoned; a continuation-in-part of U.S. Ser. No. 08/376,062, filed Jan. 20, 1995 now abandoned, which is a continuation of U.S. Ser. No. 08/010,829, filed Jan. 29, 1993 now abandoned, which is a continuation-in-part of U.S. Ser. No. 07/726,812, filed Jul. 8, 1991 now abandoned; a continuation-in-part of U.S. Ser. No. 08/149,508, filed Nov. 9, 1993 now abandoned, which is a continuation-in-part of U.S. Ser. No. 07/726,812, filed Jul. 8, 1991 now abandoned; a continuation-in-part of U.S. Ser. No. 08/311,099, filed Sep. 23, 1994 now abandoned, which is a continuation-in-part of U.S. Ser. No. 07/726,812, filed Jul. 8, 1991 now abandoned; and a continuation-in-part of U.S. Ser. No. 08/338,730, filed Nov. 14, 1994 now abandoned, which is a continuation-in-part of U.S. Ser. No. 07/726,812, filed Jul. 8, 1991 now abandoned.

FIELD OF THE INVENTION

This invention relates to a method for the in vitro culture and proliferation of multipotent neural stem cells, and to the use of these cells and their progeny as tissue grafts. In one aspect, this invention relates to a method for the isolation and in vitro perpetuation of large numbers of non-tumorigenic neural stem cell progeny which can be induced to differentiate and which can be used for neurotransplantation in the undifferentiated or differentiated state, into an animal to alleviate the symptoms of neurologic disease, neurodegeneration and central nervous system (CNS) trauma. In another aspect, this invention relates to a method of generating neural cells for the purposes of drug screening of putative therapeutic agents targeted at the nervous system. In another aspect, this invention also relates to a method of generating cells for autologous transplantation. In another aspect, the invention relates to a method for the in vivo proliferation and differentiation of the neural stem cell progeny in the host.

BACKGROUND OF THE INVENTION

The development of the mammalian central nervous system (CNS) begins in the early stage of fetal development and continues until the post-natal period. The mature mammalian CNS is composed of neuronal cells (neurons), and glial cells (astrocytes and oligodendrocytes).

The first step in neural development is cell birth, which is the precise temporal and spatial sequence in which stem cells and stem cell progeny (i.e daughter stem cells and progenitor cells) proliferate. Proliferating cells will give rise to neuroblasts, glioblasts and new stem cells.

The second step is a period of cell type differentiation and migration when undifferentiated progenitor cells differentiate into neuroblasts and gliolblasts which give rise to neurons and glial cells which migrate to their final positions. Cells which are derived from the neural tube give rise to neurons and glia of the CNS, while cells derived from the neural crest give rise to the cells of the peripheral nervous system (PNS). Certain factors present during development, such as nerve growth factor (NGF), promote the growth of neural cells. NGF is secreted by cells of the neural crest and stimulates the sprouting and growth of the neuronal axons.

The third step in development occurs when cells acquire specific phenotypic qualities, such as the expression of particular neurotransmitters. At this time, neurons also extend processes which synapse on their targets. Neurons are generated primarily during the fetal period, while oligodendrocytes and astrocytes are generated during the early post-natal period. By the late post-natal period, the CNS has its full complement of nerve cells.

The final step of CNS development is selective cell death, wherein the degeneration and death of specific cells, fibers and synaptic connections "fine-tune" the complex circuitry of the nervous system. This "fine-tuning" continues throughout the life of the host. Later in life, selective degeneration due to aging, infection and other unknown etiologies can lead to neurodegenerative diseases.

Unlike many other cells found in different tissues, the differentiated cells of the adult mammalian CNS have little or no ability to enter the mitotic cycle and generate new nerve cells. While it is believed that there is a limited and slow turnover of astrocytes (Korr et al., J. Comp. Neurol., 150:169, 1971) and that progenitors for oligodendrocytes (Wolsqijk and Noble, Development, 105:386, 1989) are present, the generation of new neurons does not normally occur.

Neuro genesis, the generation of new neurons, is complete early in the postnatal period. However, the synaptic connections involved in neural circuits are continuously altered throughout the life of the individual, due to synaptic plasticity and cell death. A few mammalian species (e.g. rats) exhibit the limited ability to generate new neurons in restricted adult brain regions such as the dentate gyrus and olfactory bulb (Kaplan, J. Comp. Neurol., 195:323, 1981; Bayer, N.Y. Acad. Sci., 457:163, 1985). However, this does not apply to all mammals; and the generation of new CNS cells in adult primates does not occur (Rakic, Science, 227:1054, 1985). This inability to produce new nerve cells in most mammals (and especially primates) may be advantageous for long-term memory retention; however, it is a distinct disadvantage when the need to replace lost neuronal cells arises due to injury or disease.

The low turnover of cells in the mammalian CNS together with the inability of the adult mammalian CNS to generate new neuronal cells in response to the loss of cells following injury or disease has led to the assumption that the adult mammalian CNS does not contain multipotent neural stem cells.

The critical identifying feature of a stem cell is its ability to exhibit self-renewal or to generate more of itself. The simplest definition of a stem cell would be a cell with the capacity for self-maintenance. A more stringent (but still simplistic) definition of a stem cell is provided by Potten and Loeffler (Development, 110:1001, 1990) who have defined stem cells as "undifferentiated cells capable of a) proliferation, b) self-maintenance, c) the production of a large number of differentiated functional progeny, d) regenerating the tissue after injury, and e) a flexibility in the use of these options."

The role of stem cells is to replace cells that are lost by natural cell death, injury or disease. The presence of stem cells in a particular type of tissue usually correlates with tissues that have a high turnover of cells. However, this correlation may not always hold as stem cells are thought to be present in tissues (e.g., liver [Travis, Science, 259:1829, 1993]) that do not have a high turnover of cells.

CNS disorders encompass numerous afflictions such as neurodegenerative diseases (e.g. Alzheimer's and Parkinson's), acute brain injury (e.g. stroke, head injury, cerebral palsy) and a large number of CNS dysfunctions (e.g. depression, epilepsy, and schizophrenia). In recent years neurodegenerative disease has become an important concern due to the expanding elderly population which is at greatest risk for these disorders. These diseases, which include Alzheimer's Disease, Multiple Sclerosis (MS), Huntington's Disease, Amyotrophic Lateral Sclerosis, and Parkinson's Disease, have been linked to the degeneration of neural cells in particular locations of the CNS, leading to the inability of these cells or the brain region to carry out their intended function.

In addition to neurodegenerative diseases, acute brain injuries often result in the loss of neural cells, the inappropriate functioning of the affected brain region, and subsequent behavior abnormalities. Probably the largest area of CNS dysfunction (with respect to the number of affected people) is not characterized by a loss of neural cells but rather by an abnormal functioning of existing neural cells. This may be due to inappropriate firing of neurons, or the abnormal synthesis, release, and processing of neurotransmitters. These dysfunctions may be the result of well studied and characterized disorders such as depression and epilepsy, or less understood disorders such as neurosis and psychosis.

Degeneration in a brain region known as the basal ganglia can lead to diseases with various cognitive and motor symptoms, depending on the exact location. The basal ganglia consists of many separate regions, including the striatum (which consists of the caudate and putamen), the globus pallidus, the substantia nigra, substantia innominate, ventral pallidum, nucleus basalis of Meynert, ventral tegmental area and the subthalamic nucleus.

In the case of Alzheimer's Disease, there is a profound cellular degeneration of the forebrain and cerebral cortex. In addition, upon closer inspection, a localized degeneration in an area of the basal ganglia, the nucleus basalis of Meynert, appears to be selectively degenerated. This nucleus normally sends cholinergic projections to the cerebral cortex which are thought to participate in cognitive functions including memory.

Many motor deficits are a result of degeneration in the basal ganglia. Huntington's Chorea is associated with the degeneration of neurons in the striatum, which leads to involuntary jerking movements in the host. Degeneration of a small region called the subthalamic nucleus is associated with violent flinging movements of the extremities in a condition called ballismus, while degeneration in the putamen and globus pallidus is associated with a condition of slow writhing movements or athetosis. In the case of Parkinson's Disease, degeneration is seen in another area of the basal ganglia, the substantia nigra par compacta. This area normally sends dopaminergic connections to the dorsal striatum which are important in regulating movement. Therapy for Parkinson's Disease has centered upon restoring dopaminergic activity to this circuit.

Other forms of neurological impairment can occur as a result of neural degeneration, such as amyotrophic lateral sclerosis and cerebral palsy, or as a result of CNS trauma, such as stroke and epilepsy.

Demyelination of central and peripheral neurons occurs in a number of pathologies and leads to improper signal conduction within the nervous systems. Myelin is a cellular sheath, formed by glial cells, that surrounds axons and axonal processes that enhances various electrochemical properties and provides trophic support to the neuron. Myelin is formed by Schwann cells in the PNS and by oligodendrocytes in the CNS. Among the various demyelinating diseases MS is the most notable.

To date, treatment for CNS disorder has been primarily via the administration of pharmaceutical compounds. Unfortunately, this type of treatment has been fraught with many complications including the limited ability to transport drugs across the blood-brain barrier and the drug-tolerance which is acquired by patients to whom these drugs are administered long-term. For instance, partial restoration of dopaminergic activity in Parkinson's patients has been achieved with levodopa, which is a dopamine precursor able to cross the blood-brain barrier. However, patients become tolerant to the effects of levodopa, and therefore, steadily increasing dosages are needed to maintain its effects. In addition, there are a number of side effects associated with levodopa such as increased and uncontrollable movement.

Recently, the concept of neurological tissue grafting has been applied to the treatment of neurological diseases such as Parkinson's Disease. Neural grafts may avert the need not only for constant drug administration, but also for complicated drug delivery systems which arise due to the blood-brain barrier. However, there are limitations to this technique as well. First, cells used for transplantation which carry cell surface molecules of a differentiated cell from another host can induce an immune reaction in the host. In addition, the cells must be at a stage of development where they are able to form normal neural connections with neighboring cells. For these reasons, initial studies on neurotransplantation centered on the use of fetal cells. Perlow, et al. describe the transplantation of fetal dopaminergic neurons into adult rats with chemically induced nigrostriatal lesions in "Brain grafts reduce motor abnormalities produced by destruction of nigrostriatal dopamine system," *Science* 204:643–647 (1979). These grafts showed good survival, axonal outgrowth and significantly reduced the motor abnormalities in the host animals.

In both human demyelinating diseases and rodent models there is substantial evidence that demyelinated neurons are capable of remyelination in vivo. In MS, for example, it appears that there are often cycles of de- and remyelination. Similar observations in rodent demyelinating paradigms lead to the prediction that exogenously applied cells would be capable of remyelinating demyelinated axons.

This approach has proven successful in a number of experimental conditions [Freidman et al., *Brain Research*, 378:142–146 (1986); Raine, et al., *Laboratory Investigation* 59:467–476 (1988); Duncan et al., *J. of Neurocytology*, 17:351–360 (1988)]. The sources of cells for some of these experiments included dissociated glial cell suspensions prepared from spinal cords (Duncan et al., supra), Schwann cell cultures prepared from sciatic nerve [Bunge et al., 1992, WO 92/03536; Blakemore and Crang, *J. Neurol. Sci.*, 70:207–223 (1985)]; cultures from dissociated brain tissue [Blakemore and Crang, *Dev. Neurosci.* 10:1–11 (1988)], oligodendrocyte precursor cells [Gumpel et al., *Dev. Neurosci.* 11:132–139 (1989)], O-2A cells [Wolswijk et al.,

*Development* 109:691–608 (1990); Raff et al., *Nature* 3030: 390–396 (1983); Hardy et al., *Development* 111:1061–1080 (1991)], and immortalized O-2A cell lines, [Almazan and McKay *Brain Res.* 579:234–245 (1992)].

O-2A cells are glial progenitor cells which give rise in vitro only to oligodendrocytes and type II astrocytes. Cells which appear by immunostaining in vivo to have the O-2A phenotype have been shown to successfully remyelinate demyelinated neurons in vivo, [Godfraind et al., *J. Cell Biol.* 109:2405–2416 (1989)]. Injection of a large number of O-2A cells is required to adequately remyelinate all targeted neurons in vivo, since it appears that O-2A cells (like other glial cell preparations) do not continue to divide in vivo. Although O-2A progenitor cells can be grown in culture, currently the only available isolation technique employs optic nerve as starting material. This is a low yield source, which requires a number of purification steps. There is an additional drawback that O-2A cells isolated by the available procedures are capable of only a limited number of divisions [Raff *Science* 243:1450–1455 (1989)].

Although adult CNS neurons are not good candidates for neurotransplantation, neurons from the adult PNS have been shown to survive transplantation, and to exert neurotrophic and gliotrophic effects on developing host neural tissue. One source of non-CNS neural tissue for transplantation is the adrenal medulla. Adrenal chromaffin cells originate from the neural crest like PNS neurons, and receive synapses and produce carrier and enzyme proteins similar to PNS neurons. Although these cells function in an endocrine manner in the intact adrenal medulla, in culture these cells lose their glandular phenotype and develop certain neural features in culture in the presence of certain growth factors and hormones [Notter, et al., "Neuronal properties of monkey adrenal medulla in vitro, *Cell Tissue Research* 244:69–76 (1986)]. When grafted into mammalian CNS, these cells survive and synthesize significant quantities of dopamine which can interact with dopamine receptors in neighboring areas of the CNS.

In U.S. Pat. No. 4,980,174, transplantation of monoamine-containing cells isolated from adult rat pineal gland and adrenal medulla into rat frontal cortex led to the alleviation of learned helplessness, a form of depression in the host. In U.S. Pat. No. 4,753,635, chromaffin cells and adrenal medullary tissue derived from steers were implanted into the brain stem or spinal cord of rats and produced analgesia when the implanted tissue or cell was induced to release nociceptor interacting substances (i.e. catecholamines such as dopamine). Adrenal medullary cells have been autologously grafted into humans, and have survived, leading to mild to moderate improvement in symptoms (Watts, et al., "Adrenal-caudate transplantation in patients with Parkinson's Disease (PD): 1-year follow-up," *Neurology* 39 Suppl 1: 127 [1989], Hurtig, et al., "Postmortem analysis of adrenal-medulla-to-caudate autograft in a patient with Parkinson's Disease," *Annals of Neurology* 25: 607–614 [1989]). However, adrenal cells do not obtain a normal neural phenotype, and are therefore probably of limited use for transplants where synaptic connections must be formed.

Another source of tissue for neurotransplantation is from cell lines. Cell lines are immortalized cells which are derived either by transformation of normal cells with an oncogene (Cepko, "Immortalization of neural cells via retrovirus-mediated oncogene transduction," *Ann. Rev. Neurosci.* 12:47–65 [1989]) or by the culturing of cells with altered growth characteristics in vitro (Ronnett, et al., "Human cortical neuronal cell line: Establishment from a patient with unilateral megalencephaly," *Science* 248:603–605 [1990]). Such cells can be grown in culture in large quantities to be used for multiple transplantations. Some cell lines have been shown to differentiate upon chemical treatment to express a variety of neuronal properties such as neurite formation, excitable membranes and synthesis of neurotransmitters and their receptors. Furthermore, upon differentiation, these cells appear to be amitotic, and therefore noncancerous. However, the potential for these cells to induce adverse immune responses, the use of retroviruses to immortalize cells, the potential for the reversion of these cells to an amitotic state, and the lack of response of these cells to normal growth-inhibiting signals make cell lines less than optimal for widespread use.

Another approach to neurotransplantation involves the use of genetically engineered cell types or gene therapy. Using this method, a foreign gene or transgene can be introduced into a cell which is deficient in a particular enzymatic activity, thereby allowing the cell to express the gene. Cells which now contain the transferred gene can be transplanted to the site of neurodegeneration, and provide products such as neurotransmitters and growth factors (Rosenberg, et al., "Grafting genetically modified cells to the damaged brain: Restorative effects of NGF Expression," *Science* 242:1575–1578, [1988]) which may function to alleviate some of the symptoms of degeneration. However, there still exists a risk of inducing an immune reaction using currently available cell lines. In addition, these cells may also not achieve normal neuronal connections with the host tissue.

Genetically modified cells have been used in neurological tissue grafting in order to replace lost cells which normally produce a neurotransmitter. For example, fibroblasts have been genetically modified with a retroviral vector containing a cDNA for tyrosine hydroxylase, which allows them to produce dopamine, and implanted into animal models of Parkinson's Disease (Gage et al., U.S. Pat. No. 5,082,670).

While the use of genetically modified fibroblasts to treat CNS disorders has shown promise in improving some behavioral deficits in animal models of Parkinson's Disease, and represents a novel approach to supplying a needed transmitter to the CNS, it suffers from several significant drawbacks as a treatment for Parkinson's Disease and in general as a therapeutic approach for treating neurodegenerative diseases and brain injury. First, the CNS is primarily composed of three cell types neurons, astrocytes and oligodendrocytes. The implantation of a foreign cell such as a fibroblast into the CNS and its direct and indirect effects on the functioning of the host cells has yet to be studied. However, it is likely that the expression of membrane bound factors and the release of soluble molecules such as growth factors and proteases will alter the normal behavior of the surrounding tissue. This may result in the disruption of neuronal firing patterns either by a direct action on neurons or by an alteration in the normal functioning of glial cells.

Another concern that arises when fibroblasts are implanted into the CNS is the possibility that the implanted cells may lead to tumor formation because the intrinsic inhibition of fibroblast division is poorly controlled. Instead, extrinsic signals play a major role in controlling the number of divisions the cell will undergo. The effect of the CNS environment on the division of implanted fibroblasts and the high probability of a fibroblastic tumor formation has not been studied in the long-term.

A third concern in transplanting fibroblasts into the CNS is that fibroblasts are unable to integrate with the CNS cells as astrocytes, oligodendrocytes, or neurons do. Fibroblasts are intrinsically limited in their ability to extend neuronal-like processes and form synapses with host tissue. Hence, although the genetic modification and implantation of fibroblasts into the CNS represents an improvement over the current technology for the delivery of certain molecules to the CNS, the inability of fibroblasts to integrate and function as CNS tissue, their potential negative effects on CNS cells, and their limited intrinsic control of proliferation limits their practical usage for implantation for the treatment of acute or chronic CNS injury or disease.

A preferred tissue for genetic modification and implantation would be CNS cells—neurons, astrocytes, or oligodendrocytes. One source of CNS cells is from human fetal tissue. Several studies have shown improvements in patients with Parkinson's Disease after receiving implants of fetal CNS tissue. Implants of embryonic mesencephalic tissue containing dopamine cells into the caudate and putamen of human patients was shown by Freed et al. (*N Engl J Med* 327:1549–1555 (1992)) to offer long-term clinical benefit to some patients with advanced Parkinson's Disease. Similar success was shown by Spencer et al. (*N Engl J Med* 327:1541–1548 (1992)). Widner et al. (*N Engl J Med* 327:1556–1563 (1992)) have shown long-term functional improvements in patients with MPTP-induced Parkinsonism that received bilateral implantation of fetal mesencephalic tissue.

While the studies noted above are encouraging, the use of large quantities of aborted fetal tissue for the treatment of disease raises ethical considerations and political obstacles. There are other considerations as well. Fetal CNS tissue is composed of more than one cell type, and thus is not a well-defined source of tissue. In addition, there are serious doubts as to whether an adequate and constant supply of fetal tissue would be available for transplantation. For example, in the treatment of MPTP-induced Parkinsonism (Widner supra) tissue from 6 to 8 fetuses were used for implantation into the brain of a single patient. There is also the added problem of the potential for contamination during fetal tissue preparation. Moreover, the tissue may already be infected with a bacteria or virus, thus requiring expensive diagnostic testing for each fetus used. However, even diagnostic testing might not uncover all infected tissue. For example, the diagnosis of HIV-free tissue is not guaranteed because antibodies to the virus are generally not present until several weeks after infection.

While currently available transplantation approaches represent a significant improvement over other available treatments for neurological disorders, they suffer from significant drawbacks. The inability in the prior art of the transplant to fully integrate into the host tissue, and the lack of availability of cells in unlimited amounts from a reliable source for grafting are, perhaps, the greatest limitations of neurotransplantation.

It would be more preferable to have a well-defined, reproducible source of neural tissue for transplantation that is available in unlimited amounts. Since adult neural tissue undergoes minimal division, it does not readily meet these criteria. While astrocytes retain the ability to divide and are probably amenable to infection with foreign genes, their ability to form synapses with neuronal cells is limited and consequently so is their extrinsic regulation of the expression and release of the foreign gene product.

Oligodendrocytes suffer from some of the same problems. In addition, mature oligodendrocytes do not divide, limiting the infection of oligodendrocytes to their progenitor cells (e.g. O2A cells). However, due to the limited proliferative ability of oligodendrocyte progenitors, the infection and harvesting of these cells does not represent a practical source.

The infection of neurons with foreign genes and implantation into the CNS would be ideal due to their ability to extend processes, make synapses and be regulated by the environment. However, differentiated neurons do not divide and transfection with foreign genes by chemical and physical means is not efficient, nor are they stable for long periods of time. The infection of primary neuronal precursors with retroviral vectors in vitro is not practical either because neuroblasts are intrinsically controlled to undergo a limited number of divisions making the selection of a large number of neurons, that incorporate and express the foreign gene, nearly impossible. The possibility of immortalizing the neuronal precursors by retroviral transfer of oncogenes and their subsequent infection of a desired gene is not preferred due to the potential for tumor formation by the implanted cells.

In addition to the need for a well-defined, reproducible source of neural cells available in unlimited amounts for transplantation purposes, a similar need exists for drug screening purposes and for the study of CNS function, dysfunction, and development. The mature human nervous system is composed of billions of cells that are generated during development from a small number of precursors located in the neural tube. Due to the complexity of the mammalian CNS, the study of CNS developmental pathways, as well as alterations that occur in adult mammalian CNS due to dysfunction, has been difficult. Such areas would be better studied using relatively simple models of the CNS under defined conditions.

Generally, two approaches have been taken for studying cultured CNS cells: the use of primary neural cultures; and the use of neural cell lines. Primary mammalian neural cultures can be generated from nearly all brain regions providing that the starting material is obtained from fetal or early post-natal animals. In general, three types of cultures can be produced, enriched either in neurons, astrocytes, or oligodendrocytes. Primary CNS cultures have proven valuable for discovering many mechanisms of neural function and are used for studying the effects of exogenous agents on developing and mature cells. While primary CNS cultures have many advantages, they suffer from two primary drawbacks. First, due to the limited proliferative ability of primary neural cells, new cultures must be generated from several different animals. While great care is usually taken to obtain tissue at identical states of development and from identical brain regions, it is virtually impossible to generate primary cultures that are identical. Hence, there exists a significant degree of variability from culture to culture.

A second disadvantage of primary cultures is that the tissue must be obtained from fetuses or early post-natal animals. If primary cultures are to be performed on a regular basis, this requires the availability of a large source of starting material. While this is generally not a problem for generating primary cultures from some species (e.g. rodents), it is for others (e.g. primates). Due to the limited supply and ethical concerns, the culturing of primary cells from primates (both human and non-human) is not practical.

Due to the limited proliferative ability of primary neural cells, the generation of a large number of homogenous cells for studies of neural function, dysfunction, and drug design/screening has previously not been achieved. Therefore, homogenous populations of cells that can generate a large number of progeny for the in vitro investigation of CNS function has been studied by the use of cell lines. The generation of neural cell lines can be divided into two categories: 1) spontaneously occurring tumors, and 2) custom-designed cell lines.

Of the spontaneously occurring tumors, probably the most studied cell line for neurobiology is the rat pheochromocytoma (PC12) cells that can differentiate into sympathetic-like neurons in response to NGF. These cells have proven to be a useful model for studying mechanisms of neural development and alterations (molecular and cellular) in response to growth factors. Neuroblastoma and glioma cell lines have been used to study neuronal and glial functioning [Liles, et al., *J. Neurosci.* 7, 2556–2563 (1987); Nister et al. *Cancer Res.* 48(14) 3910 (1988)]. Embryonal carcinoma cells are derived from teratoma tumors of fetal germ cells and have the ability to differentiate into a large number of non-neural cell types with some lines (e.g. P19 cells) [Jones-Villeneuve et al. *J. Cell Biol.* 94, 253–262 (1982)] having the ability to differentiate into neural cells [(McBurney et al. *J. Neurosci.* 8(3) 1063–73 (1993)]. A human teratocarcinoma-derived cell line, NTera 2/cl.D1, with a phenotype resembling CNS neuronal precursor cells, can be induced to differentiate in the presence of retinoic acid. However, the differentiated cells are restricted to a neuronal phenotype [Pleasure and Lee *J. Neurosci. Res.* 35: 585–602 (1993)]. While these types of cell lines are able to generate a large number of cells for screening the effects of exogenous agents on cell survival or function, the limited number of these types of lines, the limited number of phenotypes that they are able to generate and the unknown nature of their immortalization (which may effect the function of the cells in an undefined manner) makes these types of cell lines less than ideal for in vitro models of neural function and discovery of novel therapeutics.

An alternative approach to spontaneously occurring cell lines is the intentional immortalization of a primary cell by introducing an oncogene that alters the genetic make-up of the cell thereby inducing the cell to proliferate indefinitely. This approach has been used by many groups to generate a number of interesting neural cell lines [(Bartlett et al. *Proc. Nat. Acad. Sci.* 85(9) 3255–3259 (1988); Frederiksen et al. *Neuron* 1, 439–448 (1988); Trotter et al. *Oncogene* 4: 457–464 (1989); Ryder et al. *J. Neurobiol.* 21: 356–375 (1980); Murphy et al. *J. Neurobiol* 22: 522–535 (1991); Almazan and McKay et al. *Brain Res.* 579: 234–245 (1992)]. While these lines may prove useful for studying the decisions that occur during cell determination and differentiation, and for testing the effects of exogenous agents, they suffer from several drawbacks. First, the addition of an oncogene that alters the proliferative status of a cell may affect other properties of the cell (oncogenes may play other roles in cells besides regulating the cell cycle). This is well illustrated in a study by Almazan and McKay, supra, and their immortalization of an oligodendrocyte precursor from the optic nerve which is unable to differentiate into type II astrocytes (something that normal optic nerve oligodendrocyte precursors can do). The authors suggest the presence of the immortalizing antigen may alter the cells ability to differentiate into astrocytes.

Another drawback to using intentionally immortalized cells results from the fact that the nervous system is composed of billions of cells and possibly thousands of different cell types, each with unique patterns of gene expression and responsiveness to their environment. A custom-designed cell line is the result of the immortalization of a single progenitor cell and its clonal expansion. While a large supply of one neural cell type can be generated, this approach does not take into account cellular interactions between different cell types. In addition, while it is possible to immortalize cells from a given brain region, immortalization of a desired cell is not possible due to the lack of control over which cells will be altered by the oncogene. Hence, while custom designed cell lines offer a few advantages over spontaneously occurring tumors, they suffer from several drawbacks and are less than ideal for understanding CNS function and dysfunction.

Therefore, in view of the aforementioned deficiencies attendant with prior art methods of neural cell culturing, transplantation, and CNS models, a need exists in the art for a reliable source of unlimited numbers of undifferentiated neural cells for neurotransplantation and drug screening which are capable of differentiating into neurons, astrocytes, and oligodendrocytes. Preferably cellular division in such cells from such a source would be epigenetically regulated and a suitable number of cells could be efficiently prepared in sufficient numbers for transplantation. The cells should be suitable in autografts, xenografts, and allografts without a concern for tumor formation. There exists a need for the isolation, perpetuation and transplantation of autologous neural cells from the juvenile or adult brain that are capable of differentiating into neurons and glia.

A need also exists for neural cells, capable of differentiating into neurons, astrocytes and oligodendrocytes that are capable of proliferation in vitro and thus amenable to genetic modification techniques.

Additionally, there exists a need for the repair of damaged neural tissue in a relatively non-invasive fashion, that is by inducing neural cells to proliferate and differentiate into neurons, astrocytes, and oligodendrocytes in vivo, thereby averting the need for transplantation.

Accordingly, a major object of the present invention is to provide a reliable source of an unlimited number of neural cells for neurotransplantation that are capable of differentiating into neurons, astrocytes, and oligodendrocytes.

It is another object of the present invention to provide a method for the in vitro proliferation of neural stem cells from embryonic, juvenile and adult brain tissue, to produce unlimited numbers of precursor cells available for transplantation that are capable of differentiating into neurons, astrocytes, and oligodendrocytes.

A further object of the invention is to provide methods for inducing neural cells to proliferate and differentiate in vivo, thereby averting the need for neurotransplantation.

A still further object of the invention is to provide a method of generating large numbers of normal neural cells for the purpose of screening putative therapeutic agents targeted at the nervous system and for models of CNS development, function, and dysfunction.

SUMMARY OF THE INVENTION

This invention provides in one aspect a composition for inducing the proliferation of a multipotent neural stem cell comprising a culture medium supplemented with at least one growth factor, preferably epidermal growth factor or transforming growth factor alpha.

The invention also provides a method for the in vitro proliferation and differentiation of neural stem cells and stem cell progeny comprising the steps of (a) isolating the cell from a mammal, (b) exposing the cell to a culture medium containing a growth factor, (c) inducing the cell to proliferate, and (d) inducing the cell to differentiate. Proliferation and perpetuation of the neural stem cell progeny can be carried out either in suspension cultures, or by allowing cells to adhere to a fixed substrate. Proliferation and differentiation can be done before or after transplantation, and in various combinations of in vitro or in vivo conditions, including (1) proliferation and differentiation in vitro, then transplantation, (2) proliferation in vitro, transplantation, then further proliferation and differentiation in vivo, and (3) proliferation in vitro, transplantation and differentiation in vivo.

The invention also provides for the proliferation and differentiation of the progenitor cells in vivo, which can be done directly in the host without the need for transplantation.

The invention also provides a method for the in vivo transplantation of neural stem cell progeny, treated as in any of (1) through (3) above, which comprises implanting, into a mammal, these cells which have been treated with at least one growth factor.

Furthermore, the invention provides a method for treating neurodegenerative diseases comprising administering to a mammal neural stem cell progeny which have been treated as in any of (1) through (3), and induced to differentiate into neurons and/or glia.

The invention also provides a method for treating neurodegenerative disease comprising stimulating in vivo mammalian CNS neural stem cells to proliferate and the neural stem cell progeny to differentiate into neurons and/or glia.

The invention also provides a method for the transfection of neural stem cells and stem cell progeny with vectors which can express the gene products for growth factors, growth factor receptors, and peptide neurotransmitters, or express enzymes which are involved in the synthesis of neurotransmitters, including those for amino acids, biogenic amines and neuropeptides, and for the transplantation of these transfected cells into regions of neurodegeneration.

In a still further aspect, the invention provides a method for the screening of potential neurologically therapeutic pharmaceuticals using neural stem cell progeny which have been proliferated in vitro.

Figure 1:
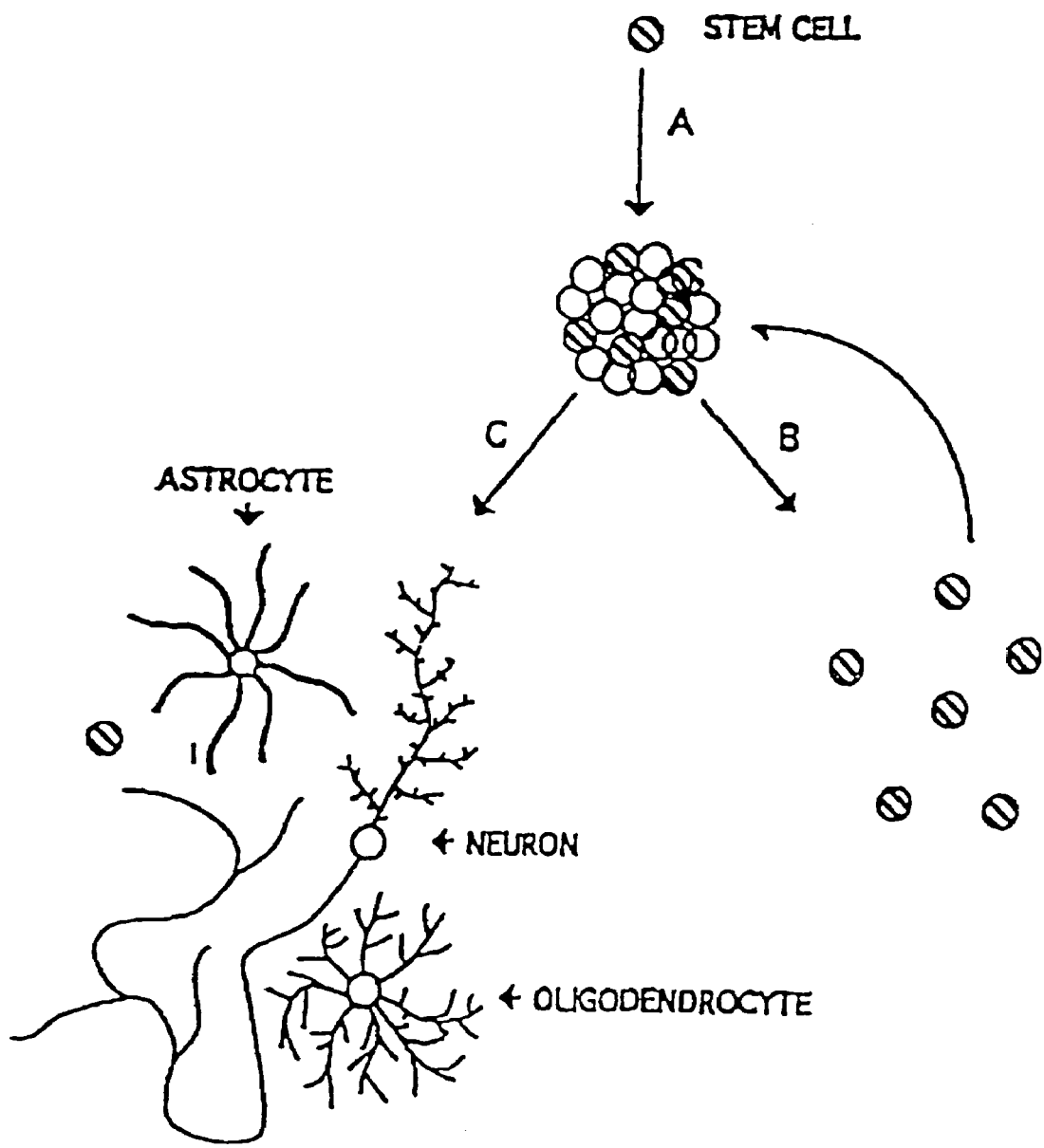
FIG. 1: Diagram Illustrating the Proliferation of a Multipotent Neural Stem Cell (A) In the presence of a proliferation-inducing growth factor the stem cell divides and gives rise to a sphere of undifferentiated cells composed of more stem cells and progenitor cells. (B) When the clonally derived sphere of undifferentiated cells is dissociated and plated as single cells, on a non-adhesive substrate and in the presence of a proliferation-inducing growth factor, each stem cell will generate a new sphere. (C) If the spheres are cultured in conditions that allow differentiation, the progenitor cells differentiate into neurons, astrocytes and oligodendrocytes.
Figure 2:
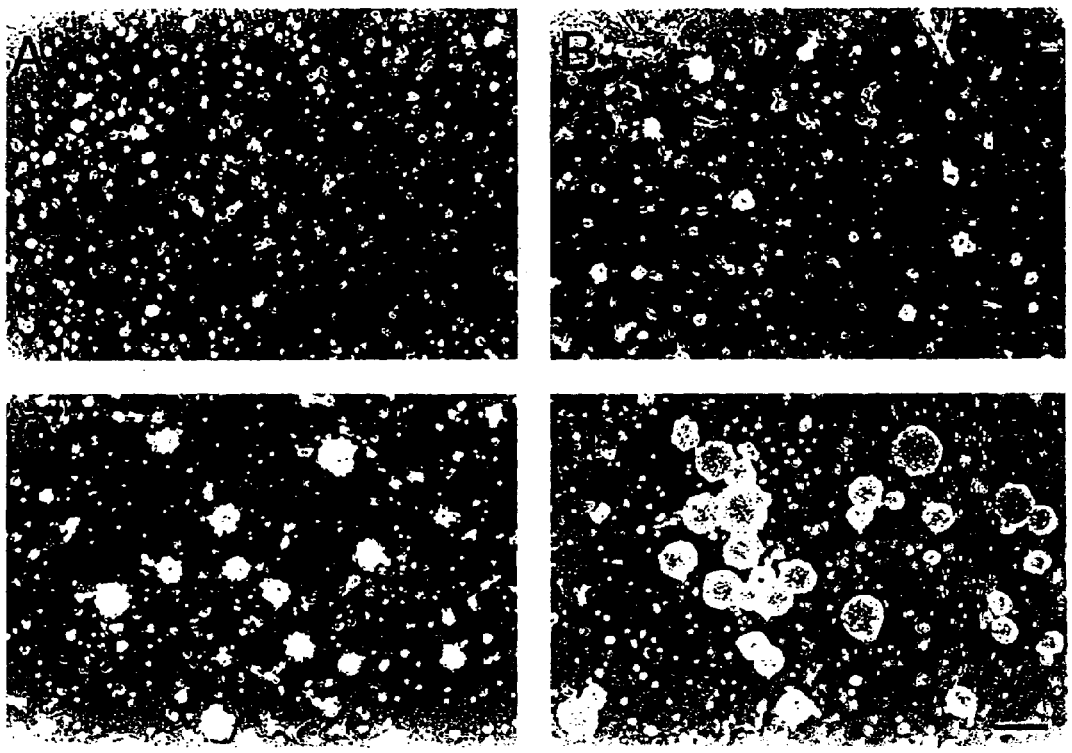
FIG. 2: Proliferation of Epidermal Growth Factor (EGF) Responsive Cells

After 2 days in vitro EGF-responsive cells begin to proliferate (FIG. 2A). After 4 days in vitro small clusters of cells known as neurospheres are apparent (FIG. 2B).

The neurospheres of continuously proliferating cells continue to grow in size (FIG. 2C) until they lift off the substrate and float in suspension (FIG. 2D). At this stage, the floating spheres can be easily removed, dissociated into single cells and, in the presence of EGF, proliferation can be re-initiated. (Bar: 50 µm).

Figure 3:
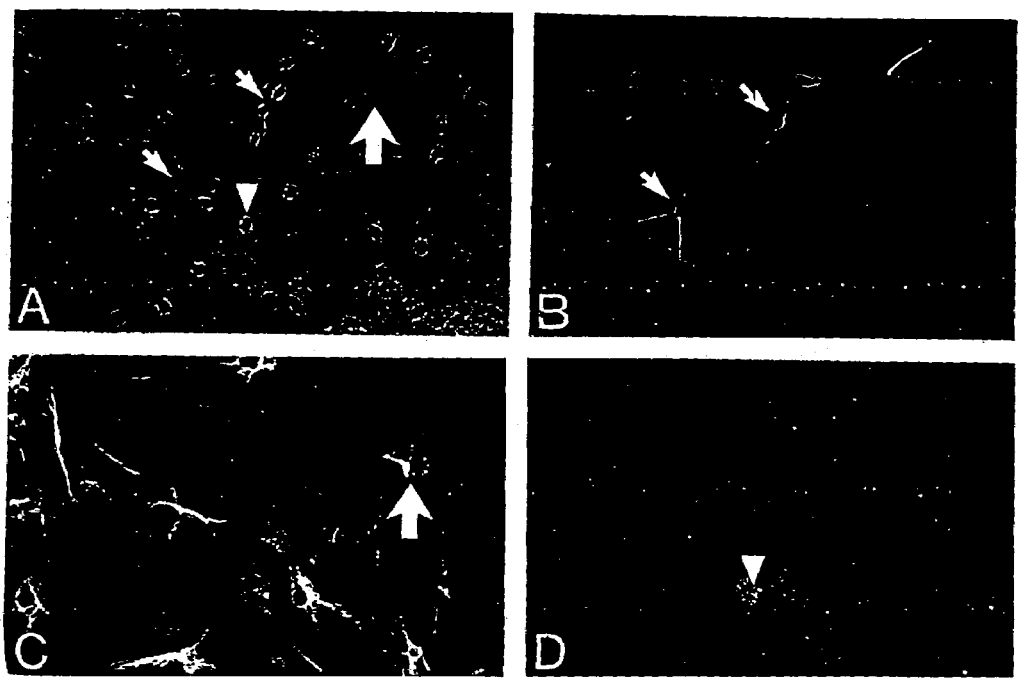

FIG. 3: Differentiation of Cells From Single EGF-Generated Spheres into Neurons, Astrocytes, and Oligodendrocytes Triple-label immunocytochemistry with antibodies to microtubule associated protein (MAP-2), glial fibrillary acidic protein (GFAP), and O4 (a cell surface antigen) are used to detect the presence of neurons (FIG. 3B), astrocytes (FIG. 3C) and oligodendrocytes (FIG. 3D), respectively, from an EGF-generated, stem cell-derived neurosphere (FIG. 3A) derived from primary culture. (Bar: 50 µm).

DETAILED DESCRIPTION OF THE INVENTION

The present invention provides methods for inducing multipotent neural stem cells from fetal, juvenile, or adult mammalian tissue to proliferate in vitro or in vivo (i.e. in situ), to generate large numbers of neural stem cell progeny capable of differentiating into neurons, astrocytes, and oligodendrocytes. Methods for differentiation of the neural stem cell progeny are also provided. The induction of proliferation and differentiation of neural stem cells can be done either by culturing the cells in suspension or on a substrate onto which they can adhere. Alternatively, proliferation and differentiation of neural stem cells can be induced, under appropriate conditions, in the host in the following combinations: (1) proliferation and differentiation in vitro, then transplantation, (2) proliferation in vitro, transplantation, then further proliferation and differentiation in vivo, (3) proliferation in vitro, transplantation and differentiation in vivo, and (4) proliferation and differentiation in vivo. Proliferation and differentiation in vivo (i.e. in situ) can involve a non-surgical approach that coaxes neural stem cells to proliferate in vivo with pharmaceutical manipulation. Thus, the invention provides a means for generating large numbers of undifferentiated and differentiated neural cells for neurotransplantation into a host in order to treat neurodegenerative disease and neurological trauma, for non-surgical methods of treating neurodegenerative disease and neurological trauma, and for drug-screening applications.

Multipotent Neural Stem Cells

Neurobiologists have used various terms interchangeably to describe the undifferentiated cells of the CNS. Terms such as "stem cell", "precursor cell" and "progenitor cell" are commonly used in the scientific literature. However, there are different types of undifferentiated neural cells, with differing characteristics and fates. U.S. Ser. No. 08/270,412 which is a continuation application of U.S. Ser. No. 07/726,812, termed the cells obtained and proliferated using the methods of Examples 1–4 below "progenitor cells". The terminology used for undifferentiated neural cells has evolved such that these cells are now termed "neural stem cells". U.S. Ser. No. 08/270,412 defines the "progenitor" cell proliferated in vitro to mean "an oligopotent or multipotent stem cell which is able to divide without limit and under specific conditions can produce daughter cells which terminally differentiate into neurons and glia." The capability of a cell to divide without limit and produce daughter cells which terminally differentiate into neurons and glia are stem cell characteristics. Accordingly, as used herein, the cells proliferated using the methods described in Examples 1–4 are termed "neural stem cells". A neural stem cell is an undifferentiated neural cell that can be induced to proliferate using the methods of the present invention. The neural stem cell is capable of self-maintenance, meaning that with each cell division, one daughter cell will also be a stem cell. The non-stem cell progeny of a neural stem cell are termed progenitor cells. The progenitor cells generated from a single multipotent neural stem cell are capable of differentiating into neurons, astrocytes (type I and type II) and oligodendrocytes. Hence, the neural stem cell is "multipotent" because its progeny have multiple differentiative pathways.

The term "neural progenitor cell", as used herein, refers to an undifferentiated cell derived from a neural stem cell, and is not itself a stem cell. Some progenitor cells can produce progeny that are capable of differentiating into more than one cell type. For example, an O-2A cell is a glial progenitor cell that gives rise to oligodendrocytes and type II astrocytes, and thus could be termed a "bipotential" progenitor cell. A distinguishing feature of a progenitor cell is that, unlike a stem cell, it has limited proliferative ability and thus does not exhibit self-maintenance. It is committed to a particular path of differentiation and will, under appropriate conditions, eventually differentiate into glia or neurons.

The term "precursor cells", as used herein, refers to the progeny of neural stem cells, and thus includes both progenitor cells and daughter neural stem cells.

Neural stem cell progeny can be used for transplantation into a heterologous, autologous, or xenogeneic host. Multipotent neural stem cells can be obtained from embryonic, post-natal, juvenile or adult neural tissue. The neural tissue can be obtained from any animal that has neural tissue such as insects, fish, reptiles, birds, amphibians, mammals and the like. The preferred source neural tissue is from mammals, preferably rodents and primates, and most preferably, mice and humans.

In the case of a heterologous donor animal, the animal may be euthanized, and the neural tissue and specific area of interest removed using a sterile procedure. Areas of particular interest include any area from which neural stem cells can be obtained that will serve to restore function to a degenerated area of the host's nervous system, particularly the host's CNS. Suitable areas include the cerebral cortex, cerebellum, midbrain, brainstem, spinal cord and ventricular tissue, and areas of the PNS including the carotid body and the adrenal medulla. Preferred areas include regions in the basal ganglia, preferably the striatum which consists of the caudate and putamen, or various cell groups such as the globus pallidus, the subthalamic nucleus, the nucleus basalis which is found to be degenerated in Alzheimer's Disease patients, or the substantia nigra pars compacta which is found to be degenerated in Parkinson's Disease patients. Particularly preferred neural tissue is obtained from ventricular tissue that is found lining CNS ventricles and includes the subependyma. The term "ventricle" refers to any cavity or passageway within the CNS through which cerebral spinal fluid flows. Thus, the term not only encompasses the lateral, third, and fourth ventricles, but also encompasses the central canal, cerebral aqueduct, and other CNS cavities.

Human heterologous neural stem cells may be derived from fetal tissue following elective abortion, or from a post-natal, juvenile or adult organ donor. Autologous neural tissue can be obtained by biopsy, or from patients undergoing neurosurgery in which neural tissue is removed, for example, during epilepsy surgery, temporal lobectomies and hippocampalectomies. Neural stem cells have been isolated from a variety of adult CNS ventricular regions, including the frontal lobe, conus medullaris, thoracic spinal cord, brain stem, and hypothalamus, and proliferated in vitro using the methods detailed herein. In each of these cases, the neural stem cell exhibits self-maintenance and generates a large number of progeny which include neurons, astrocytes and oligodendrocytes.

Normally, the adult mammalian CNS is mitotically quiescent in vivo with the exception of the subependymal region lining the lateral ventricles in the forebrain. This region contains a subpopulation of constitutively proliferating cells with a cell cycle time of 12.7 hours. BrdU and retroviral labeling of the proliferating cells reveal that none of the newly generated cells differentiate into mature neurons or glia nor do they migrate into other CNS regions (Morshead and Van der Kooy, supra).

The continual proliferation and maintenance of a constant number of cells within the subependyma is explained by two mechanisms. The death of one of the daughter cells after each division maintains the proliferating population at a constant number. The constitutively dividing population eventually dies out (and hence is not a stem cell population) however, a subpopulation of relatively quiescent cells within the subependyma is able to repopulate the constitutively dividing population. This stem cell-like mode of maintaining the proliferative subependymal population is analogous to other tissues where cells have a short life span and are repopulated by a subpopulation of relatively quiescent cells referred to as stem cells.

As detailed in Example 27, experiments utilizing retrovirus infection of constituitively proliferating cells in vivo and subsequent β-galactosidase (β-gal) reporter gene expression as a non-diluting marker show that with increasing adult mice survival times (of up to 28 days post retrovirus infection) there is a progressive loss of β-gal positive subependymal cells. Relative to 1 day survival animals, 6 days following retrovirus injection there is a 45% loss of β-gal positive cells and 28 days following retrovirus infection there is a 97% loss. Using nested polymerase chain reaction (PCR) to identify single cells containing retroviral DNA it was determined that the loss of β-gal expressing cells is due to the loss of the retrovirally infected cells through cell death, not due to the turn-off of β-gal expression.

Intraperitoneal injections of BrdU (a thymidine analog that is incorporated into the DNA of dividing cells) reveal that 33% of the cells within some regions of the subependyma make up the normally constituitively dividing population (see Morshead and van der Kooy, *J. Neurosci.* 12:249 (1992)). The number of BrdU labelled cells decreases over time. By 30 days after BrdU labeling, only 3% of the dividing cells are still labelled. The heavy labeling of only a small number of cells 30 days after BrdU injections demonstrates that although the labelled cells were dividing at the time of the injections they were relatively quiescent for the 30 day period. This suggests that these few labeled cells are stem cells rather than cells of the constitutively proliferating population.

The above two examples support the hypothesis that the maintenance of the constant number of proliferating subependymal cells seen throughout adult life requires the presence of a relatively quiescent stem cell that proliferates sporadically to replenish the constitutively proliferating population and to self-renew.

As detailed in Example 24, the constitutively dividing subependymal cells can be killed off by injecting high doses of radioactive thymidine for the duration of the cell cycle at intervals less than S-phase duration. At one day post-kill the proliferating population is 10% of controls and by 8 days the proliferating population is back to control levels. If the replenished population is due to the recruitment of normally quiescent stem cells into the proliferative mode, then a second kill at the time that stem cells are generating progeny to repopulate the subependyma should alter the number of cells within the constitutively proliferating population. When a second kill is done 2 days after the initial kill, 8 days later the constitutively proliferating population is only 45% of the control values (animals receiving no thymidine kill treatment) or animals that received only one kill at day 0 (the time of the first kill). The reduction in the number of proliferative cells in the subependyma is maintained at 63% even at 31 days after the second kill. When a second kill is done on day 4, the proliferating population returns to 85% of control values 8 days later. These results suggest that the normally quiescent stem cell is recruited into the proliferative mode within the first two days after the initial kill and that by 4 days the stem cell no longer needs to be recruited to repopulate the subependyma.

As detailed in Example 26 below, an experiment was performed to determine whether the in vitro stem cell is derived from the constitutively proliferating population or from the quiescent population. Animals were treated in one of the following ways:

| Group 1. | Control |
|---|---|
| High doses of radioactive thymidine were given on: | |
| Group 2. | day 0 |
| Group 3. | day 0 and day 2 |
| Group 4. | day 0 and day 4 |

16 to 20 following the last injection animals were killed and stem cells isolated from the striatum (including the subependymal region) via the methods described in Example 2 below.

In groups 2–4 the constitutively proliferating population was killed. In group 3 stem cells that are recruited into the cell cycle to repopulate the subependymal proliferating cells were also killed.

| Number of Neurospheres produced in vitro: | |
|---|---|
| Group 1. | 100% (Control) |
| Group 2. | 100% |
| Group 3. | 45% |
| Group 4. | 85% |

These results demonstrate that when you eliminate nearly all of the constitutively proliferating cells in the subependyma this does not affect the number of stem cells that can be isolated and proliferated in vitro (group 1 vs. group 2 and 4). However, when the normally quiescent cells are killed when they are recruited to repopulate the subependyma (as with group 3) the number of stem cells that can be isolated in vitro is significantly reduced (group 3 vs. group 1 and 2). By 4 days after the first kill most of the stem cells themselves are no longer turning over and as a result are not killed by the second series of tritiated thymidine injections (hence, only a 15% reduction [group 4] compared to 55% reduction [group 3]).

The above results demonstrate that, in adult, the stem cells which are proliferated in vitro are derived from the quiescent population of subependymal cells in vivo.

This also explains why stem cells can be derived from CNS ventricular regions, other than the forebrain, which do not have a subpopulation of constitutively proliferating cells.

In Vitro Proliferation of Neural Stem Cells

Cells can be obtained from donor tissue by dissociation of individual cells from the connecting extracellular matrix of the tissue. Tissue from a particular neural region is removed from the brain using a sterile procedure, and the cells are dissociated using any method known in the art including treatment with enzymes such as trypsin, collagenase and the like, or by using physical methods of dissociation such as with a blunt instrument. Dissociation of fetal cells can be carried out in tissue culture medium, while a preferable medium for dissociation of juvenile and adult cells is low $Ca^{2+}$ artificial cerebral spinal fluid (aCSF). Regular aCSF contains 124 mM NaCl, 5 mM KCl, 1.3 mM $MgCl_2$, 2 mM $CaCl_2$, 26 mM $NaHCO_3$, and 10 mM D-glucose. Low $Ca^{2+}$ aCSF contains the same ingredients except for $MgCl_2$ at a concentration of 3.2 mM and $CaCl_2$ at a concentration of 0.1 mM. Dissociated cells are centrifuged at low speed, between 200 and 2000 rpm, usually between 400 and 800 rpm, and then resuspended in culture medium. The neural cells can be cultured in suspension or on a fixed substrate. However, substrates tend to induce differentiation of the neural stem cell progeny. Thus, suspension cultures are preferred if large numbers of undifferentiated neural stem cell progeny are desired. Cell suspensions are seeded in any receptacle capable of sustaining cells, particularly culture flasks, culture plates or roller bottles, and more particularly in small culture flasks such as 25 $cm^2$ culture flasks. Cells cultured in suspension are resuspended at approximately $5 \times 10^4$ to $2 \times 10^5$ cells/ml, preferably $1 \times 10^5$ cells/ml. Cells plated on a fixed substrate are plated at approximately $2–3 \times 10^3$ cells/$cm^2$, preferably $2.5 \times 10^3$ cells/$cm^2$.

The dissociated neural cells can be placed into any known culture medium capable of supporting cell growth, including HEM, DMEM, RPMI, F-12, and the like, containing supplements which are required for cellular metabolism such as glutamine and other amino acids, vitamins, minerals and useful proteins such as transferrin and the like. Medium may also contain antibiotics to prevent contamination with yeast, bacteria and fungi such as penicillin, streptomycin, gentamicin and the like. In some cases, the medium may contain serum derived from bovine, equine, chicken and the like. However, a preferred embodiment for proliferation of neural stem cells is to use a defined, serum-free culture medium, as serum tends to induce differentiation and contains unknown components (i.e. is undefined). A defined culture medium is also preferred if the cells are to be used for transplantation purposes. A particularly preferable culture medium is a defined culture medium comprising a mixture of DMEM, F12, and a defined hormone and salt mixture. This culture medium is referred to herein as "Complete Medium" and is described in detail in Example 3.

Conditions for culturing should be close to physiological conditions. The pH of the culture medium should be close to physiological pH, preferably between pH 6–8, more preferably between about pH 7 to 7.8, with pH 7.4 being most preferred. Physiological temperatures range between about 30° C. to 40° C. Cells are preferably cultured at temperatures between about 32° C. to about 38° C., and more preferably between about 35° C. to about 37° C.

The culture medium is supplemented with at least one proliferation-inducing growth factor. As used herein, the term "growth factor" refers to a protein, peptide or other molecule having a growth, proliferative, differentiative, or trophic effect on neural stem cells and/or neural stem cell progeny. Growth factors which may be used for inducing proliferation include any trophic factor that allows neural stem cells and precursor cells to proliferate, including any molecule which binds to a receptor on the surface of the cell to exert a trophic, or growth-inducing effect on the cell. Preferred proliferation-inducing growth factors include EGF, amphiregulin, acidic fibroblast growth factor (aFGF or FGF-1), basic fibroblast growth factor (bFGF or FGF-2), transforming growth factor alpha (TGFα), and combinations thereof.

Preferred proliferation-inducing growth factors include EGF and TGFα. A preferred combination of proliferation-inducing growth factors is EGF or TGFα with FGF-1 or FGF-2. Growth factors are usually added to the culture medium at concentrations ranging between about 1 fg/ml to 1 mg/ml. Concentrations between about 1 to 100 ng/ml are usually sufficient. Simple titration experiments can be easily performed to determine the optimal concentration of a particular growth factor.

In addition to proliferation-inducing growth factors, other growth factors may be added to the culture medium that influence proliferation and differentiation of the cells including NGF, platelet-derived growth factor (PDGF), thyrotropin releasing hormone (TRH), transforming growth factor betas (TGFβs), insulin-like growth factor ($IGF_{-1}$) and the like.

Within 3–4 days in the presence of a proliferation-inducing growth factor, a multipotent neural stem cell begins to divide giving rise to a cluster of undifferentiated cells referred to herein as a "neurosphere". The cells of a single neurosphere are clonal in nature because they are the progeny of a single neural stem cell. In the continued presence of a proliferation-inducing growth factor such as EGF or the like, precursor cells within the neurosphere continue to divide resulting in an increase in the size of the neurosphere and the number of undifferentiated cells. The neurosphere is not immunoreactive for GFAP, neurofilament (NF), neuron-specific enolase (NSE) or myelin basic protein (MBP). However, precursor cells within the neurosphere are immunoreactive for nestin, an intermediate filament protein found in many types of undifferentiated CNS cells. The nestin marker was characterized by Lehndahl et al., *Cell* 60:585–595 (1990).

Antibodies are available to identify nestin, including the rat antibody referred to as Rat401. The mature phenotypes associated with the differentiated cell types that may be derived from the neural stem cell progeny are predominantly negative for the nestin phenotype.

After about 4 to 5 days in the absence of a substrate, the proliferating neurospheres lift off the floor of the culture dish and tend to form the free-floating clusters characteristic of neurospheres. Floating neurospheres are depicted in FIG. 2d. It is possible to vary the culture conditions so that while the precursor cells still express the nestin phenotype, they do not form the characteristic neurospheres. The proliferating precursor cells of the neurosphere continue to proliferate in suspension. After about 3–10 days in vitro, and more particularly after about 6–7 days in vitro, the proliferating neurospheres are fed every 2–7 days, preferably every 2–4 days by gentle centrifugation and resuspension in Complete Medium containing a growth factor.

The neurospheres of the suspension culture can be easily passaged to reinitiate proliferation. After 6–7 days in vitro, the culture flasks are shaken well and the neurospheres allowed to settle on the bottom corner of the flask. The neurospheres are then transferred to a 50 ml centrifuge tube and centrifuged at low speed. The medium is aspirated, and the neurospheres are resuspended in a small amount of Complete Medium. Individual cells in the neurospheres can be separated by physical dissociation of the neurospheres with a blunt instrument, for example, by triturating the neurospheres with a pipette, especially a fire polished pasteur pipette, to form a single cell suspension of neural stem cell progeny. The cells are then counted and replated at the desired density to reinitiate proliferation. Single cells from the dissociated neurospheres are suspended in Complete Medium containing growth factor, and a percentage of these cells proliferate and form new neurospheres largely composed of undifferentiated cells. This procedure can be repeated weekly to result in a logarithmic increase in the number of viable cells at each passage. The procedure is continued until the desired number of precursor cells is obtained.

The number of neural stem cell progeny proliferated in vitro from the mammalian CNS can be increased dramatically by injecting a growth factor or combination of growth factors, for example EGF, FGF, or EGF and FGF together, into the ventricles of the donor in vivo using the in vivo proliferation methods described in more detail below. As detailed in Example 31 below, 6 days after infusion of EGF into the lateral ventricle of a mouse forebrain, the walls of the ventricle were removed and the stem cells harvested. Infusion of EGF into the lateral ventricle increased the efficiency of the yield of stem cells that proliferated to form neurospheres.

This ability to enhance the proliferation of neural stem cells should prove invaluable when stem cells are to be harvested for later transplantation back into a patient, thereby making the initial surgery 1) less traumatic because less tissue would have to be removed and 2) more efficient because a greater yield of stem cells per surgery would proliferate in vitro.

Additionally, the patient's stem cells, once they have proliferated in vitro, could also be genetically modified in vitro using the techniques described below. The in vitro genetic modification may be more desirable in certain circumstances than in vivo genetic modification techniques when more control over the infection with the genetic material is required.

Neural stem cell progeny can be cryopreserved until they are needed by any method known in the art. The cells can be suspended in an isotonic solution, preferably a cell culture medium, containing a particular cryopreservant. Such cryopreservants include dimethyl sulfoxide (DMSO), glycerol and the like. These cryopreservants are used at a concentration of 5–15%, preferably 8–10%. Cells are frozen gradually to a temperature of −10° C. to preferably to −20° C. to −100° C., and more preferably 70° C. to 80° C.

Differentiation of Neural Stem Cell Progeny

Differentiation of the cells can be induced by any method known in the art which activates the cascade of biological events which lead to growth, which include the liberation of inositol triphosphate and intracellular $Ca^{2+}$, liberation of diacyl glycerol and the activation of protein kinase C and other cellular kinases, and the like. Treatment with phorbol esters, differentiation-inducing growth factors and other chemical signals can induce differentiation. Differentiation can also be induced by plating the cells on a fixed substrate such as flasks, plates, or coverslips coated with an ionically charged surface such as poly-L-lysine and poly-L-ornithine and the like.

Other substrates may be used differentiation such as collagen, fibronectin, laminin, MATRIGEL™ (Collaborative Research), and the like. Differentiation can also be induced by leaving the cells in suspension in the presence of a proliferation-inducing growth factor, without reinitiation of proliferation (i.e. without dissociating the neurospheres).

A preferred method for inducing differentiation of the neural stem cell progeny comprises culturing the cells on a fixed substrate in a culture medium that is free of the proliferation-inducing growth factor. After removal of the proliferation-inducing growth factor, the cells adhere to the substrate (e.g. poly-ornithine-treated plastic or glass), flatten, and begin to differentiate into neurons and glial cells. At this stage the culture medium may contain serum such as 0.5–1.0% fetal bovine serum (FBS). However, for certain uses, if defined conditions are required, serum would not be used. Within 2–3 days, most or all of the neural stem cell progeny begin to lose immunoreactivity for nestin and begin to express antigens specific for neurons, astrocytes or oligodendrocytes as determined by immunocytochemistry techniques well known in the art.

Immunocytochemistry (e.g. dual-label immunofluorescence and immunoperoxidase methods) utilizes antibodies that detect cell proteins to distinguish the cellular characteristics or phenotypic properties of neurons from astrocytes and oligodendrocytes. In particular, cellular markers for neurons include NSE, NF, β-tub, MAP-2; and for glia, GFAP (an identifier of astrocytes), galactocerebroside (GalC) (a myelin glycolipid identifier of oligodendrocytes), and the like.

Immunocytochemistry can also be used to detect the expression of neurotransmitters, or in some cases the expression of enzymes responsible for neurotransmitter synthesis. For the identification of neurons, antibodies can be used that detect the presence of acetylcholine (ACh), dopamine, epinephrine, norepinephrine, histamine, serotonin or 5-hydroxytryptamine (5-HT), neuropeptides such as substance P, adrenocorticotrophic hormone, vasopressin or anti-diuretic hormone, oxytocin, somatostatin, angiotensin II, neurotensin, and bombesin, hypothalamic releasing hormones such as TRH and luteinizing releasing hormone, gastrointestinal peptides such as vasoactive intestinal peptide (VIP) and cholecystokinin (CCK) and CCK-like peptide, opioid peptides such as endorphins like β-endorphin and enkephalins such as met- and leu-enkephalin, prostaglandins, amino acids such as y-amino butyric acid (GABA) glycine, glutamate, cysteine, taurine and aspartate and dipeptides such as carnosine. Antibodies to neurotransmitter-synthesizing enzymes can also be used such as glutamic acid decarboxylase (GAD) which is involved in the synthesis of GABA, choline acetyltransferase (ChAT) for ACh synthesis, dopa decarboxylase (DDC) for dopamine, dopamine-β-hydroxylase (DBH) for norepinephrine, and amino acid decarboxylase for 5-HT. Antibodies to enzymes that are involved in the deactivation of neurotransmitters may also be useful such as acetyl cholinesterase (AChE) which deactivates ACh. Antibodies to enzymes involved in the reuptake of neurotransmitters into neuronal terminals such as monoamine oxidase and catechol-o-methyl transferase for dopamine, for 5-HT, and GABA transferase for GABA may also identify neurons. Other markers for neurons include antibodies to neurotransmitter receptors such as the AChE nicotinic and muscarinic receptors, adrenergic receptors $\alpha^1$, $\alpha_2$, $\beta^1$ and $\alpha_2$, the dopamine receptor and the like. Cells that contain a high level of melanin, such as those found in the substantia nigra, could be identified using an antibody to melanin.

In situ hybridization histochemistry can also be performed, using cDNA or RNA probes specific for the peptide neurotransmitter or the neurotransmitter synthesizing enzyme mRNAs. These techniques can be combined with immunocytochemical methods to enhance the identification of specific phenotypes. If necessary, the antibodies and molecular probes discussed above can be applied to Western and Northern blot procedures respectively to aid in cell identification.

A preferred method for the identification of neurons uses immunocytochemistry to detect immunoreactivity for NSE, NF, NeuN, and the neuron specific protein, tau-1. Because these markers are highly reliable, they will continue to be useful for the primary identification of neurons, however neurons can also be identified based on their specific neurotransmitter phenotype as previously described.

Type I astrocytes, which are differentiated glial cells that have a flat, protoplasmic/fibroblast-like morphology, are preferably identified by their immunoreactivity for GFAP but not A2B5. Type II astrocytes, which are differentiated glial cells that display a stellate process-bearing morphology, are preferably identified using immunocytochemistry by their phenotype GFAP(+), A2B5(+) phenotype.

Cells that do not express intermediate filaments specific for neurons or for astrocytes, begin to express markers specific for oligodendrocytes in a correct temporal fashion. That is, the cells first become immunoreactive for O4, galactocerebroside (GalC, a myelin glycolipid) and finally, MBP. These cells also possess a characteristic oligodendrocyte morphology.

The present invention provides a method of influencing the relative proportion of these differentiated cell types by the addition of exogenous growth factors during the differentiation stage of the precursor cells. By using dual-label immunofluorescence and immunoperoxidase methods with various neuronal- and glial-specific antibodies, the effect of the exogenous growth factors on the differentiating cells can be determined.

The biological effects of growth and trophic factors are generally mediated through binding to cell surface receptors. The receptors for a number of these factors have been identified and antibodies and molecular probes for specific receptors are available. Neural stem cells can be analyzed for the presence of growth factor receptors at all stages of differentiation. In many cases, the identification of a particular receptor will define the strategy to use in further differentiating the cells along specific developmental pathways with the addition of exogenous growth or trophic factors.

Exogenous growth factors can be added alone or in various combinations. They can also be added in a temporal sequence (i.e. exposure to a first growth factor influences the expression of a second growth factor receptor, Neuron 4:189–201 (1990). Among the growth factors and other molecules that can be used to influence the differentiation of precursor cells in vitro are FGF-1, FGF-2, ciliary neurotrophic factor (CNTF), NGF, brain-deprived neurotrophic-factor (BDNF), neurotrophin 3, neurotrophin 4, interleukins, leukemia inhibitory factor (LIF), cyclic adenosine monophosphate, forskolin, tetanus toxin, high levels of potassium, amphiregulin, TGF-α, TGF-β, insulin-like growth factors, dexamethasone (glucocorticoid hormone), isobutyl 3-methylxanthine, somatostatin, growth hormone, retinoic acid, and PDGF. These and other growth factors and molecules will find use in the present invention.

Genetic Modification of Neural Stem Cell Progeny

Although the precursor cells are non-transformed primary cells, they possess features of a continuous cell line. In the undifferentiated state, in the presence of a proliferation-inducing growth factor such as EGF, the cells continuously divide and are therefore excellent targets for genetic modification. The term "genetic modification" as used herein refers to the stable or transient alteration of the genotype of a precursor cell by intentional introduction of exogenous DNA. DNA may be synthetic, or naturally derived, and may contain genes, portions of genes, or other useful DNA sequences. The term "genetic modification" as used herein is not meant to include naturally occurring alterations such as that which occurs through natural viral activity, natural genetic recombination, or the like.

Exogenous DNA may be introduced to a precursor cell by viral vectors (retrovirus, modified herpes viral, herpes-viral, adenovirus, adeno-associated virus, and the like) or direct DNA transfection (lipofection, calcium phosphate transfection, DEAE-dextran, electroporation, and the like). The genetically modified cells of the present invention possess the added advantage of having the capacity to fully differentiate to produce neurons or macroglial cells in a reproducible fashion using a number of differentiation protocols.

In another embodiment, the precursor cells are derived from transgenic animals, and thus are in a sense already genetically modified. There are several methods presently used for generating transgenic animals. The technique used most often is direct microinjection of DNA into single-celled fertilized eggs. Other techniques include retroviral-mediated transfer, or gene transfer in embryonic stem cells. These techniques and others are detailed by Hogan et al. in *Manipulating the Mouse Embryo, A Laboratory Manual* (Cold Spring Harbor Laboratory Ed., 1986). Use of these transgenic animals has certain advantages including the fact that there is no need to transfect healthy neurospheres. Precursor cells derived from transgenic animals will exhibit stable gene expression. Using transgenic animals, it is possible to breed in new genetic combinations. The transgenic animal may have integrated into its genome any useful gene that is expressed by neural cells. Examples of useful DNA are given below in the discussion of genetically modifying precursor cells.

A significant challenge for cellular transplantation in the CNS is the identification of the donor cells after implantation within the host. A number of strategies have been employed to mark donor cells, including tritiated labels, fluorescent dyes, dextrans, and viral vectors carrying reporter genes. However, these methods suffer from inherent problems of toxicity, stability, or dilution over the long term. The use of neural cells derived from transgenic animals may provide an improved means by which identification of transplanted neural cells can be achieved. A transgenic marking system provides a more stable and efficient method for cell labeling. In this system, promoter elements, for example for GFAP and MBP, can direct the expression of the *E. coli* B-galactosidase reporter gene in transgenic mice. In these systems, cell-specific expression of the reporter gene occurs in astrocytes (GFAP-lacZ) and in oligodendrocytes (MBP-lacZ) in a developmentally-regulated manner. The Rosa26 transgenic mice, described in Example 45, is one example of a transgenic marking system in which all cells ubiquitously express β-galactosidase.

Once propagated, the neurosphere cells are mechanically dissociated into a single cell suspension and plated on petri dishes in a medium where they are allowed to attach overnight. The precursor cells are then genetically modified. If the precursor cells are generated from transgenic animals, then they may or may not be subjected to further genetic modification, depending upon the properties desired of the cells. Any useful genetic modification of the cells is within the scope of the present invention. For example, precursor cells may be modified to produce or increase production of a biologically active substance such as a neurotransmitter or growth factor or the like. The genetic modification is performed either by infection with recombinant retroviruses or transfection using methods known in the art (see Maniatis et al., in *Molecular Cloning: A Laboratory Manual*, Cold Spring Harbor Laboratory, N.Y. (1982)). Briefly, the chimeric gene constructs will contain viral, for example retroviral long terminal repeat (LTR), simian virus 40 (SV40), cytomegalovirus (CMV); or mammalian cell-specific promoters such as tyrosine hydroxylase (TH, a marker for dopamine cells), DBH, phenylethanolamine N-methyltransferase (PNMT), ChAT, GFAP, NSE, the NF proteins (NF-L, NF-M, NF-H, and the like) that direct the expression of the structural genes encoding the desired protein. In addition, the vectors will include a drug selection marker, such as the *E. coli* aminoglycoside phosphotransferase gene, which when coinfected with the experimental gene confers resistance to geneticin (G418), a protein synthesis inhibitor.

When the genetic modification is for the production of a biologically active substance, the substance will generally be one that is useful for the treatment of a given CNS disorder. For example, it may be desired to genetically modify cells so they secrete a certain growth factor product. As used herein, the term "growth factor product" refers to a protein, peptide, mitogen, or other molecule having a growth, proliferative, differentiative, or trophic effect. Growth factor products useful in the treatment of CNS disorders include, but are not limited to, NGF, BDNF, the neurotrophins (NT-3, NT-4/NT-5), CNTF, amphiregulin, FGF-1, FGF-2, EGF, TGFα, TGFβs, PDGF, IGFs, and the interleukins.

Cells can also be modified to express a certain growth factor receptor (r) including, but not limited to, p75 low affinity NGFr, CNTFr, the trk family of neurotrophin receptors (trk, trkB, trkC), EGFr, FGFr, and amphiregulin receptors. Cells can be engineered to produce various neurotransmitters or their receptors such as serotonin, L-dopa, dopamine, norepinephrine, epinephrine, tachykinin, substance-P, endorphin, enkephalin, histamine, N-methyl D-aspartate, glycine, glutamate, GABA, ACh, and the like. Useful neurotransmitter-synthesizing genes include TH, DDC, DBH, PNMT, GAD, tryptophan hydroxylase, ChAT, and histidine decarboxylase. Genes that encode for various neuropeptides, which may prove useful in the treatment of CNS disorders, include substance-P, neuropeptide-Y, enkephalin, vasopressin, VIP, glucagon, bombesin, CCK, somatostatin, calcitonin gene-related peptide, and the like.

After successfully transfected/infected cells are selected they can be cloned using limiting dilution in 96 multi-well plates and assayed for the presence of the desired biologically active substance. Clones that express high levels of the desired substance are grown and their numbers expanded in T-flasks. The specific cell line can then be cyropreserved. Multiple clones of genetically modified precursor cells will be obtained. Some may give rise preferentially to neuronal cells, and some to glial cells.

The genetically modified precursor cells can be implanted for cell/gene therapy into the CNS of a recipient in need of the biologically active molecule produced by the genetically modified cells. Transplantation techniques are detailed below.

Alternatively, the genetically modified precursor cells can be subjected to various differentiation protocols in vitro prior to implantation. For example, genetically modified precursor cells may be removed from the culture medium which allows proliferation and differentiated using any of the protocols described above. The protocol used will depend upon the type of genetically modified cell desired. Once the cells have differentiated, they are again assayed for expression of the desired protein. Cells having the desired phenotype can be isolated and implanted into recipients in need of the protein or biologically active molecule that is expressed by the genetically modified cell.

Transplantation of Neural Stem Cell Progeny Alleviate Disorders of the CNS in Animal Models Caused by Disease or Injury It is well recognized in the art that transplantation of tissue into the CNS offers the potential for treatment of neurodegenerative disorders and CNS damage due to injury (review: Lindvall, (1991) *Tins* vol. 14(8): 376–383). Transplantation of new cells into the damaged CNS has the potential to repair damaged circuitries and provide neurotransmitters thereby restoring neurological function. However, the absence of suitable cells for transplantation purposes has prevented the full potential of this procedure from being met. "Suitable" cells are cells that meet the following criteria: 1) can be obtained in large numbers; 2) can be proliferated in vitro to allow insertion of genetic material, if necessary; 3) capable of surviving indefinitely but stop growing after transplantation to the brain; 4) are non-immunogenic, preferably obtained from a patient's own tissue; 5) are able to form normal neural connections and respond to neural physiological signals (Bjorklund (1991) *TINS* Vol. 14(8): 319–322). The progeny of multipotent neural stem cells obtainable from embryonic or adult CNS tissue, which are able to divide indefinitely when maintained in vitro using the culture conditions described herein, meet all of the desirable requirements of cells suitable for neural transplantation purposes and are a particularly suitable cell line as the cells have not been immortalized and are not of tumorigenic origin. The use of multipotent neural stem cells in the treatment of neurological disorders and CNS damage can be demonstrated by the use of animal models.

The neural stem cell progeny can be administered to any animal with abnormal neurological or neurodegenerative symptoms obtained in any manner, including those obtained as a result of mechanical, chemical, or electrolytic lesions, as a result of experimental aspiration of neural areas, or as a result of aging processes.

Particularly preferable lesions in non-human animal models are obtained with 6-hydroxy-dopamine (6-OHDA), 1-methyl-4-phenyl-1,2,3,6 tetrahydropyridine (MPTP), ibotenic acid and the like.

The instant invention allows the use of precursor cells prepared from donor tissue which is xenogeneic to the host. Since the CNS is a somewhat immunoprivileged site, the immune response is significantly less to xenografts, than elsewhere in the body. In general, however, in order for xenografts to be successful it is preferred that some method of reducing or eliminating the immune response to the implanted tissue be employed. Thus recipients will often be immunosuppressed, either through the use of immunosuppressive drugs such as cyclosporin, or through local immunosuppression strategies employing locally applied immunosuppressants. Local immunosuppression is disclosed by Gruber, *Transplantation* 54:1–11 (1992). Rossini, U.S. Pat. No. 5,026,365, discloses encapsulation methods suitable for local immunosuppression.

As an alternative to employing immunosuppression techniques, methods of gene replacement or knockout using homologous recombination in embryonic stem cells, taught by Smithies et al. (*Nature,* 317:230–234 (1985), and extended to gene replacement or knockout in cell lines (H. Zheng 35 al., *PNAS,* 88:8067–8071 (1991)), can be applied to precursor cells for the ablation of major histocompatibility complex (MHC) genes. Precursor cells lacking MHC expression would allow for the grafting of enriched neural cell populations across allogeneic, and perhaps even xenogeneic, histocompatibility barriers without the need to immunosuppress the recipient. General reviews and citations for the use of recombinant methods to reduce antigenicity of donor cells are also disclosed by Gruber (supra). Exemplary approaches to the reduction of immunogenicity of transplants by surface modification are disclosed by Faustman WO 92/04033 (1992). Alternatively the immunogenicity of the graft may be reduced by preparing precursor cells from a transgenic animal that has altered or deleted MHC antigens.

Grafting of precursor cells prepared from tissue which is allogeneic to that of the recipient will most often employ tissue typing in an effort to most closely match the histocompatibility type of the recipient. Donor cell age as well as age of the recipient have been demonstrated to be important factors in improving the probability of neuronal graft survival. The efficiency of grafting is reduced with increased age of donor cells. Furthermore, grafts are more readily accepted by younger recipients compared to older recipients. These two factors are likely to be as important for glial graft survival as they are for neuronal graft survival.

In some instances, it may be possible to prepare neural stem cell progeny from the recipient's own nervous system (e.g. in the case of tumor removal biopsies etc,). In such instances the neural stem cell progeny may be generated from dissociated tissue and proliferated in vitro using the methods described above. Upon suitable expansion of cell numbers, the precursor cells may be harvested, genetically modified if necessary, and readied for direct injection into the recipient's CNS.

Transplantation can be done bilaterally, or, in the case of a patient suffering from Parkinson's Disease, contralateral to the most affected side. Surgery is performed in a manner in which particular brain regions may be located, such as in relation to skull sutures, particularly with a stereotaxic guide. Cells are delivered throughout any affected neural area, in particular to the basal ganglia, and preferably to the caudate and putamen, the nucleus basalis or the substantia nigra. Cells are administered to the particular region using any method which maintains the integrity of surrounding areas of the brain, preferably by injection cannula. Injection methods exemplified by those used by Duncan et al. *J. Neurocytology,* 17:351–361 (1988), and scaled up and modified for use in humans are preferred. Methods taught by Gage et al., supra, for the injection of cell suspensions such as fibroblasts into the CNS may also be employed for injection of neural precursor cells. Additional approaches and methods may be found in *Neural Grafting in the Mammalian CNS,* Bjorklund and Stenevi, eds., (1985).

Although solid tissue fragments and cell suspensions of neural tissue are immunogenic as a whole, it could be possible that individual cell types within the graft are themselves immunogenic to a lesser degree. For example, Bartlett et al. (*Prog. Brain Res.* 82: 153–160 (1990)) have abrogated neural allograft rejection by pre-selecting a sub-population of embryonic neuroepithelial cells for grafting by the use of immunobead separation on the basis of MHC expression. Thus, another approach is provided to reduce the chances of allo and xenograft rejection by the recipient without the use of immunosuppression techniques.

Neural stem cell progeny when administered to the particular neural region preferably form a neural graft, wherein the neuronal cells form normal neuronal or synaptic connections with neighboring neurons, and maintain contact with transplanted or existing glial cells which may form myelin sheaths around the neurons' axons, and provide a trophic influence for the neurons. As these transplanted cells form connections, they re-establish the neuronal networks which have been damaged due to disease and aging.

Survival of the graft in the living host can be examined using various non-invasive scans such as computerized axial tomography (CAT scan or CT scan), nuclear magnetic resonance or magnetic resonance imaging (NMR or MRI) or more preferably positron emission tomography (PET) scans. Post-mortem examination of graft survival can be done by removing the neural tissue, and examining the affected region macroscopically, or more preferably using microscopy. Cells can be stained with any stains visible under light or electron microscopic conditions, more particularly with stains which are specific for neurons and glia. Particularly useful are monoclonal antibodies which identify neuronal cell surface markers such as the M6 antibody which identifies mouse neurons. Most preferable are antibodies which identify any neurotransmitters, particularly those directed to GABA, TH, ChAT, and substance P, and to enzymes involved in the synthesis of neurotransmitters, in particular, GAD. Transplanted cells can also be identified by prior incorporation of tracer dyes such as rhodamine- or fluorescein-labelled microspheres, fast blue, bisbenzamide or retrovirally introduced histochemical markers such as the lac Z gene which produces beta galactosidase.

Functional integration of the graft into the host's neural tissue can be assessed by examining the effectiveness of grafts on restoring various functions, including but not limited to tests for endocrine, motor, cognitive and sensory functions. Motor tests which can be used include those which quantitate rotational movement away from the degenerated side of the brain, and those which quantitate slowness of movement, balance, coordination, akinesia or lack of movement, rigidity and tremors. Cognitive tests include various tests of ability to perform everyday tasks, as well as various memory tests, including maze performance.

Neural stem cell progeny can be produced and transplanted using the above procedures to treat demyelination diseases. Human demyelinating diseases for which the cells of the present invention may provide treatment include disseminated perivenous encephalomyelitis, MS (Charcot and Marburg types), neuromyelitis optica, concentric sclerosis, acute, disseminated encephalomyelitides, post encephalomyelitis, postvaccinal encephalomyelitis, acute hemorrhagic leukoencephalopathy, progressive multifocal leukoencephalopathy, idiopathic polyneuritis, diphtheric neuropathy, Pelizaeus-Merzbacher disease, neuromyelitis optica, diffuse cerebral sclerosis, central pontine myelinosis, spongiform leukodystrophy, and leukodystrophy (Alexander type).

Areas of demyelination in humans is generally associated with plaque like structures. Plaques can be visualized by magnetic resonance imaging. Accessible plaques are the target area for injection of neural stem cell progeny. Standard stereotactic neurosurgical methods are used to inject cell suspensions both into the brain and spinal cord. Generally, the cells can be obtained from any of the sources discussed above. However, in the case of demyelinating diseases with a genetic basis directly affecting the ability of the myelin forming cell to myelinate axons, allogeneic tissue would be a preferred source of the cells as autologous tissue (i.e. the recipient's cells) would generally not be useful unless the cells have been modified in some way to insure the lesion will not continue (e.g. genetically modifying the cells to cure the demyelination lesion).

Oligodendrocytes derived from neural stem cell progeny proliferated and differentiated in vitro may be injected into demyelinated target areas in the recipient. Appropriate amounts of type I astrocytes may also be injected. Type I astrocytes are known to secrete PDGF which promotes both migration and cell division of oligodendrocytes. [Nobel et al., *Nature* 333:560–652 (1988); Richardson et al., *Cell*, 53:309–319 (1988)].

A preferred treatment of demyelination disease uses undifferentiated neural stem cell progeny. Neurospheres grown in the presence of a proliferation-inducing growth factor such as EGF can be dissociated to obtain individual precursor cells which are then placed in injection medium and injected directly into the demyelinated target region. The cells differentiate in vivo. Astrocytes can promote remyelination in various paradigms. Therefore, in instances where oligodendrocyte proliferation is important, the ability of precursor cells to give rise to type I astrocytes may be useful. In other situations, PDGF may be applied topically during the transplantation as well as with repeated doses to the implant site thereafter.

The injection of neural stem cell progeny in remyelination therapy provides, amongst other types of cells, a source of immature type I astrocytes at the implant site. This is a significant feature because immature astrocytes (as opposed to mature astrocytes) have a number of specific characteristics that make them particularly suited for remyelination therapy. First, immature, as opposed to mature, type I astrocytes are known to migrate away from the implant site [Lindsay et. al, *Neurosci.* 12:513–530 (1984)] when implanted into a mature recipient and become associated with blood vessels in the recipient's CNS [Silver et al., WO 91/06631 (1991)]. This is at least partially due to the fact that immature astrocytes are intrinsically more motile than mature astrocytes. [Duffy et al., *Exp Cell Res.* 139:145–157 (1982), Table VII]. Type I astrocytes differentiating at or near the precursor cell implant site should have maximal motility and thereby optimize the opportunity for oligodendrocyte growth and division at sites distant from the implant. The localization of the astrocytes near blood vessels is also significant from a therapeutic standpoint since (at least in MS) most plaques have a close anatomical relationship with one or more veins.

Another characteristic of immature astrocytes that makes them particularly suited for remyelination therapy is that they undergo a lesser degree of cell death than mature type I astrocytes. (Silver et al., supra)

Any suitable method for the implantation of precursor cells near to the demyelinated targets may be used so that the cells can become associated with the demyelinated axons. Glial cells are motile and are known to migrate to, along, and across their neuronal targets thereby allowing the spacing of injections. Remyelination by the injection of precursor cells is a useful therapeutic in a wide range of demyelinating conditions. It should also be borne in mind that in some circumstances remyelination by precursor cells will not result in permanent remyelination, and repeated injections will be required. Such therapeutic approaches offer advantage over leaving the condition untreated and may spare the recipient's life.

In Vivo Proliferation, Differentiation, and Genetic Modification of Neural Stem Cell Progeny Neural stem cells and their progeny can be induced to proliferate and differentiate in vivo by administering to the host, any growth factor(s) or pharmaceutical composition that will induce proliferation and differentiation of the cells. These growth factors include any growth factor known in the art, including the growth factors described above for in vitro proliferation and differentiation. Pharmaceutical compositions include any substance that blocks the inhibitory influence and/or stimulates neural stem cells and stem cell progeny to proliferate and ultimately differentiate. Thus, the techniques described above to proliferate, differentiate, and genetically modify neural stem cells in vitro can be adapted to in vivo techniques, to achieve similar results. Such in vivo manipulation and modification of these cells allows cells lost, due to injury or disease, to be endogenously replaced, thus obviating the need for transplanting foreign cells into a patient. Additionally, the cells can be modified or genetically engineered in vivo so that they express various biological agents useful in the treatment of neurological disorders.

Administration of growth factors can be done by any method, including injection cannula, transfection of cells with growth hormone-expressing vectors, injection, timed-release apparati which can administer substances at the desired site, and the like. Pharmaceutical compositions can be administered by any method, including injection cannula, injection, oral administration, timed-release apparati and the like. The neural stem cells can be induced to proliferate and differentiate in vivo by induction with particular growth factors or pharmaceutical compositions which will induce their proliferation and differentiation. Therefore, this latter method circumvents the problems associated with transplantation and immune reactions to foreign cells. Any growth factor can be used, particularly EGF, TGFα, FGF-1, FGF-2 and NGF.

Growth factors can be administered in any manner known in the art in which the factors may either pass through or by-pass the blood-brain barrier. Methods for allowing factors to pass through the blood-brain barrier include minimizing the size of the factor, or providing hydrophobic factors which may pass through more easily.

The fact that neural stem cells are located in the tissues lining ventricles of mature brains offers several advantages for the modification and manipulation of these cells in vivo and the ultimate treatment of various neurological diseases, disorders, and injury that affect different regions of the CNS. Therapy for these can be tailored accordingly so that stem cells surrounding ventricles near the affected region would be manipulated or modified in vivo using the methods described herein. The ventricular system is found in nearly all brain regions and thus allows easier access to the affected areas. If one wants to modify the stem cells in vivo by exposing them to a composition comprising a growth factor or a viral vector, it is relatively easy to implant a device that administers the composition to the ventricle and thus, to the neural stem cells. For example, a cannula attached to an osmotic pump may be used to deliver the composition. Alternatively, the composition may be injected directly into the ventricles. The neural stem cell progeny can migrate into regions that have been damaged as a result of injury or disease. Furthermore, the close proximity of the ventricles to many brain regions would allow for the diffusion of a secreted neurological agent by the stem cells or their progeny.

For treatment of Huntington's Disease, Alzheimer's Disease, Parkinson's Disease, and other neurological disorders affecting primarily the forebrain, growth factors or other neurological agents would be delivered to the ventricles of the forebrain to affect in vivo modification or manipulation of the stem cells. For example, Parkinson's Disease is the result of low levels of dopamine in the brain, particularly the striatum. It would be advantageous to induce a patient's own quiescent stem cells to begin to divide in vivo and to induce the progeny of these cells to differentiate into dopaminergic cells in the affected region of the striatum, thus locally raising the levels of dopamine.

Normally the cell bodies of dopaminergic neurons are located in the substantia nigra and adjacent regions of the mesencephalon, with the axons projecting to the striatum. Prior art methods for treating Parkinson's disease usually involves the use of the drug L-Dopa, to raise dopamine levels in the striatum. However, there are disadvantages with this treatment including drug tolerance and side effects. Also, embryonic tissues that produce dopamine have been transplanted into the striatum of human Parkinsonian patients with reasonable success. However, the use of large quantities of fetal human tissue required for this procedure raises serious ethical concerns and practical issues.

The methods and compositions of the present invention provide an alternative to the use of drugs and the controversial use of large quantities of embryonic tissue for treatment of Parkinson's disease. Dopamine cells can be generated in the striatum by the administration of a composition comprising growth factors to the lateral ventricle. A particularly preferred composition comprises a combination of EGF, FGF-2, and heparan sulphate. The composition preferably also comprises serum. After administration of this composition, there is a significant increase in the transcription of messenger RNA (mRNA) for TH in the subventricular region of the striatum, an area which normally does not contain dopaminergic cell bodies. These methods and results are described in detail in Example 34. As detailed in Example 35, the use of dual labeling tissue to show the distribution of BrdU+ and TH+ cells indicates that, in response to the in vivo administration of growth factors, TH+ cell bodies occur in striatal tissue. Many of these newly generated TH+ cells are also BrdU+.

For the treatment of MS and other demyelinating or hypomyelinating disorders, and for the treatment of Amyotrophic Lateral Sclerosis or other motor neuron diseases, growth factors or other neurological agents would be delivered to the central canal.

In addition to treating CNS tissue immediately surrounding a ventricle, a viral vector, DNA, growth factor, or other neurological agent can be easily administered to the lumbar cistern for circulation throughout the CNS.

Under normal conditions subependymal precursors do not differentiate or migrate, rather, their fate appears to be cell death after an undefined number of cell divisions (Morshead and Van der Kooy, supra). This explanation is also supported by PCR evidence, as described above. Injection of growth factors into the lateral ventricle alters this fate. As described in more detail in Example 27 below, retroviruses were injected into the lateral ventricles for six consecutive days. Implanting cannulae attached to EGF-filled osmotic pumps into the lateral ventricles on the same day as (and 1 or 6 days following) retrovirus injection results in an increase in the total number of RV-β-gal labelled cells 6 days later (from an average of 20 cells/brain to 150 cells/brain).

It is known from the PCR experiments described above that 6 days following retroviral injection no cells exist that contain non-expressed retroviral DNA. Thus these results indicate that the EGF-induced increase in β-gal positive cell number is due to the expansion of the clone size of the retrovirally labelled constitutively proliferative population. It is also possible that part of this increase is due to the activation by EGF of a relatively quiescent stem cell.

Interestingly, this expansion of the number of β-gal labelled cells is accompanied by the migration of these cells away from the subependymal medially, laterally, rostrally, and caudally with subsequent differentiation. Thus, infusion of EGF or similar growth factors induces the proliferation, migration and differentiation of neural stem cells and progenitor cells in vivo, and can be used therapeutically to replace neural cells lost due to injury or disease. In a preferred embodiment EGF and FGF are administered together or sequentially.

The normal fate of the constitutively proliferating cell population (i.e. cell death) can be altered by administering Bcl-2 or genetically modifying the cells with the bcl-2 gene. The gene product is known to prevent programmed cell death (apoptosis) in a variety of cell types. Similar to the EGF experiments, a clonal expansion of the constitutively proliferating cell population is achieved following infection with bcl-2.

Other ways of passing the blood-brain barrier include in vivo transfection of neural stem cells and stem cell progeny with expression vectors containing genes that code for growth factors, so that the cells themselves produce the factor. Any useful genetic modification of the cells is within the scope of the present invention. For example, in addition to genetic modification of the cells to express growth factors, the cells may be modified to express other types of neurological agents such as neurotransmitters. Preferably, the genetic modification is performed either by infection of the cells lining ventricular regions with recombinant retroviruses or transfection using methods known in the art including $CaPO_4$ transfection, DEAE-dextran transfection, polybrene transfection, by protoplast fusion, electroporation, lipofection, and the like [see Maniatis et al., supra]. Any method of genetic modification, now known or later developed can be used. With direct DNA transfection, cells could be modified by particle bombardment, receptor mediated delivery, and cationic liposomes. When chimeric gene constructs are used, they generally will contain viral, for example retroviral long terminal repeat (LTR), simian virus 40 (SV40), cytomegalovirus (CMV); or mammalian cell-specific promoters such as those for TH, DBH, phenylethanolamine N-methyltransferase, ChAT, GFAP, NSE, the NF proteins (NF-L, NF-M, NF-H, and the like) that direct the expression of the structural genes encoding the desired protein.

If a retroviral construct is to be used to genetically modify normally quiescent stem cells, then it is preferable to induce the proliferation of these cells using the methods described herein. For example, an osmotic infusion pump could be used to deliver growth factors to the central canal several days prior to infection with the retrovirus. This assures that there will be actively dividing neural stem cells which are susceptible to infection with the retrovirus.

When the genetic modification is for the production of a biologically active substance, the substance will generally be one that is useful for the treatment of a given CNS disorder. For example, it may be desired to genetically modify cells so they secrete a certain growth factor product. Growth factor products useful in the treatment of CNS disorders are listed above. Cells can also be modified in vivo to express a growth factor receptors, neurotransmitters or their receptors, neurotransmitter-synthesizing genes, neuropeptides, and the like, as discussed above.

Any expression vector known in the art can be used to express the growth factor, as long as it has a promoter which is active in the cell, and appropriate termination and polyadenylation signals. These expression vectors include recombinant vaccinia virus vectors including pSC11, or vectors derived various viruses such as from Simian Virus 40 (SV40, i.e. pSV2-dhfr, pSV2neo, pko-neo, pSV2gpt, pSVT7 and pBABY), from Rous Sarcoma Virus (RSV, i.e. pRSVneo), from mouse mammary tumor virus (MMTV, i.e. pMSG), from adenovirus(pMT2), from herpes simplex virus (HSV, i.e. pTK2 and pHyg), from bovine papillomavirus (BPV, i.e. pdBPV and pBV-1MTHA), from Epstein-Barr Virus (EBV, i.e. p205 and pHEBo) or any other eukaryotic expression vector known in the art.

Other methods for providing growth factors to the area of transplantation include the implantation into the brain in proximity to the graft of any device which can provide an infusion of the factor to the surrounding cells.

In Vitro Models of CNS Development, Function and Dysfunction, and Methods for Screening Effects of Drugs on Neural Cells Neural stem cell progeny cultured in vitro can be used for the screening of potential neurologically therapeutic compositions. These compositions can be applied to cells in culture at varying dosages, and the response of the cells monitored for various time periods. Physical characteristics of the cells can be analyzed by observing cell and neurite growth with microscopy. The induction of expression of new or increased levels of proteins such as enzymes, receptors and other cell surface molecules, or of neurotransmitters, amino acids, neuropeptides and biogenic amines can be analyzed with any technique known in the art which can identify the alteration of the level of such molecules. These techniques include immunohistochemistry using antibodies against such molecules, or biochemical analysis. Such biochemical analysis includes protein assays, enzymatic assays, receptor binding assays, enzyme-linked immunosorbant assays (ELISA), electrophoretic analysis, analysis with high performance liquid chromatography (HPLC), Western blots, and radioimmune assays (RIA). Nucleic acid analysis such as Northern blots can be used to examine the levels of mRNA coding for these molecules, or for enzymes which synthesize these molecules.

Alternatively, cells treated with these pharmaceutical compositions can be transplanted into an animal, and their survival, ability to form neuronal connections, and biochemical and immunological characteristics examined as previously described.

For the preparation of CNS models, neural stem cells and stem cell progeny are proliferated using the methods described above. Upon removal of the proliferation-inducing growth factor, proliferation of multipotent neural stem cells ceases. The neurospheres can be differentiated using the methods described above, for example by adhering the neurospheres to a substrate such as poly-ornithine-treated plastic or glass where the precursor cells begin to differentiate into neurons and glial cells. Thus, the proliferation-inducing growth factor acts as an extrinsic signaling molecule that can be added or removed at will to control the extent of proliferation.

When the proliferation-inducing growth factor is removed, the growth-factor responsive stem cell progeny can be co-cultured on a feeder layer. Many types of feeder layers may be used, such as fibroblasts, neurons, astrocytes, oligodendrocytes, tumor cell lines, genetically altered cell lines or any cells or substrate with bioactive properties. The feeder layer generally produces a broader range of phenotypes. In this instance, the feeder layer acts as a substrate and source of both membrane bound and soluble factors that induce and alter the differentiation of the stem cell-generated progeny. Compared to a more inert substance, such as poly-L-ornithine, an astrocyte feeder layer, for example, induces a broader range of neuronal phenotypes as determined by indirect immunocytochemistry at 7 DIV. When differentiated on a poly-L-ornithine coated substrate with 1% FBS, neuronal phenotypes are almost exclusively GABAergic or substance P-ergic. When differentiated on an astrocyte feeder layer, in addition to GABAergic and substance P-ergic neurons, somatostatin, neuropeptide Y (NPY), glutamate and met-enkephalin-containing neurons are present. The astrocytes can be derived from tissue obtained from various brain regions such as the striatum, cortex and spinal cord.

Once the growth factor is removed, the culture medium may contain serum such as 0.5–1.0% FBS. Serum tends to support the differentiation process and enhance cell survival, especially when the differentiating cells are grown at a low density. However, it is possible to culture and differentiate the cells using defined conditions.

Within 1–3 days after removal of the growth factor and placing of the cell in conditions that support differentiation and survival, most or all of the precursor cells begin to lose immunoreactivity for nestin and begin to express antigens specific for neurons, astrocytes or oligodendrocytes. The identification of neurons is confirmed using immunoreactivity for the neuron-specific markers previously mentioned.

The precursor cells described above can be used in methods of determining the effect of a biological agents on neural cells. The term "biological agent" refers to any agent, such as a virus, protein, peptide, amino acid, lipid, carbohydrate, nucleic acid, nucleotide, drug, pro-drug or other substance that may have an effect on neural cells whether such effect is harmful, beneficial, or otherwise. Biological agents that are beneficial to neural cells are referred to herein as "neurological agents", a term which encompasses any biologically or pharmaceutically active substance that may prove potentially useful for the proliferation, differentiation or functioning of CNS cells or treatment of neurological disease or disorder. For example, the term may encompass certain neurotransmitters, neurotransmitter receptors, growth factors, growth factor receptors, and the like, as well as enzymes used in the synthesis of these agents.

Examples of biological agents include growth factors such as FGF-1, FGF-2, EGF and EGF-like ligands, TGFα, IGF-1, NGF, PDGF, and TGFβ; trophic factors such as BDNF, CNTF, and glial-derived neurotrophic factor (GDNF); regulators of intracellular pathways associated with growth factor activity such as phorbol 12-myristate 13-acetate, staurosporine, CGP-41251, tyrphostin, and the like; hormones such as activin and TRH; various proteins and polypeptides such as interleukins, the Bcl-2 gene product, bone morphogenic protein (BMP-2), macrophage inflammatory proteins (MIP-1α, MIP-1β and MIP-2); oligonucleotides such as antisense strands directed, for example, against transcripts for EGF receptors, FGF receptors, and the like; heparin-like molecules such as heparan sulfate; and a variety of other molecules that have an effect on neural stem cells or stem cell progeny including amphiregulin, retinoic acid, and tumor necrosis factor alpha (TNFα).

To determine the effect of a potential biological agent on neural cells, a culture of precursor cells derived from multipotent stem cells can be obtained from normal neural tissue or, alternatively, from a host afflicted with a CNS disease or disorder such as Alzheimer's Disease, Parkinson's Disease, or Down's Syndrome. The choice of culture will depend upon the particular agent being tested and the effects one wishes to achieve. Once the cells are obtained from the desired donor tissue, they are proliferated in vitro in the presence of a proliferation-inducing growth factor.

The ability of various biological agents to increase, decrease or modify in some other way the number and nature of the stem cell progeny proliferated in the presence of EGF or other proliferative factor can be screened on cells proliferated by the methods described in Examples 1–6. For example, it is possible to screen for biological agents that increase the proliferative ability of progenitor cells which would be useful for generating large numbers of cells for transplantation purposes. It is also possible to screen for biological agents which inhibit precursor cell proliferation. In these studies precursor cells are plated in the presence of the biological factor(s) of interest and assayed for the degree of proliferation which occurs. The effects of a biological agent or combination of biological agents on the differentiation and survival of progenitor cells and their progeny can be determined. It is possible to screen neural cells which have already been induced to differentiate prior to the screening. It is also possible to determine the effects of the biological agents on the differentiation process by applying them to precursor cells prior to differentiation. Generally, the biological agent will be solubilized and added to the culture medium at varying concentrations to determine the effect of the agent at each dose. The culture medium may be replenished with the biological agent every couple of days in amounts so as to keep the concentration of the agent somewhat constant.

Changes in proliferation are observed by an increase or decrease in the number of neurospheres that form and/or an increase or decrease in the size of the neurospheres (which is a reflection of the rate of proliferation—determined by the numbers of precursor cells per neurosphere). Thus, the term "regulatory factor" is used herein to refer to a biological factor that has a regulatory effect on the proliferation of stem cells and/or precursor cells. For example, a biological factor would be considered a "regulatory factor" if it increases or decreases the number of stem cells that proliferate in vitro in response to a proliferation-inducing growth factor (such as EGF). Alternatively, the number of stem cells that respond to proliferation-inducing factors may remain the same, but addition of the regulatory factor affects the rate at which the stem cell and stem cell progeny proliferate. A proliferative factor may act as a regulatory factor when used in combination with another proliferative factor. For example, the neurospheres that form in the presence of a combination of bFGF and EGF are significantly larger than the neurospheres that form in the presence of bFGF alone, indicating that the rate of proliferation of stem cells and stem cell progeny is higher.

Other examples of regulatory factors include heparan sulfate, TGFβs, activin, BMP-2, CNTF, retinoic acid, TNFα, MIP-1α, MIP-1β, MIP-2, NGF, PDGF, interleukins, and the Bcl-2 gene product. Antisense molecules that bind to transcripts of proliferative factors and the transcripts for their receptors also regulate stem cell proliferation. Other factors having a regulatory effect on stem cell proliferation include those that interfere with the activation of the c-fos pathway (an intermediate early gene, known to be activated by EGF), including phorbol 12 myristate 13-acetate (PMA; Sigma), which up-regulates the c-fos pathway and staurosporine (Research Biochemical International) and CGP-41251 (Ciba-Geigy), which down regulate c-fos expression and factors, such as tyrphostin [Fallon, D et al., *Mol. Cell Biol.*, 11(5): 2697–2703 (1991)] and the like, which suppress tyrosine kinase activation induced by the binding of EGF to its receptor.

Preferred regulatory factors for increasing the rate at which neural stem cell progeny proliferate in response to FGF are heparan sulfate and EGF. Preferred regulatory factors for decreasing the number of stem cells that respond to proliferative factors are members of the TGFβ family, interleukins, MIPs, PDGF, TNFα, retinoic acid ($10^{-6}$ M) and CNTF. Preferred factors for decreasing the size of neurospheres generated by the proliferative factors are members of the TGFβ family, retinoic acid ($10^{-6}$ M) and CNTF.

The regulatory factors are added to the culture medium at a concentration in the range of about 10 pg/ml to 500 ng/ml, preferably about 1 ng/ml to 100 ng/ml. The most preferred concentration for regulatory factors is about 10 ng/ml. The regulatory factor retinoic acid is prepared from a 1 mM stock solution and used at a final concentration between about 0.01 μM and 100 μM, preferably between about 0.05 to 5 μM. Preferred for reducing the proliferative effects of EGF or bFGF on neurosphere generation is a concentration of about 1 μM of retinoic acid. Antisense strands, can be used at concentrations from about 1 to 25 μM. Preferred is a range of about 2 to about 7 μM. PMA and related molecules, used to increase proliferation, may be used at a concentration of about 1 μg/ml to 500 μg/ml, preferably at a concentration of about 10 μg/ml to 200 μg/ml. The glycosaminoglycan, heparan sulfate, is a ubiquitous component on the surface of mammalian cells known to affect a variety of cellular processes, and which binds to growth factor molecules such as FGF and amphiregulin, thereby promoting the binding of these molecules to their receptors on the surfaces of cells. It can be added to the culture medium in combination with other biological factors, at a concentration of about 1 ng/ml to 1 mg/ml; more preferred is a concentration of about 0.2 μg/ml to 20 μg/ml, most preferred is a concentration of about 2 μg/ml.

Using these screening methods, it is possible to screen for potential drug side-effects on pre- and post-natal CNS cells by testing for the effects of the biological agents on stem cell and progenitor cell proliferation and on progenitor cell differentiation or the survival and function of differentiated CNS cells. The proliferated precursor cells are typically plated at a density of about $5$–$10 \times 10^6$ cells/ml. If it is desired to test the effect of the biological agent on a particular differentiated cell type or a given make-up of cells, the ratio of neurons to glial cells obtained after differentiation can be manipulated by separating the different types of cells. For example, the O4 antibody (available from Boerhinger Mannheim) binds to oligodendrocytes and their precursors. Using a panning procedure, oligodendrocytes are separated out. Astrocytes can be panned out after a binding procedure using the RAN 2 antibody (available from ATCC). Tetanus toxin (available from Boerhinger Mannheim) can be used to select out neurons. By varying the trophic factors added to the culture medium used during differentiation it is possible to intentionally alter the phenotype ratios. Such trophic factors include EGF, FGF, BDNF, CNTF, TGFα, GDNF, and the like. For example, FGF increases the ratio of neurons, and CNTF increases the ratio of oligodendrocytes. Growing the cultures on beds of glial cells obtained from different CNS regions will also affect the course of differentiation as described above. The differentiated cultures remain viable (with phenotype intact) for at least a month.

The effects of the biological agents are identified on the basis of significant difference relative to control cultures with respect to criteria such as the ratios of expressed phenotypes (neurons: glial cells, or neurotransmitters or other markers), cell viability and alterations in gene expression. Physical characteristics of the cells can be analyzed by observing cell and neurite morphology and growth with microscopy. The induction of expression of new or increased levels of proteins such as enzymes, receptors and other cell surface molecules, or of neurotransmitters, amino acids, neuropeptides and biogenic amines can be analyzed with any technique known in the art which can identify the alteration of the level of such molecules. These techniques include immunohistochemistry using antibodies against such molecules, or biochemical analysis. Such biochemical analysis includes protein assays, enzymatic assays, receptor binding assays, enzyme-linked immunosorbant assays (ELISA), electrophoretic analysis, analysis with high performance liquid chromatography (HPLC), Western blots, and radioimmune assays (RIA). Nucleic acid analysis such as Northern blots and PCR can be used to examine the levels of mRNA coding for these molecules, or for enzymes which synthesize these molecules.

The factors involved in the proliferation of stem cells and the proliferation, differentiation and survival of stem cell progeny, and/or their responses to biological agents can be isolated by constructing cDNA libraries from stem cells or stem cell progeny at different stages of their development using techniques known in the art. The libraries from cells at one developmental stage are compared with those of cells at different stages of development to determine the sequence of gene expression during development and to reveal the effects of various biological agents or to reveal new biological agents that alter gene expression in CNS cells. When the libraries are prepared from dysfunctional tissue, genetic factors may be identified that play a role in the cause of dysfunction by comparing the libraries from the dysfunctional tissue with those from normal tissue. This information can be used in the design of therapies to treat the disorders. Additionally, probes can be identified for use in the diagnosis of various genetic disorders or for use in identifying neural cells at a particular stage in development.

Electrophysiological analysis can be used to determine the effects of biological agents on neuronal characteristics such as resting membrane potential, evoked potentials, direction and ionic nature of current flow and the dynamics of ion channels. These measurements can be made using any technique known in the art, including extracellular single unit voltage recording, intracellular voltage recording, voltage clamping and patch clamping. Voltage sensitive dyes and ion sensitive electrodes may also be used.

The following examples are presented in order to more fully illustrate the preferred embodiments of the invention. They should in no way be construed, however, as limiting the scope of the invention, as defined by the appended claims.

EXAMPLE 1

Dissociation of Embryonic Neural Tissue 14-day-old $CD_7$ albino mouse embryos (Charles River) were decapitated and the brain and striata were removed using sterile procedure. Tissue was mechanically dissociated with a fire-polished Pasteur pipette into serum-free medium composed of a 1:1 mixture of Dulbecco's modified Eagle's medium (DMEM) and F-12 nutrient (Gibco). Dissociated cells were centrifuged at 800 r.p.m. for 5 minutes, the supernatant aspirated, and the cells resuspended in DMEM/F-12 medium for counting.

EXAMPLE 2

Dissociation of Adult Neural Tissue

Brain tissue from juvenile and adult mouse brain tissue was removed and dissected into 500 µm sections and immediately transferred into low calcium oxygenated artificial cerebrospinal fluid (low $Ca^{2+}$ aCSF) containing 1.33 mg/ml trypsin, 0.67 mg/ml hyaluronidase, and 0.2 mg/ml kynurenic acid. Tissue was stirred in this solution for 90 minutes at 32° C.–35° C. aCSF was poured off and replaced with fresh oxygenated aCSF for 5 minutes. Tissue was transferred to DMEM/F-12/10% hormone solution containing 0.7 mg/ml ovomucoid and triturated with a fire polished pasteur pipette. Cells were centrifuged at 400 rpm. for 5 minutes, the supernatant aspirated and the pelleted cells resuspended in DMEM/F-12/10% hormone mix.

EXAMPLE 3

Proliferation of Neural Stem Cells on Substrates 2500 cells/cm² prepared as in Example 1 were plated on poly-L-ornithine-coated (15 µg/ml; Siqma) glass coverslips in 24 well Nunclon (0.5 ml/well) culture dishes. The culture medium was a serum-free medium composed of DMEM/F-12 (1:1) including glucose (0.6%), glutamine (2 µM), sodium bicarbonate (3 mM), and HEPES (4-[2hydroxyethyl]-1-piperazineethanesulfonic acid) buffer (5 mM) (all from Sigma except glutamine [Gibco]). A defined hormone mix and salt mixture (Sigma) that included insulin (25 µg/ml), transferrin (100/g/ml), progesterone (20 nM), putrescine (60 µM), and selenium chloride (30 nM) was used in place of serum. Cultures contained the above medium, hereinafter referred to as "Complete Medium" together with 16–20 ng/ml EGF (purified from mouse sub-maxillary, Collaborative Research) or TGFα (human recombinant, Gibco). After 10–14 days in vitro, media (DMEM only plus hormone mixture) and growth factors were replaced. This medium change was repeated every two to four days. The number of surviving cells at 5 days in vitro was determined by incubating the coverslips in 0.4% trypan blue (Gibco) for two minutes, washing with phosphate buffered saline (PBS, pH 7.3) and counting the number of cells that excluded dye with a Nikon Diaphot inverted microscope.

EXAMPLE 4

Proliferation of Embryonic Mouse Neural Stem Cells in Suspension

Dissociated mouse brain cells prepared as in Examples 1 and 2 (at 1×10⁵ cell/ml) were suspended in Complete Medium with 20 ng/ml of EGF or TGFα. Cells were seeded in a T25 culture flask and housed in an incubator at 37° C., 100% humidity, 95% air/5% $CO_2$. Cells began to proliferate within 3–4 days and due to a lack of substrate lifted off the floor of the flask and continued to proliferate in suspension forming clusters of undifferentiated cells, referred to herein as "neurospheres". After 6–7 days in vitro the proliferating clusters (neurospheres) were fed every 2–4 days by gentle centrifugation and resuspension in DMEM with the additives described above.

EXAMPLE 5

Proliferation of Adult Mouse Neural Stem Cells in Suspension

The striata, including the subependymal region, of female, pathogen-free CD1 albino mice [3 to 18 month old; Charles River (CF1 and CF2 strains yielded identical results)] were dissected and hand cut with scissors into 1-mm coronal sections and transferred into aCSF (pH 7.35, approx. 180 mOsmol), aerated with 95% $O_2$–5% $CO_2$ at room temperature. After 15 minutes the tissue sections were transferred to a spinner flask (Bellco Glass) with a magnetic stirrer filled with low-$Ca^{2+}$ aCSF (pH 7.35, approx. 180 mOsmol), aerated with 95% $O_2$–5% $CO_2$ at 32 to 35° C., containing 1.33 mg/ml of trypsin (9000 BAEE units/mg), 0.67 mg/ml of hyaluronidase (2000 units/mg) and 0.2 mg/ml of kynurenic acid. After 90 minutes, tissue sections were transferred to normal aCSF for 5 minutes prior to trituration. Tissue was transferred to DMEM/F-12 (A:1, Gibco) medium containing 0.7 mg/ml ovomucoid (Sigma) and triturated mechanically with a fire-narrowed pasteur pipet. Cells were plated (1000 viable cells per plate) in noncoated 35 mm culture dishes (Costar) containing Complete Medium and EGF [20 ng/ml, purified from mouse sub-maxillary gland (Collaborative Research)] or human recombinant (Gibco/BRL). Cells were allowed to settle for 3–10 minutes after which the medium was aspirated away and fresh DMEM/F-12/hormone mix/EGF was added. After 5–10 days in vitro the number of spheres (neurospheres) were counted in each 35 mm dish.

EXAMPLE 6

Passaging Proliferated Stem Cells

After 6–7 days in vitro, individual cells in the neurospheres from Example 4 were separated by triturating the neurospheres with a fire polished pasteur pipette. Single cells from the dissociated neurospheres were suspended in tissue culture flasks in DMEM/F-12/10% hormone mix together with 20 ng/ml of EGF. A percentage of dissociated cells began to proliferate and formed new neurospheres largely composed of undifferentiated cells. The flasks were shaken well and neurospheres were allowed to settle in the bottom corner of the flask. The neurospheres were then transferred to 50 ml centrifuge tubes and centrifuged at 300 rpm for 5 minutes. The medium was aspirated off, and the neurospheres were resuspended in 1 ml of medium containing EGF. The cells were dissociated with a fire-narrowed pasteur pipette and triturated forty times. 20 microliters of cells were removed for counting and added to 20 microliters of Trypan Blue diluted 1:2. The cells were counted and replated at 50,000 cells/ml. This procedure can be repeated weekly and results in a logarithmic increase in the number of viable cells at each passage. The procedure is continued until the desired number of stem cell progeny is obtained.

EXAMPLE 7

Differentiation of Neural Stem Cell Progeny and Immunocytochemistry

Cells proliferated from Examples 4 and 6 were induced to differentiate by maintaining the cells in the culture flasks in the presence of EGF or TGFα at 20 ng/ml without reinitiating proliferation by dissociation of the neurospheres or by plating on poly-ornithine in the continued presence of EGF or TGFα.

Indirect immunocytochemistry was carried out with cells prepared as in Example 3 which had been cultured for 14–30 days in vitro on glass coverslips. For anti-NSE (or anti-nestin) and anti-GFAP immunocytochemistry, cells were fixed with 4% paraformaldehyde in PBS and 95% ethanol/5% acetic acid, respectively. Following a 30 minute fixation period, coverslips were washed three times (10 minutes each) in PBS (pH=7.3) and then incubated in the primary antiserum (NSE 1:300, nestin 1:1500 or GFAP 1:100) in PBS/10% normal goat serum/0.3% TRITON®-X-100) for two hours at 37 C. Coverslips were washed three times (10 minutes each) in PBS and incubated with secondary antibodies (goat-anti-rabbit-rhodamine for anti-NSE or anti-nestin and goat-anti-mouse-fluorescein for antiGFAP, both at 1:50) for 30 minutes at 37° C. Coverslips were then washed three times (10 minutes each) in PBS, rinsed with water, placed on glass slides and coverslipped using Fluor-save, a mounting medium preferable for use with fluorescein-conjugated antibodies. Fluorescence was detected and photographed with a Nikon Optiphot photomicroscope.

Neural stem cell progeny were also differentiated using the following differentiation paradigms. The neurospheres used for each paradigm were generated as outlined in Examples 4 and 6. All the neurospheres used were passaged at least once prior to their differentiation.

Paradigm 1—Rapid Differentiation of Neurospheres

Six to 8 days after the first passage, the neurospheres were removed and centrifuged at 400 r.p.m. The EGF-containing supernatant was removed and the pellet suspended in EGF-free complete medium containing 1% FBS. Neurospheres (approximately 0.5–1.0×10$^6$ cells/well) were plated on poly-L-ornithine-coated (15 µg/ml) glass coverslips in 24 well Nuclon (1.0 ml/well) culture dishes. After 24 hours in culture, the coverslips were transferred to 12 well (Costar) culture dishes containing complete medium containing 0.5% FBS. The medium was changed every 4–7 days. This differentiation procedure is referred to as the "Rapid Differentiation Paradigm" or RDP.

Paradigm 2—Differentiation of Dissociated Neurospheres

Six to 8 days after the first passage, the neurospheres were removed and centrifuged at 400 r.p.m. The EGF-containing media was removed and the pellet was suspended in EGF-free complete medium containing 1% FBS. The neurospheres were mechanically dissociated into single cells with a fire-polished Pasteur pipette and centrifuged at 800 r.p.m. for 5 minutes. Between 0.5×10$^6$ and 1.0×10$^6$ cells were plated on poly-L-ornithine-coated (15 µg/ml) glass coverslips in 24 well Nuclon (1.0 ml/well) culture dishes. The EGF-free culture medium containing 1% FBS was changed every 4–7 days.

Paradigm 3—Differentiation of Single Neurospheres

Neurospheres were washed free of EGF by serial transfers through changes of EGF-free medium. A single neurosphere was plated onto poly-L-ornithine-coated (15 µg/ml) glass coverslips in a 24-well plate. The culture medium used was complete medium with or without 1% FBS. The medium was changed every 4–7 days.

Paradigm 4—Differentiation of Single Dissociated Neurospheres

Neurospheres were washed free of EGF by serial transfers through changes of EGF-free medium. A single neurosphere was mechanically dissociated in a 0.5 ml Eppendorf centrifuge tube and all the cells were plated onto a 35 mm culture dish. Complete medium was used with or without 1% FBS.

Paradigm 5—Differentiation of Neurospheres Co-Cultured with Striatal Astrocytes

Neurospheres, derived from striatal cells as described in Example 1 were labeled with 5-bromodeoxyuridine (BrdU) and washed free of EGF. An astrocyte feeder layer was generated from striatal tissue of postnatal mice (0–24 hours), and plated on poly-L-ornithine-coated glass coverslips in a 24-well culture dish. When the astrocytes were confluent, a dissociated or intact neurosphere was placed on each astrocyte bed. Complete medium was changed after the first 24 hours and then every forty-eight hours. When differentiated on an astrocyte feeder layer, in addition to GABAergic and substance P-ergic neurons, somatostatin, NPY, glutamate and methenkephalin-containing neurons were present.

EXAMPLE 8

Effect of Growth Factors on Neurosphere Differentiation

The effects of CNTF, FGF-2, BDNF, and retinoic acid on neurosphere differentiation were tested using the differentiation paradigms set forth in Example 7.

CNTF

The effect of CNTF was assayed in paradigms 1 and 3. For both paradigms, CNTF was added either at the beginning of the experiment at a concentration of 10 ng/ml or daily at a concentration of 1 ng/ml. In paradigm 1, the addition of CNTF increased the number of NSE-immunoreactive cells in addition to the number of tau-1-immunoreactive cells, suggesting that CNTF has an effect on the proliferation, survival, or differentiation of neurons. Preliminary testing with antibodies recognizing the neurotransmitters GABA and substance P suggest that there is no increase in the number of cells containing these proteins. This suggests that a different neuronal phenotype is being produced.

Three different antibodies directed against O4, galactocerebroside (GalC) and MBP were used to study the effect of CNTF on the oligodendrocytes of paradigm 1. CNTF had no effect on the number of O4(+) cells, but there was an increase in the number of GalC(+) and MBP(+) cells compared with the control. Thus it appears that CNTF plays a role in the maturation of oligodendrocytes.

In one experiment, the neurospheres were differentiated as outlined in paradigm 1 except that serum was never added to the culture medium. While the effect of CNTF on neurons and oligodendrocytes was not as apparent as in the presence of serum, there was an increase in the proliferation of flat, protoplasmic astrocytes. Hence, CNTF will affect astrocyte differentiation in various culture conditions.

In paradigm 3, the addition of CNTF resulted in an increase in the number of NSE(+) cells.

BDNF

The effect of BDNF was tested using Paradigm 3. There was an increase in the number of NSE(+) neurons per neurosphere. Additionally, there was an increase in the neuronal branching and the migration of the neurons away from the sphere.

FGF-2

The effect of FGF-2 was tested using paradigms 2 and 4. In paradigm 2, 20 ng/ml of FGF-2 was added at the beginning of the experiment and cells were stained 7 days later. FGF-2 increased the number of GFAP(+) cells and the number of NSE(+) cells. This suggests that FGF-2 has a proliferative or survival effect on the neurons and astrocytes.

In paradigm 4, 20 ng/ml of FGF-2 was added at the beginning of the experiment and assayed 7–10 days later. FGF-2 induced the proliferation of neural stem cell progeny generated by the EGF-responsive stem cell. It induced two different cell types to divide, neuroblasts and bipotential progenitor cells. The neuroblast produced, on average, 6 neurons while the bipotential cell produced approximately 6 neurons and a number of astrocytes.

In previous studies, it was found that when plated at low density (2500 cells/cm$^2$), addition of EGF up to 7 days in vitro (DIV) could initiate proliferation of the stem cell, but not if applied after 7 DIV. Striatal cells (E14, 2500 cell/cm$^2$) were plated in the absence or presence of 20 ng/ml of FGF-2. After 11 DIV, cultures were washed and medium containing 20 ng/ml of EGF was added. After 4–5 DIV, in cultures that were primed with FGF-2, greater than 70% of the wells examined contained clusters of proliferating cells that developed into colonies with the morphologic and antigenic properties of the EGF-generated cells. Cultures that had not been primed with FGF-2 showed no EGF-responsive proliferation. These findings suggest that the EGF-responsive stem cells possess FGF-2 receptors that regulate its long term survival.

Retinoic Acid

The effect of retinoic acid at $10^{-7}$M was tested using paradigm 1. There was an increase in the number of NSE(+) and tau-1(+) cells, suggesting that retinoic acid increases the number of neurons.

EXAMPLE 9

Proliferation of Embryonic Human Neural Stem Cells and Differentiation of the Neural Stem Cell Progeny With approval of the Research Ethical Committee at the University of Lund and the Ethics Committee at the University of Calgary, nine 8–12 week old human fetuses were obtained by suction abortions. Tissue was dissected and any identifiable brain regions were removed. Within 4–5 days post-dissection, tissue pieces were mechanically dissociated into single cells using the procedure of Example 1 and the number of viable cells was counted. About $0.1 \times 10^6$–$0.5 \times 10^6$ cells were plated in 35 cm$^2$ tissue culture flasks (without substrate pre-treatment) in Complete Medium with 20 ng/ml of human recombinant EGF (Gibco/BRL).

Two to three days after plating the cells, the majority of the viable cells had extended processes and had taken on a neuronal morphology. By seven days in vitro (DIV), the neuronal-like cells began to die and by 14 DIV nearly all of these cells were dead or dying (determined by the absence of processes, irregular membranes and granular cytoplasm). A few of the cells (1%) did not extend any processes or flatten nor did they take on an astrocytic morphology, instead these cells remained rounded and by 5 to 7 DIV began to divide. By 10 to 14 DIV, small clusters of cells, attached to the substrate, were identified. During the next 7 to 10 days (17 to 24 DIV), these small clusters continued to grow in size and many remained attached to the substrate. By 28 to 30 DIV, nearly all the proliferating clusters had lifted off the substrate and were floating in suspension. While floating in suspension, the clusters continued to grow in size and were passaged after they had been in culture for 30 to 40 days using the procedure described in Example 6. EGF-responsive cells began to proliferate after a few DIV and formed floating spheres that were passaged a second time after 30 to 40 DIV.

Thirty to 60 days after passage two or three, 2–3 ml aliquots containing media and pass 2 spheres were taken from the tissue culture flasks and plated onto 35 mm culture dish. Single spheres were placed onto poly-L-ornithine coated glass coverslips in DMEM/F-12/HM medium containing EGF. Spheres immediately attached to the substrate and within the first 24–48 hours cells begin to migrate from the sphere. At 14 DIV cells continued to proliferate and migrate resulting in an increase in the diameter of the transferred sphere. By 30 DIV, a large number of cells had been generated from the original sphere and had migrated at a similar rate from the center producing a concentric circle of associated cells. At the periphery, the majority of the cells were one cell layer thick while closer to the center there were denser regions of cells.

Forebrain regions from eight week old tissue produced no spheres, while spheres were observed from hindbrain tissue in two of the four eight week old samples. For the nine week old fetuses, spheres were generated from forebrain region in two of the four samples and in two of the three hindbrain regions which were received. The twelve week old fetus contained only hindbrain tissue and spheres were produced.

Spheres generated from primary culture or pass 1 spheres were removed from the tissue culture flask, without inducing differentiation, and plated onto poly-L-ornithine coated glass coverslips in DMEM/F-12/HM medium for two hours to allow the spheres to attach to the substrate. Coverslips were removed and processed for indirect immunohistochemistry. Immunostaining with antibodies directed against neurofilaments (168 kDa) or GFAP did not identify any immunoreactive (IR) cells. However, nearly all of the cells were immunoreactive with an antibody that recognizes human nestin.

Thirty to 45 days after being plated onto the poly-L-ornithine coated substrate, cells were fixed and processed for indirect immunocytochemical analysis with antibodies directed against: MAP-2, Tau-1, neurofilament 168 kDA, GABA, substance P (neuronal markers); GFAP (astrocyte marker); O4 and MBP (oligodendrocyte markers). Numerous MAP-2 and Tau-1-IR cell bodies and processes were identified in addition to a large number of Tau-1-IR fibers. While there was no indication of substance P immunoreactivity, GABA-IR cell bodies with long branched processes were seen. Neurofilament-IR cells were strongly IR for GFAP. O4-IR cells with an O-2A morphology and an oligodendrocyte morphology were present. MBP-IR (found on oligodendrocytes) was also seen throughout the cultures.

EXAMPLE 10

Proliferation of Adult Monkey (Rhesus) Neural Stem Cells and Differentiation of the Neural Stem Cell Progeny The conus medularis was removed from an adult male monkey (Rhesus) and hand cut with scissors into 1-mm sections and transferred into artificial cerebrospinal fluid (aCSF) containing 124 mM NaCl, 5 mM KCl, 1.3 mM MgCl$_2$, 2 mM CaCl$_2$, 26 mM NaHCO$_3$, and 10 mM D-glucose (pH 7.35, approx. 280 mOsmol), aerated with 95% O$_2$–5% CO$_2$ at room temperature. After 15 min, the tissue sections were transferred to a spinner flask (Bellco Glass) with a magnetic stirrer filled with low-Ca$^{2+}$ aCSF containing 124 mM NaCl, 5 mM KCl, 3.2 mM MgCl$_2$, 0.1 mM CaCl$_2$, 26 mM NaHCO$_3$, and 10 mM D-glucose (pH 7.35, approx. 280 mOsmol), aerated with 95% O$_2$–5% CO$_2$ at 32 to 35° C., containing 1.33 mg/ml of trypsin (9000 BAEE units/mg), 0.67 mg/ml of hyaluronidase (2000 units/mg) and 0.2 mg/ml of kynurenic acid. After 90 min, tissue sections were transferred to normal aCSF for 5 min prior to trituration. Tissue was transferred to DMEM/F-12 (1:1, Gibco) medium containing 0.7 mg/ml ovomucoid (Sigma) and triturated mechanically with a fire-narrowed pasteur pipet.

Cells were plated (1000 viable cells per plate) in non-coated 35 mm culture dishes (Costar) containing Complete Medium and 20 ng/ml EGF (human recombinant from Gibco/BRL). After 7 to 10 days in culture, floating spheres were transferred with wide-bore pipets onto laminin (15 μg/ml)(Sigma)-coated glass coverslips in 24-well culture dishes. EGF @ 20 ng/ml was added to the medium. Spheres attached to the substrate and cells within the sphere continued to proliferate. After 14 to 21 days in vitro (DIV), the cells were probed by indirect immunocytochemistry for the presence of neuron, astrocytes and oligodendrocytes. All three cell types were identified.

EXAMPLE 11

Proliferation of Adult Human Neural Stem Cells and Differentiation of the Neural Stem Cell Progeny During a routine biopsy, normal tissue was obtained from a 65 year old female patient. The biopsy site was the right frontal lobe, 6 mm from the tip of the frontal/anterior horn of the lateral ventricle. The tissue was dissociated using the procedure outlined in Example 2 and cultured in Complete Medium with EGF and FGF-2 (20 ng/ml of each growth hormone), in T25 flasks (Nunclon). The flasks were examined every 2–3 days for neurosphere formation. Clonally-derived cells were passaged using single sphere dissociation: single neurospheres were triturated 100× in sterile aliquot tubes containing 200 μl of the media/hormone/EGF-FGF-2 solution before culturing in 24- or 96-well plates. First-passage neurospheres were plated on poly-ornithine and laminin coated coverslips and allowed to plate down for 14 days in media/hormone/EGF+FGF-2. Some first passage neurospheres were plated on laminin (20 μg/ml) and poly-ornithine coated coverslips in media/hormone mix for 19 hours, then processed for nestin staining as outlined in Example 7. Nestin staining indicated that the neurospheres, prior to the induction of differentiation (as described below) were nestin positive, indicative of the presence of immature undifferentiated cells.

Pass one human neurospheres were plated on a laminin coated substrate (see above). After 14 days, the cultures received a media change to media/hormone mix plus 1% FBS and were allowed to differentiate for 7 days. Immunocytochemical analysis was then performed to determine different neural phenotypes. The differentiated cells were fixed with 4% paraformaldehyde in PBS for 20 minutes. The coverslips were washed three times (five minutes each) in PBS. For triple label immunocytochemistry, the cells were permeabilized for 5 minutes in 0.3% TRITON®-X in PBS followed by 2 washes with PBS. A first set of primary antibodies, MAP-2 (mouse monoclonal, 1:1000, Boerhinger Mannheim) and GFAP (Rabbit polyclonal, 1:300, BTI), used to determine the presence of neurons and astrocytes respectively, were mixed in 10% normal goat serum in PBS. The cells were incubated at 37° C. for 2 hours and then washed 3 times in PBS. A first set of secondary antibodies, goat anti-mouse rhodamine (Jackson Immuno Research) and goat anti-rabbit FITC (IgG, 1:100 Jackson Immuno Research) were mixed in PBS. The cells were incubated for 30 minutes at 37° C. and then rinsed three times with PBS. The second primary antibody, O4 (mouse monoclonal IgM, 1:10) for oligodendrocytes, was mixed in 10% normal goat serum in PBS. The cells were incubated for 2 hours at 37° C. The second set of secondary goat anti-mouse AMCA IgM (1:100 Jackson Immuno Research) was mixed in PBS and cells were incubated for 30 minutes at 37° C. The cells were then rinsed twice in PBS and then in double distilled water before mounting with Fluorosave.

EXAMPLE 12

Screening for the trkB Receptor on Neural Stem Cell Progeny

The expression of the trk family of neurotrophin receptors in EGF-generated neurospheres was examined by northern blot analysis. Total mRNA was isolated from mouse and rat striatal EGF-generated neurospheres. Both rat and mouse neurospheres expressed high levels of trkB receptor mRNA, but did not express trk nor trkC mRNA. In preliminary experiments, single EGF-generated mouse neurospheres were plated on poly-L-ornithine coated glass coverslips and cultured in the absence or presence of 10 ng/ml of BDNF. When examined after 14–28 days in vitro, neurospheres plated in the presence of BDNF contained NSE(+) cells with extensive and highly branched processes; well-developed NSE(+) cells were not observed in the absence of BDNF. Activation of the trkB receptor on EGF-generated neurospheres may enhance differentiation, survival of and/or neurite outgrowth from newly generated neurons.

EXAMPLE 13

Screening for the GAP-43 Membrane Phosphoprotein on Neural Stem Cell Progeny Growth-associated protein (GAP-43) is a nervous system-specific membrane phosphoprotein which is down-regulated during development. Originally, GAP-43 was thought to be neuron-specific, however, recent reports indicate that this protein may be at least transiently expressed during development in some astrocytes, oligodendrocytes and in Schwann cells. At present, the role of GAP-43 in macroglia is not known. The transient expression of GAP-43 in glial cells generated from the EGF-responsive stem cells derived from embryonic and adult murine striatum was investigated. Glial cell (astrocyte and oligodendrocyte) differentiation was induced by plating neural stem cell progeny in a medium containing 1% FBS with no EGF. The cells were then probed with specific antibodies for GAP-43, nestin, GFAP, O4, and GalC. In order to identify cells expressing GAP-43, the antibodies were pooled in various combinations using dual-label immunofluorescence methods.

During the first two days post plating, there was a low to moderate level of GAP-43 expression in almost all cells (flat, bipolar and stellate), but by 3–4 days post-plating, the level of GAP-43 expression became restricted to the bipolar and stellate cells. At 4 days the majority of GAP-43-expressing cells co-labelled with the oligodendrocyte markers O4 and GalC although GFAP and GAP-43 was co-expressed in a number of cells. At one week post-plating however, essentially all of the GFAP-expressing astrocytes no longer expressed GAP-43 while the majority of the O4 and GalC-expressing cells continued to express GAP-43. At 7–10 days, these oligodendrocytes began to express MBP and lose the expression of GAP-43. The EGF-responsive stem cells may represent a useful model system for the study of the role of GAP-43 in glial and neuronal development.

EXAMPLE 14

Treatment of Neurodegenerative Disease Using Progeny of Human Neural Stem Cells Proliferated In Vitro Cells are obtained from ventral mesencephalic tissue from a human fetus aged 8 weeks following routine suction abortion which is collected into a sterile collection apparatus. A 2×4×1 mm piece of tissue is dissected and dissociated as in Example 1. Neural stem cells are then proliferated as in Example 4. Neural stem cell progeny are used for neurotransplantation into a blood-group matched host with a neurodegenerative disease. Surgery is performed using a BRW computed tomographic (CT) stereotaxic guide. The patient is given local anesthesia suppiemencea with intravenously administered midazolam. The patient undergoes CT scanning to establish the coordinates of the region to receive the transplant. The injection cannula consists of a 17-gauge stainless steel outer cannula with a 19-gauge inner stylet. This is inserted into the brain to the correct coordinates, then removed and replaced with a 19-gauge infusion cannula that has been preloaded with 30 µl of tissue suspension. The cells are slowly infused at a rate of 3 µl/min as the cannula is withdrawn. Multiple stereotactic needle passes are made throughout the area of interest, approximately 4 mm apart. The patient is examined by CT scan postoperatively for hemorrhage or edema. Neurological evaluations are performed at various post-operative intervals, as well as PET scans to determine metabolic activity of the implanted cells.

EXAMPLE 15

Remyelination of Myelin Deficient Rats Using Neural Stem Cell Progeny Proliferated In Vitro Embryonic day 15 (E15) Sprague Dawley rats and E14–15 mice were obtained and the neural tissue was prepared using the methods described in Example 1. The cells were suspended in Complete Medium with 16–20 ng/ml EGF (purified from mouse submaxillary, Collaborative Research) or TGFα (human recombinant, Gibco). The cells were seeded in a T25 culture flask and housed in an incubator at 37° C., 100% humidity, 95% air/5% $CO_2$ and proliferated using the suspension culture method of Example 4. Cells proliferated within 3–4 days and, due to lack of substrate, lifted off the floor of the flask and continued to proliferate in suspension forming neurospheres.

After 6–8 days in vitro (DIV) the neurospheres were removed, centrifuged at 400 r.p.m. for 2–5 minutes, and the pellet mechanically dissociated into individual cells with a fire-polished glass pasteur pipet. Cells were replated in the growth medium where proliferation of the stem cells and formation of new neurospheres was reinitiated.

Litters of first day postnatal myelin deficient rats were anesthetized using ice to produce hypothermia. Myelin deficiency is an X-linked trait and thus only one half of the males in any litter are affected. Therefore, only the males were used for these studies. Once anesthetized, a small rostral to caudal incision was made at the level of the lumbar enlargement. The muscle and connective tissue was removed to expose the vertebral laminae. Using a fine rat tooth forceps, one lamina at the lumbar enlargement was removed and a small cut is made in the dura mater to expose the spinal cord.

A stereotaxic device holding a glass pipet was used to inject a 1 µl aliquot of the cell suspension (approximately 50,000 cells/µl) described above. The suspension is slowly injected into a single site (although more could be done) in the dorsal columns of the spinal cord. As controls, some of the animals were sham-injected with sterile saline. The animals were marked by clipping either toes or ears to distinguish between both experimental groups. Following injection of the cell suspension, the wound was closed using sutures or stainless steel wound clips and the animals were revived by warming on a surgical heating pad and then returned to their mother.

The animals were allowed to survive for two weeks post-injection and were then deeply anesthetized with nembutal (150 mg/kg) and perfused through the left ventricle. The spinal cords were removed and the tissue examined by light and electron microscopy. Patches of myelin were found in the dorsal columns of the recipients of both rat and mouse cells, indicating that neural stem cells isolated from rat and mouse neural tissue can differentiate into oligodendroglia and are capable of myelination in vivo.

Because the myelin deficient rat spinal cord is almost completely devoid of myelin, myelin formed at or near the site of injection is derived from the implanted cells. It is possible that the process of injection will allow for the entry of Schwann cells (myelinating cells of the PNS) into the spinal cord. These cells are capable of forming myelin within the CNS but can be easily distinguished from oligodendrocytes using either light microscopy or immunocytochemistry for CNS myelin elements. There is usually a very small amount of CNS myelin within the myelin deficient rat spinal cord. This myelin can be distinguished from normal donor myelin based on the mutation within the gene for the major CNS myelin protein, proteolipid protein (PLP). The myelin deficient rat myelin is not immunoreactive for PLP while the donor myelin is.

EXAMPLE 16

Remyelination in Human Neuromyelitis Optica

Neuromyelitis optica is a condition involving demyelination of principally the spinal cord and optic nerve. Onset is usually acute and in 50% of the cases death occurs within months. The severity of demyelination as well as lesion sites can be confirmed by magnetic resonance imaging (MRI).

Neural stem cell progeny are prepared from fetal human tissue by the methods of Example 9 or 14. Cells are stereotactically injected into the white matter of the spinal cord in the vicinity of plaques as visualized by MRI. Cells are also injected around the optic nerve as necessary. Booster injections may be performed as required.

EXAMPLE 17

Remyelination in Human Pelizaeus-Merzbacher Disease

Pelizaeus-Merzbacher disease is a condition involving demyelination of the CNS. The severity of demyelination as well as lesion sites can be confirmed by magnetic resonance imaging (MRI).

Neural stem cell progeny are prepared from fetal human tissue by the methods of Examples 9 or 14. Cells are stereotactically injected into the white matter of the spinal cord in the vicinity of plaques as visualized by MRI. Cells are also injected around the optic nerve as necessary. Booster injections may be performed as required.

EXAMPLE 18

Genetic Modification of Neural Stem Cell Progeny

Cells proliferated as in Examples 3 or 4 are transfected with expression vectors containing the genes for the FGF-2 receptor or the NGF receptor. Vector DNA containing the genes are diluted in 0.1× TE (1 mM Tris pH 8.0, 0.1 mM EDTA) to a concentration of 40 µg/ml. 22 µl of the DNA is added to 250 µl of 2×HBS (280 mM NaCl, 10 mM KCl, 1.5 mM $Na_2HPO_4.2H_2O$, 12 mM dextrose, 50 mM HEPES) in a disposable, sterile 5 ml plastic tube. 31 µl of 2 M $CaCl_2$ is added slowly and the mixture is incubated for 30 minutes at room temperature. During this 30 minute incubation, the cells are centrifuged at 800 g for 5 minutes at 4° C. The cells are resuspended in 20 volumes of ice-cold PBS and divided into aliquots of $1 \times 10^7$ cells, which are again centrifuged. Each aliquot of cells is resuspended in 1 ml of the DNA-$CaCl_2$ suspension, and incubated for 20 minutes at room temperature. The cells are then diluted in growth medium and incubated for 6–24 hours at 37° C. in 5%–7% $CO^2$. The cells are again centrifuged, washed in PBS and returned to 10 ml of growth medium for 48 hours.

The transfected neural stem cell progeny are transplanted into a human patient using the procedure described in Example 14, or are used for drug screening procedures as described in the examples below.

EXAMPLE 19

Genetic Modification of Neural Stem Cell Progeny with a Retrovirus Containing the Bacterial B-Galactosidase Gene Neural stem cell progeny were propagated as described in Example 4. A large pass-1 flask of neurospheres (4–5 days old) was shaken to dislodge the spheres from the flask. The flask was spun at 400 r.p.m. for 3–5 minutes. About half of the media was removed without disturbing the neurospheres. The spheres and the remaining media were removed, placed into a Falcon 12 ml centrifuge tube, and spun at 600 r.p.m. for 3–5 minutes. The remaining medium was removed, leaving a few hundred microliters.

A retrovirus which contained the bacterial B-galactosidase gene was packaged and secreted, in a replication-deficient fashion, by the CRE BAG2 cell line produced by C. Cepko. A day after the CRE cells reached confluence, the cells were washed with PBS and the retrovirus was collected in DMEM/F12/HM/20 ng/ml EGF for four days. The virus-containing media was filtered through a 0.45 µm syringe filter. The neurospheres were resuspended in the virus-containing media, transferred to a large flask, and left in an incubator overnight at 37° C. The next day, the contents of the flask were transferred to a 12 ml centrifuge tube and spun at 800 r.p.m. The cells were resuspended in EGF-containing media/HM, dissociated into single cells, and counted. The cells were replated in a large flask at 50,000 cells/ml in a total of 20 mls.

Four days later, transformed cells were selected with G418 at a concentration of 300 µg/ml. Transformed spheres were plated on a poly-ornithine coated glass coverslip in a 24-well plate. After the neurospheres adhered to the plate, the cells were fixed with 0.1% glutaraldehyde for 5 minutes at 4° C. After the cells were fixed, they were washed twice with PBS for 10 minutes. The cells were then washed with 0.1% TRITON® in PBS for 10–15 minutes at room temperature. A 1 mg/ml X-Gal solution was added to each well and incubated overnight at 37° C. After incubation overnight, the cells were washed three times with PBS for 10 minutes each and observed for any reaction products. A positive reaction resulted in a blue color, indicating cells containing the transferred gene.

EXAMPLE 20

Proliferation of Neural Stem Cells from Transgenic Mice

Transgenic mice were produced using standard pronuclear injection of the MBP-lacZ chimeric gene, in which the promoter for MBP directs the expression of E. coli B-galactosidase (lacZ). Transgenic animals were identified by PCR using oligonucleotides specific for lacZ.

Neurospheres were prepared from E15 transgenic mice and DNA negative littermates using the procedures set forth in Example 4. The neurospheres were propagated in the defined culture medium in the presence of 20 ng/ml EGF and were passaged weekly for 35 weeks. For passaging, the neurospheres were harvested, gently centrifuged at 800 RPM, and mechanically dissociated by trituration with a fire-polished Pasteur pipet. At various passages, the cells were induced to differentiate into oligodendrocytes, astrocytes, and neurons by altering the culture conditions. The free-floating stem cell clusters were gently centrifuged, resuspended in the same base defined medium without EGF and with 1% FBS and plated on poly ornithine-treated glass coverslips to promote cell attachment. The clusters attach firmly to the glass, and the cells slow or stop dividing and begin to differentiate.

The identification of various cell types was accomplished using immunofluorescence microscopy with antibodies specific for neurons (MAP-2, NF-L, and NF-M), astrocytes (GFAP) and oligodendrocytes and oligodendrocyte precursors (A2B5, $O_1$, $O_4$, Gal C, and MBP). One to 14 days post-plating, the cells on the coverslips were incubated unfixed, for 30 minutes at room temperature with the primary antibodies O1, O4, GalC, and A2B5 (supernatants) diluted in minimal essential medium with 5% normal goat serum and 25 mM HEPES buffer, pH 7.3 (MEM-HEPES, NGS). Following the primary antibodies, the coverslips were gently washed 5 times in rhodamine-conjugated secondary antibodies (Sigma) diluted in MEM-HEPES, NGS. The coverslips were then washed 5 times in MEM-HEPES and fixed with acid alcohol (5% glacial acetic acid/95% ethanol) at −20° C. The coverslips were then washed 5 times with MEM-HEPES, and either mounted and examined using fluorescence microscopy or immunoreacted with rabbit polyclonal antisera raised against GFAP, nestin, MBP, or proteolipid protein (PLP). When subjected to a second round of immunolabeling, the coverslips were incubated first for 1 hour with 5% normal goat serum (NGS) in 0.1 M phosphate buffer with 0.9% NaCl at pH 7.4 (PBS) and then incubated in rabbit primary antibodies diluted in NGS for 1–2 hours at room temperature. The coverslips were washed 3 times with PBS and then incubated with the appropriate secondary antibody conjugates diluted in NGS, washed again with PBS and then finally mounted on glass microscope slides with Citifluor antifadent mounting medium and examined using a fluorescence microscope. In cases were they were not incubated first with the monoclonal antibody supernatants, the coverslips were fixed for 20 minutes with 4% paraformaldehyde in PBS (pH 7.4), washed with PBS, permeabilized with 100% ethanol, washed again with PBS and incubated with 5% NGS in PBS for 1 hour. The primary antibodies and secondary antibody conjugates were applied as outlined above.

The neural stem cells derived from the transgenic animals were indistinguishable from non transgenic stem cells in their potential for differentiation into neurons, astrocytes, and oligodendrocytes. The MBP promoter directed the expression of the B-galactosidase reporter gene in a cell-specific and developmentally appropriate fashion. The transgene expression is highly stable as oligodendrocytes derived from late passage MBP-lacZ neurospheres (20 passages), expressed the B-galactosidase gene. Thus, transgenically marked neurospheres are likely to be an excellent source of cells for glial cell transplantation.

EXAMPLE 21

Genetic Modification of Neural Stem Cell Progeny Using Calcium Phosphate Transfection Neural stem cell progeny are propagated as described in Example 4. The cells are then infected using a calcium phosphate transfection technique. For standard calcium phosphate transfection, the cells are mechanically dissociated into a single cell suspension and plated on tissue culture-treated dishes at 50% confluence (50,000–75,000 cells/cm$^2$) and allowed to attach overnight.

The modified calcium phosphate transfection procedure is performed as follows: DNA (15–25 µg) in sterile TE buffer (10 mM Tris, 0.25 mM EDTA, pH 7.5) diluted to 440 µl with TE, and 60 µl of 2 M CaCl$_2$ (pH to 5.8 with 1 M HEPES buffer) is added to the DNA/TE buffer. A total of 500 µl of 2× HeBS (HEPES-Buffered saline; 275 mM NaCl, 10 mM KCl, 1.4 mM Na$_2$HPO$_4$, 12 mM dextrose, 40 mM HEPES buffer powder, pH 6.92) is added dropwise to this mix. The mixture is allowed to stand at room temperature for 20 minutes. The cells are washed briefly with 1×HeBS and 1 ml of the calcium phosphate precipitated DNA solution is added to each plate, and the cells are incubated at 37° for 20 minutes. Following this incubation, 10 mls of complete medium is added to the cells, and the plates are placed in an incubator (37° C., 9.5% CO$_2$) for an additional 3–6 hours. The DNA and the medium are removed by aspiration at the end of the incubation period, and the cells are washed 3 times with complete growth medium and then returned to the incubator.

EXAMPLE 22

Genetically Modified Neural Stem Cell Progeny Expressing NGF

Using either the recombinant retrovirus or direct DNA transfection technique, a chimeric gene composed of the human CMV promoter directing the expression of the rat NGF gene is introduced into the neurosphere cells. In addition, the vector includes the *E. coli* neomycin resistance gene driven off of a viral promoter. After 2 weeks of G418 selection, the cells are cloned using limiting dilution in 96-multi-well plates and the resulting clones are assayed for neurotrophin protein expression using a neurotrophin receptor (trk family) autophosphorylation bioassay.

Clones expressing high levels of NGF are expanded in T-flasks prior to differentiation. The cells are then removed from the EGF-containing complete medium and treated with a combination of serum and a cocktail of growth factors to induce astrocyte differentiation. The astrocytes are again assayed for NGF expression to ensure that the differentiated cells continue to express the trophic factors. Astrocytes that secrete NGF are then injected into fimbria/fornix lesioned rat brains immediately post-lesioning in order to protect the cholinergic neurons. Control astrocytes that do not secrete NGF are injected into similarly lesioned animals. The sparing of cholinergic neurons in the lesion model is assessed using immunocytochemistry for ChAT, the marker for these cholinergic neurons.

EXAMPLE 23

Genetically Modified Neural Stem Cell Progeny Expressing CGAT

Recently, a novel chromaffin granule amine transporter (CGAT) cDNA has been described by Liu et al. (*Cell* 70:539–551 (1992)), which affords resistance to the neurotoxin MPP+ in Chinese hamster ovary (CHO) cells in vitro. Because dopaminergic neurons from the substantia nigra are specifically killed by MPP+, CGAT gene expression in genetically modified neural stem cell progeny may improve viability of the cells after they are implanted into the Parkinsonian brain. Neural stem cell progeny are propagated as in Example 4. The cells are mechanically dissociated and plated on plastic dishes and infected with a retrovirus containing the CGAT cDNA. The expression of the CGAT cDNA (Liu et al. supra) is directed by a constitutive promoter (CMV or SV40, or a retroviral LTR) or a cell-specific promoter (TH or other dopaminergic or catecholaminergic cell-specific regulatory element or the like). The cells are screened for the expression of the CGAT protein. Selected cells can then be differentiated in vitro using a growth factor or a combination of growth factors to produce dopaminergic or pre-dopaminergic neurons.

EXAMPLE 24

3H-Thymidine Kill Studies Identify Presence of Constitutively Proliferating Population of Neural Cells in Subependymal Region Adult male CD1 mice received a series of intraperitoneal injections of 3H-thymidine (0.8 ml per injection, specific activity 45–55 mCi/mmole, ICN Biomedical) on day 0 (3 injections, 1 every 4 hours) in order to kill the constitutively proliferating subependymal cells. On day 0.5, 1, 2, 4, 6, 8 or 12, animals received 2 BrdU injections 1 hour apart (see Example 25) and were sacrificed 0.5 hour after the last injection.

It was observed that 10% of the cells were proliferating on day 1 post-kill, and by 8 days the number of proliferating cells had reached 85%, which was not statistically significantly different from control values. Animals were sacrificed and the brains were removed and processed as described in Example 10.

In a second group of animals, 3H-thymidine injections were given on day 0 (3 injections, 1 every 4 hours), followed by an identical series of injections on day 2 or 4. Animals were allowed to survive for 8 days following the second series of injections (days 9, 10 and 12 respectively) at which time they received 2 injections of BrdU and were sacrificed 0.5 hours later. Animals were sacrificed and the brains were removed and processed as described in Example 25.

After the second series of injections on day 2 only 45% of the proliferating population had returned relative to control values. This indicates that the second series of injections given on day 2 had killed the stem cells as they were recruited to the proliferating mode. The second series of injections given on day 4 resulted in a return to control values by day 8 suggesting that by this time, the stem cells were no longer proliferating and hence were not killed by the day 4 series of injections.

EXAMPLE 25

BrdU Labeling Studies Identify Presence of Constitutively Proliferating Population of Neural Cells in Subependymal Region Adult male CD1 mice (25–30 g, Charles River) were injected intraperitoneally (i.p.) with bromodeoxyuridine (BrdU, Sigma, 65 mg/kg) every 2 hours for a total of 5 injections in order to label all of the constitutively proliferating cells in the subependyma lining the lateral ventricles in the forebrain. One month later, animals were sacrificed with an overdose of sodium pentobarbital and transcardially perfused using 4% paraformaldehyde. The brains were removed and post-fixed overnight in 4% paraformaldehyde with 20% sucrose. Brain sections were cut on a cryostat (30 μm) and collected in a washing buffer [0.1 M phosphate buffered saline (PBS) pH 7.2 with 1% normal horse serum and 0.3% TRITON® X-100]. Sections were incubated in 1M HCl at 60° C. for 0.5 hours then washed 3 times (10 minutes each) in washing buffer. Following the final wash, sections were incubated in anti-BrdU (Becton Dickinson, 1:25) for 45 hours at 4° C. After incubation in the primary antibody, sections were washed 3 times and incubated for 1 hours in biotinylated horse-anti-mouse secondary antibody (Dimension Lab, 1:50) at room temperature followed by another 3 washes. The sections were then incubated for 1 hour in avidin conjugated FITC (Dimension Lab, 1:50) at room temperature and washed a final 3 times. Sections were mounted on gelatin coated slides, air-dried and coverslipped with Fluoromount. Slides were examined for BrdU positive cells using a NIKON fluorescent microscope. The number of BrdU positive cells was counted within the subependyma surrounding the lateral ventricles in 8 samples in sections between the closing of the corpus callosum rostrally and the crossing of the anterior commissure caudally. It was found that 31 days following the series of BrdU injections, 3% of the subependymal cells were still labeled compared to control animals sacrificed immediately following the series of injections (control 100%).

EXAMPLE 26

3H-Thymidine Kill Studies Identify Presence of Relatively Quiescent Neural Stem Cells in Subependymal Region Adult male CD1 mice were divided into 4 groups. Group A animals received a series of 3H-thymidine injections on day 0 (3 injections, 1 every 4 hours). Animals in groups B and C received a series of 3H-thymidine injections on day 0 followed by a second series of injections on day 2 or 4. Group D animals received injections of physiological saline instead of 3H-thymidine over the same time course as group A. Animals from all groups were sacrificed by cervical dislocation 16–20 hours following the last series of injections. Brains were removed and neural tissue obtained from the subependyma surrounding the lateral ventricles in the forebrain was dissociated and the neural cells cultured as described in Example 5. At 6 and 8 days in vitro, the total number of spheres was counted in each of the 35 mm wells.

Control animals that received a series of saline injections formed the same number of spheres as animals that received 3H-thymidine on day 0 (which kills the normally proliferating subependymal cells). This indicates that the constitutively proliferating subependymal cells are not the source of stem cells isolated in vitro. Animals that received a second series of injections on day 2 formed 45% the number of spheres (similar to the number of proliferating subependymal cells observed in vivo). When a second series of injections was done on day 4, the number of spheres formed in vitro was not significantly different from control values, again correlating with the in vivo findings. Taken together, this data indicates that the multipotent spheres, which are isolated in vitro in the presence of EGF, are formed from the relatively quiescent stem cell population within the subependyma in vivo.

EXAMPLE 27

In Vivo Proliferation of Neural Stem Cells of Lateral Ventricle

A replication incompetent retrovirus containing the β-galactosidase gene [as described in Walsh and Cepko, *Science* 241:1342, (1988)] was injected into the forebrain lateral ventricles of CD1 adult male mice (25–30 g from Charles River). The injected retrovirus was harvested from the BAG cell line (ATCC CRL-9560) according to the method of Walsh and Cepko (supra). Mice were anesthetized using 65 mg/kg, i.p. sodium pentobarbital. Unilateral stereotactic injections of 0.2–1.0 μl of retrovirus were injected into the lateral ventricle using a 1 μl Hamilton syringe. The coordinates for injection were AP +4.2 mm anterior to lambda, L±0.7 mm, and DV −2.3 mm below dura, with the mouth bar at −2 mm below the interaural line.

On the same day as, one day, or six days following the retrovirus injection, an infusion cannulae attached to a 0.5 μl/hour ALZET osmotic mini-pumps filled with 3.3–330 μg/ml of EGF were surgically implanted into the lateral ventricles at the identical stereotactic coordinates as stated above. The infusion cannula kits were obtained from ALZA. The infusion cannulae were cut to 2.7 mm below the pedestal. The pumps were secured to the mouse skull by use of acrylic cement and a skull screw contralateral and caudal to the injection site. The osmotic mini-pump was situated subcutaneously under and behind the armpit of the left front paw and connected to the infusion cannula by the means of polyethylene tubing.

Six days following initiation of EGF infusion the animals were sacrificed with an overdose of sodium pentobarbital. Mice were transcardially perfused with 2% buffered paraformaldehyde, and the brains were excised and post fixed overnight with 20% sucrose in 2% buffered paraformaldehyde. Coronal slices were prepared with −20 celsius cryostat sectioning at 30 μm. Slices were developed for β-gal histochemistry as per Morshead and Van der Kooy (supra).

Under these conditions, regardless of the day post retrovirus injection, infusion of EGF resulted in an expansion of the population of β-gal labelled cells from an average of 20 cells per brain up to an average of 150 cells per brain and the migration of these cells away from the lining of the lateral ventricles. Infusion of FGF-2 at 33/g/ml resulted in an increase in the number of β-gal labelled cells, but this increase was not accompanied by any additional migration. Infusion of EGF and FGF together resulted in an even greater expansion of the population of β-gal labelled cells from 20 cells per brain to an average of 350 cells per brain.

These results indicate that FGF may be a survival factor for relatively quiescent stem cells in the subependyma layer, whereas EGF may act as a survival factor for the normally dying progeny of the constitutively proliferating population. The synergistic increase in β-galactosidase cell number when EGF and FGF are infused together further reflects the direct association between the relatively quiescent stem cell and the constitutively proliferating progenitor cell.

EXAMPLE 28

In Vivo Proliferation of Neural Stem Cells of the Third and Fourth Ventricles and the Central Canal A retroviral construct containing the β-galactosidase gene is microinjected (as in Example 27) into the III ventricle of the diencephalon, IV ventricle of the brain stem and central canal of the spinal cord. Minipumps containing EGF and FGF are then used to continuously administer growth factors for six days (as in Example 27) into the same portion of the ventricular system that the retroviral construct was administered. This produces an increase in the number of β-galactosidase producing cells which survive and migrate out into the tissue near the III ventricle, IV ventricle and central canal of the spinal cord forming new neurons and glia.

EXAMPLE 29

In Vivo Modification and Proliferation of Neural Stem Cells and Differentiation of Neural Stem Cell Progeny of the Lateral Ventricle A retroviral construct containing the TH gene as well as the β-galactosidase gene is microinjected into the adult lateral ventricle as in Example 27. Minipumps containing EGF, FGF, or EGF and FGF together are then used to continuously administer the growth factor(s) into the lateral ventricle for 6 days as in Example 27. As the infected subependymal cells migrate out into the striatum they differentiate into neuronal cells that produce dopamine as measured directly by immunofluorescence with an antibody and (from a direct functional assay) by the ability to overcome the rotational bias produced by unilateral 6-hydroxydopamine lesions.

EXAMPLE 30

In Vivo Infusion of Growth Factors into Ventricles to Obtain Elevated Numbers of Neural Stem Cells Adult male $CD_1$ albino mice (30–35 g) from Charles River were anaesthetized with sodium pentobarbital (0.40 mL of a 10% solution) and placed in a stereotaxic apparatus. The dorsal aspect of the skull was exposed with a longitudinal incision. Cannulas were inserted into the fourth ventricle (stereotaxic coordinates A/P −7.0, L±0.3 D/V −5.8), cerebral aqueduct (A/P −4.8 L±D/V −2.6), or central canal (D/V −1.5). The cannulae were attached with sterile tubing to subcutaneous positioned ALZET osmotic mini-pumps containing 25 μg/mL EGF (Becton 40001) and/or 25 μg/mL FGF-2 (R&D Systems 233-FB). Pumps containing sterile saline plus 0.1% mouse albumin (Sigma A3134) were used as controls. The incisions were closed with dental cement.

Six days following surgery mice were injected with 0.15 mL BrdU (Sigma B5002); 18 mg/mL in 0.007% NaOH/ 0.1M PBS) every 2 hours for 8 hours. They were killed 0.5 hours after the last injection with an anaesthetic overdose, and transcardially perfused with 10 mL of ice-cold sterile saline followed by 10 mL of ice-cold Bouin's fixative (5% glacial acetic acid, 9% formaldehyde, 70% picric acid). The cervical spinal cord region was dissected out and post-fixed overnight at 4° C. in Bouin's post-fixative solution (9% formaldehyde, 70% picric acid). The following day the tissue was cryoprotected by immersion in 10% sucrose for 2 hours, 20% sucrose for 2 hours, and 30% sucrose overnight. The tissue was frozen in powdered dry ice, mounted in Tissue-Tek (Miles 4583) at −18° C., and 30 μm serial sagittal sections were mounted onto gel-subbed glass slides. Each slide also contained one or more 30 μm coronal sections through the lateral ventricles from the brain of the same animal to serve as a positive control. Slides were kept at −80° C. until processed. *Immunohistochemistry*: Slides were rinsed in PBS 3×15 minutes in 0.1M PBS at room temperature, hydrolyzed with 1 N HCl for 60 minutes at 37° C., rinsed for 3×15 minutes in 0.1M PBS at room temperature, placed in 6% $H_2O_2$ in methanol for 30 minutes at room temperature, rinsed for 3×15 minutes in 0.1M PBS at room temperature, and incubated in 10% normal horse serum (Sigma H-0146) in 0.1M PBS or 20 minutes at room temperature. Slides were incubated overnight at room temperature in anti-BrdU monoclonal antibody (Becton 7580) that was diluted 1:50 in 0.1M PBS containing 1.5% normal horse serum and 0.3% TRITON®. The following day the slides were rinsed in PBS for 3×10 minutes in 0.1M PBS at room temperature, incubated with biotinylated horse anti-mouse IgG (Vector BA-2000) for 2 hours at room temperature, rinsed for 3×15 minutes in 0.1M PBS at room temperature, incubated in ABC reagent (Vector PK-6100) for 2 hours at room temperature, rinsed for 3×15 minutes in 0.1M PBS at room temperature, and developed with DAB reagent for 2 to 4 minutes. The slides were coverslipped with Aqua Polymount (Polysciences 18606). The number of BrdU positive cells was counted per cervical spinal cord section. Some BrdU labelled cells were found in the saline control sections. Treatment with either EGF or FGF-2 resulted in a significant increase in the number of BrdU labelled cells seen compared to control. The combination of EGF plus FGF-2 produced even a greater amount of BrdU positive cells per section.

EXAMPLE 31

In Vivo Infusion of Growth Factors into Ventricles to Increase Yield of Neural Stem Cells that Proliferate In Vitro EGF pumps were implanted as described in Example 27. Animals were sacrificed by cervical dislocation 6 days after the pump was implanted. Brains were removed and the stem cells isolated and counted as described in Example 5.

Animals infused with EGF into the lateral ventricles for 6 days prior to sacrifice and brain culturing had 4 times as many spheres forming after 9 days in vitro compared to control animals which received saline pumps for the same 6 day period. Thus, infusing EGF into the lateral ventricles in vivo prior to removal and dissociation of neural tissue, greatly increases the yield of stem cells which proliferate and form neurospheres in vitro.

EGF and FGF can be infused into the ventricles to further increase the yield of neural stem cells obtainable from the neural tissue. Neurospheres generated by this method are used as a source of donor cells for later transplantation into degenerated areas of human adult CNS. Neurospheres can also be proliferated accordingly from a patient's own CNS stem cells and transplanted back into the patient.

EXAMPLE 32

In Vivo Modification of Neural Cells with bcl-2 Gene

A retroviral construct containing the human bcl-2 gene and the β-galactosidase gene is microinjected into the adult mouse lateral ventricle. A control mouse is injected with a retroviral construct containing only the β-galactosidase gene. One of the two progeny of each of the constitutively proliferating subependymal cells of the adult lateral ventricle normally dies within a few hours after division. The bcl-2 gene product prevents the programmed death of cells in several other tissues. In the adult subependyma, single cells infected with both the β-galactosidase and bcl-2 genes are marked by expression of both these gene products. These cells are identified in brain tissue slices with antibodies specific to β-galactosidase and human Bcl-2. Proliferating infected subependymal cells so infected produce larger numbers of cells per clone relative to the control. Thus, Bcl-2 induces the survival of the one normally dying progeny of each division of a constitutively proliferating adult subependymal cell. Moreover, the bcl-2 infected progeny migrate out into striatal and septal tissue to produce new neurons and glia. This indicates that EGF and Bcl-2 act as a survival factors for the normally dying progeny of constitutively proliferating adult subependymal cells which generate new neurons and glia in vivo.

EXAMPLE 33

In Vivo Modification of Neural Cells with NGF Gene

A retroviral construct containing the NGF gene is microinjected using the procedure described in Example 24 to infect the constitutively proliferating adult subependymal cells of the lateral ventricle. Thus, these cells are used to produce an endogenous growth factor in the adult brain. Levels of NGF produced by the transfected cells are measured directly by radioimmunoassay and (from a direct functional assay) by rescue of basal forebrain cholinergic neurons in vivo after axotomy injury in the model developed by Gage and collaborators (P.N.A.S. 83:9231, 1986).

EXAMPLE 34

Generation of Dopamine Cells in the Striatum by the Administration of a Composition Comprising Growth Factors to the Lateral Ventricle Adult male $CD_1$ mice were anesthetized and placed in a stereotaxic apparatus. A cannula, attached to an ALZET minipump, was implanted into a lateral ventricle of each animal. The minipumps were subcutaneously implanted and were used to deliver (a) conditioned medium (from the rat B49 glial cell line, obtained from D Schubert, Salk Institute) plus bFGF (R&D Systems, 25 μg/ml) plus heparan sulfate (Sigma, 10 IU/ml) (CMF) or (b) EGF (Chiron, 25 μg/ml) plus bFGF (25 μg/ml) plus heparan sulfate (10 IU/ml) plus 25% FBS (E+F+FBS) or (c) sterile saline solution (SAL) as a control, into the lateral ventricles. Once batch of animals was sacrificed one day after completion of the delivery regimen and the others were sacrificed twenty days later. The subventricular zones (SVZs) of these mice were dissected out, separating the cannulated, and therefore treated, side from the non-cannulated control sides. The substantia nigra (SN) region of these mice were also recovered. Total RNA was extracted from these tissues using the guanidium thiocyanate acid phenol method [Chomzynski and Sacchi, Annal. Biochem. 162: 156–159, (1987)]. The RNA was then reverse transcribed to produce cDNA.

These cDNAs were subject to PCR using primers designed to bracket a 254 nucleotide region of the TH messenger RNA (mRNA) and thermal cycling conditions favoring quantitative amplification. The PCR products were electrophoresed on a 2% agarose gel and then capillary blotted onto a positively charged nylon membrane. Radioactively labelled cDNA probe to TH was hybridized to the filter and detected by autoradiography. The autoradiograph was scanned and analyzed by densitometry to obtain relative levels of mRNA for TH in the SVZs of the cannulated sides in response to the treatments in the non-cannulated control SVZs and in the SN. In animals analyzed one day after treatment, the administration of E+F+FBS produced an eleven-fold increase in the level of TH mRNA in the SVZ compared to that observed in response to CMF, which in turn was more than twice the level seen with SAL. Twenty one days after treatment, the amount of TH mRNA detected in response to treatment with E+F+FBS was approximately the same as that detected after one day, while CMF and SAL treated SVZs had TH mRNA levels which were below detectable limits and were indistinguishable from the non-cannulated SVZ controls. Under all treatments, the SN had measurable amounts of TH mRNA.

EXAMPLE 35

Detection of Dopaminergic Cells in Striatal Tissue Using Dual Labeling

Male $CD_1$ mice (Charles River, approximately 4 to 6 weeks old) were given intraperitoneal injections of BrdU (Sigma, 120 mg/kg) at 2 hour intervals over a 24 hour period, in order to label mitotically active cells. A cannula attached to an ALZET minipump was then implanted unilaterally into a lateral ventricle of each animal in order to deliver compositions a–c (CMF, E+F+FBS, or sterile saline) described in Example 34.

Animals were sacrificed 24 hours after the administration of growth factors using a lethal dose of pentobarbital anesthetic. The animals were then perfused through the heart with 10 ml of ice could 4% paraformaldehyde solution. The brains were removed and tissue in the region extending from the olfactory bulb to the third ventricle, including the striatum, was dissected out and stored overnight at 4° C. in a 30% sucrose/4% paraformaldehyde solution. The tissue was then frozen on dry ice and kept at −70° C. until processed. 30 μm coronal sections were cut using a cryostat and the sections were placed in 12 well porcelain dishes, to which 400 μl of PBS had been added. Sections were rinsed with fresh PBS and incubated overnight with the following primary antibodies: anti-TH (rabbit polyclonal, 1:1000, Eugene Tech International Inc.; or 1:100, Pel-freeze) and mouse anti-BrdU (1:55, Amersham), prepared in PBS/10% normal goat serum/0.3 TRITON®-100. Following three rinses in PBS, goat anti-rabbit rhodamine and goat anti-mouse fluorescein (Jackson) were applied in PBS for 50 minutes at room temperature. Sections were then washed three times (10 minutes each) in PBS, placed on glass slides, dried and then coverslipped using Fluorsave (Calbiochem #345789).

The location of dopaminergic neurons was determined by mapping the location of TH-immunoreactive (TH+) cells, or TH+ and BrdU+ cells in relation to the ventricles. In response to saline injections made into the lateral ventricles, the normal population of TH+ fibers were detected in the striatum but no TH+ cell bodies were detected in this region. CMF treatment resulted in the detection of TH+ cell bodies, in addition to the normal population of TH+ fibers, in the striatum and in the region of the third ventricle. E+F+FBS treatment had the most profound effect resulting in the detection of the most TH+ cell bodies. Several of the TH+ cell bodies were also BrdU positive.

EXAMPLE 36

Rat Model of Parkinson's Disease Measures the Effects of In Vivo Administration of Growth Factors The 6-OHDA lesion rat model of Parkinson's disease is used to measure the effects of administering various combinations of growth factors to the lateral ventricle. Unilateral 6-OHDA lesions are performed in the rat model and rotation behavior is observed. Minipumps are subcutaneously implanted into the animals as described in Example 34. EGF (Chiron, 25 µg/ml) plus bFGF (25 µg/ml) plus heparan sulfate (10 IU/ml) plus 25% FBS is continuously administered to the lateral ventricle. Saline is administered to control animals. The ability to overcome the rotational bias produced by the unilateral 6-OHDA lesions is observed.

EXAMPLE 37

Screening of Drugs or Other Biological Agents for Effects on Multipotent Neural Stem Cells and Neural Stem Cell Progeny A. Effects of BDNF on Neuronal and Glial Cell Differentiation and Survival Precursor cells were propagated as described in Example 4 and differentiated using Paradigm 3 described in Example 7. At the time of plating the EGF-generated cells, BDNF was added at a concentration of 10 ng/ml. At 3, 7, 14, and 21 days in vitro (DIV), cells were processed for indirect immunocytochemistry. BrdU labeling was used to monitor proliferation of the precursor cells. The effects of BDNF on neurons, oligodendrocytes and astrocytes were assayed by probing the cultures with antibodies that recognize antigens found on neurons (MAP-2, NSE, NF), oligodendrocytes (O4, GalC, MBP) or astrocytes (GFAP). Cell survival was determined by counting the number of immunoreactive cells at each time point and morphological observations were made. BDNF significantly increased the differentiation and survival of neurons over the number observed under control conditions. Astrocyte and oligodendrocyte numbers were not significantly altered from control values.

B. Effects of BDNF on the Differentiation of Neural Phenotypes

Cells treated with BDNF according to the methods described in Part A were probed with antibodies that recognize neural transmitters or enzymes involved in the synthesis of neural transmitters. These included TH, ChAT, substance P, GABA, somatostatin, and glutamate. In both control and BDNF-treated culture conditions, neurons tested positive for the presence of substance P and GABA. As well as an increase in numbers, neurons grown in BDNF showed a dramatic increase in neurite extension and branching when compared with control examples.

C. Identification of Growth-Factor Responsive Cells

Cells that are responsive to growth factor treatment were identified by differentiating the EGF-generated progeny as described in Example 7, paradigm 3 and at 1 DIV adding approximately 100 ng/ml of BDNF. At 1, 3, 6, 12 and 24 hours after the addition of BDNF the cells were fixed and processed for dual label immunocytochemistry. Antibodies that recognize neurons (MAP-2, NSE, NF), oligodendrocytes (O4, GalC, MBP) or astrocytes (GFAP) were used in combination with an antibody that recognizes c-fos and/or other immediate early genes. Exposure to BDNF results in a selective increase in the expression of c-fos in neuronal cells.

D. Effects of BDNF on the Expression of Markers and Regulatory Factors During Proliferation and Differentiation Cells treated with BDNF according to the methods described in Part A are processed for analysis of the expression of FGF-R1, as described in Example 39 or other markers and regulatory factors, as described in Example 40.

E. Effects of BDNF Administration During Differentiation on the Electrophysiological Properties of Neurons Neurons treated with BDNF during differentiation, according to the methods described in Part A, are processed for the determination of their electrophysiological properties, as described in Example 41.

F. Effects of Chlorpromazine on the Proliferation, Differentiation, and Survival of Growth Factor Generated Stem Cell Progeny Chlorpromazine, a drug widely used in the treatment of psychiatric illness, is used in concentrations ranging from 10 ng/ml to 1000 ng/ml in place of BDNF in Examples 7A to 7E above. The effects of the drug at various concentrations on stem cell proliferation and on stem cell progeny differentiation and survival is monitored. Alterations in gene expression and electrophysiological properties of differentiated neurons are determined.

EXAMPLE 38

Stem Cell Proliferation Assay

Primary cells were obtained from E14 mice and prepared as detailed in Examples 1 and 4. Either EGF, EGF and FGF or EGF and BMP-2 were added to complete medium at a concentration of 20 ng/ml of each growth factor, with the exception of BMP-2 which was added at a concentration of 10 ng/ml. Cells were diluted with one of the prepared growth factor-containing media to a concentration of 25,000 cells/ml. 200 µl of the cell/medium combination were pipetted into each well of a 96-well place (Nuclon) with no substrate pretreatment. Cells were incubated under the same conditions as outlined in Example 4.

After 8–10 DIV the number of neurospheres was counted and the results tabulated. As cells grown in a combination of EGF and FGF produced significantly more neurospheres than cells grown in the presence of EGF alone. The combination of EGF and BMP-2 inhibited neurosphere development.

EXAMPLE 39

Comparison of Receptor and Growth Factor Expression in Undifferentiated vs. Differentiated Stem Cell-Derived Progeny by Reverse Transcription-Polymerase Chain Reaction (RT-PCR)

Neurospheres were generated as described in Example 4, and some were differentiated as per Paradigm 1, Example 7. RNA from either undifferentiated or differentiated neurospheres was isolated according to the guanidinium thiocyanate acid phenol procedure of Chomzynski and Sacchi - *Anal. Biochem.* 162: 156–159 1987)]. Complementary DNA (cDNA) was synthesized from total RNA using reverse transcriptase primed with oligo dT. Gene-specific primers were designed and synthesized and these primers were used in PCR to amplify cDNAs for different growth factors and growth factor receptors. Amplified material was run on agarose gels alongside molecular weight markers to ensure that PCR products were of the expected size, while the identity of PCR fragments was confirmed by restriction enzyme analysis and by sequencing [Arcellana-Panlilio, *Methods Enzymol.* 225: 303–328 (1993)]. An ethidium-stained agarose gel visualized via UV transillumination showed the detection of three growth factor receptor transcripts, namely EGF-R, FGF-R, and LIF-R, in undifferentiated and differentiated stem cell-derived progeny. Table I lists the primer sets analyzed and the results of undifferentiated and differentiated cells.

TABLE I

Primer Sets Analyzed

| | Undifferentiated Cells | Differentiated Cells |
|---|---|---|
| Actin | + | + |
| NGF | + | nd |
| EGFr$^m$ | + | + |
| bFGFr | + | + |
| LIFr$^m$ | + | + |
| tyrosine hydroxylase | + | + |
| choline acetyltransferase$^m$ | nd | + |
| cholecystokinin$^m$ | nd | — |
| enkephalin$^m$ | nd | + |
| tyrosine kinase-rA | + | + |
| tyrosine kinase-rB | + | + + + + + |
| tyrosine kinase-rC | + | + | r = receptor
$^m$ = derived from mouse
nd = no data available

EXAMPLE 40

Isolation of Novel Markers and Regulatory Factors Involved in Neural Stem Cell Proliferation and Differentiation Neurospheres are generated as described in Example 4 using CNS tissue from CD$_1$ albino mice (Charles River). Some of these neurospheres are allowed to differentiate according to the rapid differentiation paradigm of Example 7 producing cultures enriched in neurons, astrocytes, and oligodendrocytes. Total RNA is extracted from the undifferentiated neurospheres as well as the differentiated cell cultures using the guanidinium thiocyanate acid phenol method referred to in Example 39. Messenger RNA (mRNA) is isolated by exploiting the affinity of its poly A tract to stretches of either U's or T's. Reverse transcription of the mRNA produced cDNA, is then used to make primary libraries in either plasmid [Rothstein et al., *Methods in Enzymology* 225:587–610 (1993)] or lambda phage vectors. To isolate cDNAs that are specific to either undifferentiated or differentiated stem cell derived progeny, cDNA from one is hybridized to RNA from the other, and vice versa. The unhybridized, and thus culture type-specific, cDNAs in each case are then used to construct subtracted libraries [Lopez-Fernandez and del Mazo, *Biotechniques* 15(4):654–658 (1993)], or used to screen the primary libraries.

Stem cell-derived undifferentiated cell specific and differentiated cell specific cDNA libraries provide a source of clones for novel markers and regulatory factors involved in CNS stem cell proliferation and differentiation. Specific cDNAs are studied by sequencing analysis to detect specific sequence motifs as clues to identity or function, and database searching for homologies to known transcripts. Using cDNAs in a hybridization to various RNA samples electrophoresed on an agarose-formaldehyde gel and transferred to a nylon membrane, allows the estimation of size, relative abundance, and specificity of transcripts. All or portions of cDNA sequences are used to screen other libraries in order to obtain either complete mRNA sequences or genomic sequence information. Antibodies directed against fusion proteins generated from specific cDNAs are used to detect proteins specific to a particular cell population, either by immunocytochemistry or by Western Blot analysis. Specific gene sequences are used to isolate proteins that interact with putative regulatory elements that control gene expression. These regulatory elements are then used to drive the expression of an exogenous gene, such as beta-galactosidase.

EXAMPLE 41

Electrophysiological Analysis of Neurons Generated from Growth Factor-Responsive Stem Cells and Exposed to a Biological Agent Neurospheres were generated as described in Example 4. Neurospheres were dissociated using the technique described in paradigm 2, Example 7. The clonally derived cells were plated at low density and differentiated in the presence of bFGF.

The electrophysiological properties of cells with the morphological appearance of neurons were determined as described as described by Vescovi et al. [*Neuron*, 11: 951–966 (1993)]. Under whole cell current clamp, the mean resting potential and input resistance were −62±9 mV and 372±MΩ. Rectangular suprathreshold current steps, (~100 pA) elicited regenerative potential responses in which the amplitude and time course were stimulus dependent. After the completion of electrophysiological experiments, the cell morphology was visualized by intracellular excitation of 5-carboxyfluorescein.

EXAMPLE 42

Screening for the Effects of Drugs or Other Biological Agents on Growth Factor-Responsive Stem Cell Progeny Generated from Tissue Obtained from a Patient with a Neurological Disorder The effects of BDNF on the EGF-responsive stem cell progeny generated from CNS tissue obtained at biopsy from a patient with Huntington's disease is determined using the methods outlined in Example 7, A to E. BDNF is a potent differentiation factor for GABAergic neurons and promotes extensive neuronal outgrowth. Huntington's Disease is characterized by the loss of GABAergic neurons (amongst others) from the striatum.

EXAMPLE 43

Assay of Striatum-Derived Neurosphere Proliferation in Response to Various Combinations of Proliferative and Regulatory Factors Paradigm 1: Primary striatal cells prepared as outlined in Example 1 were suspended in Complete Medium, without growth factors, plated in 96 well plates (Nunclon) and incubated as described in Example 4. Following a one hour incubation period, a specific proliferative factor, or a combination of proliferative factors including EGF, or bFGF (recombinant human bFGF: R & D Systems), or a combination of EGF and bFGF, or EGF plus FGF plus heparan sulfate (Sigma), or bFGF plus heparan sulfate made up in Complete Medium at a concentration of 20 ng/ml for each of the growth factors and 2 µg/ml for heparan sulfate), was added to each well of the plate.

Activin, BMP-2, TGF-β, IL-2, IL-6, IL-8, MIP-1∂, MIP-1β, MIP-2 (all obtained from Chiron Corp.), TNFα, NGF (Sigma), PDGF (R&D Systems), EGF and CNTF (R. Dunn and P. Richardson, McGill University) were made up in separate flasks of compete medium to a final concentration of 0.2 µg/ml. Retinoic acid (Sigma) was added at a concentration of $10^{-6}$ M. 10 µl of one of these regulatory factor-containing solutions was added to each proliferative factor-containing well of the 96 well plates. Control wells, containing only proliferative factors, were also prepared.

In another set of experiments, the neurosphere inducing properties of each of these regulatory factors was tested by growing cells in their presence, in proliferative factor-free Complete Medium. None of these regulatory factors, with the exception of EGF, when used in the absence of a proliferation-inducing factor such as EGF or FGF, has an effect on neural stem cell proliferation.

The activin, BMP-2, TGF-β, IL-2, IL-6, IL-8, MIP-1∂, MIP-1β, MIP-2, TNFα and EGF additions were repeated every second day, CNTF which was added each day and retinoic acid, NGF and PDGF were added only once, at the beginning of the experiment. The cells were incubated for a period of 10–12 days. The number of neurospheres in each well was counted and the resulting counts tabulated using Cricket Graph III. Other relevant information regarding sphere size and shape were also noted.

In general, bFGF had a greater proliferative effect than EGF on the numbers of neurospheres generated per well. In the presence of 20 ng/ml EGF, approximately 29 neurospheres per well were generated. In the presence of bFGF, approximately 70 neurospheres were generated. However, in bFGF alone, the neurospheres were only about 20% of the size of those generated in the presence of EGF. The combination of EGF and bFGF produces significantly more neurospheres than does EGF alone, but fewer than seen with bFGF alone. The neurospheres are larger than those seen in bFGF alone, approximating those seen in EGF. In the case of bFGF generated spheres, the addition of heparan sulfate increased the size of the spheres to about 70% of the size of those which occur in response to EGF. These data suggest that EGF and FGF have different actions with respect to the induction of stem cell mitogenesis.

The effects of the regulatory factors added to the proliferative factor-containing wells are summarized in Table II. In general, the TGFβ family, interleukins, macrophage-inhibitory proteins, PDGF, TNFα, retinoic acid ($10^{-6}$M) and CNTF significantly reduced the numbers of neurospheres generated in all of the proliferative factors or combinations of proliferative factors tested. BMP-2 (at a dose of 10 ng/ml), completely abolished neurosphere proliferation in response to EGF. EGF and heparan sulfate both greatly increased the size of the neurospheres formed in response to bFGF (about 400%).

TABLE II

Paradigm 2: Antisense/sense experiments: Embryonic tissue was prepared as outlined in Example 1 and plated into 96 well plates in Complete Medium.

| | PROLIFERATIVE FACTORS | | | | | | | | | |
|---|---|---|---|---|---|---|---|---|---|---|
| | EGF | | bFGF | | EGF + bFGF | | bFGF + Heparan | | EGF + bFGF + Heparan | |
| REGULATORY FACTORS | # | size | # | size | # | size | # | size | # | size |
| TGFβ Family ◆ | −57% | − | −57% | − | −34% | −− | −55% | − | −20% | − |
| BMP-2 | −100% | n/a | −5% | = | +16% | −− | −3% | − | +10% | −− |
| Interleukins | −21% | = | −23% | = | −37% | − | −28% | = | −39% | = |
| MIP Family | −25% | = | −6% | = | −32% | − | −22% | = | −33% | − |
| NGF | −10% | = | 0% | = | −30% | = | +5% | = | −48% | = |
| PDGF | −1.5% | = | −4% | = | −26% | = | −10% | = | −27% | = |
| TNFα | −17% | = | −17% | = | −41% | = | −21% | = | −37% | = |
| $10^{-6}$M Retinoic Acid | −8% | −− | −61% | − | −31% | −− | −65% | −− | −45% | −− |
| CNTF | −23% | − | −77% | ~ | −81% | −− | −81% | − | −84% | −− |
| EGF | — | | −14% | ++ | — | | −17% | = | — | |
| Heparan Sulfate | 0% | = | 0% | ++ | 0% | = | | | | |

◆Excluding BMP-2 (i.e. TGFα and activin)
Numbers of neurospheres generated (#) are given as percentages that reflect the decrease (−) or increase (+) in numbers of neurospheres per well, in response to a PROLIFERATIVE FACTOR in the presence of a REGULATORY FACTOR, compared with the number of neurospheres proliferated in the absence of the REGULATORY FACTOR.
Size of neurospheres generated in the presence of PROLIFERATIVE FACTORS and REGULATORY FACTORS compared to those generated in the presence of PROLIFERATIVE FACTORS alone are indicated as follows:
++: much larger; +: larger; =: approximately the same size; ~: variable in size; −: smaller; −−: much smaller Antisense and sense experiments were carried out using the following oligodeoxynucleotides (all sequences written 5' to 3'):

```
EGF receptor:

Sense strand:       GAGATGCGACCCTCAGGGAC    (SEQ ID NO:1)

Antisense           GTCCCTGAGGGTCGCATCTC    (SEQ ID NO:2)
strand:

EGF:

Sense strand:       TAAATAAAAGATGCCCTGG     (SEQ ID NO:3)

Antisense           CCAGGGCATCTTTTATTTA     (SEQ ID NO:4)
strand:
```

Each oligodeoxynucleotide was brought up and diluted in ddH$_2$O and kept at −20° C. Each well of the 96 well plates received 10 µl of oligodeoxynucleotide to give a final concentration of either 1, 2, 3, 4, 5, 10 or 25 µM. Oligodeoxynucleotides were added every 24 hours. The EGF receptor (EGFr) and EGF oligodeoxynucleotides were applied to cultures grown in bFGF (20 ng/ml), and EGFr oligodeoxynucleotides were applied to cultures grown in EGF (20 ng/ml). Cells were incubated at 37° C., in a 5% CO$_2$ 100% humidity incubator. After a period of 10 to 12 days, the number of neurospheres per well was counted and tabulated. A concentration of 3 µM of antisense oligodeoxynucleotides produced a 50% reduction in the number of neurospheres generated per well, whereas the sense oligodeoxynucleotides had no effect on the number of neurospheres generated in response to EGF and FGF. Both the sense and antisense oligodeoxynucleotides were toxic to cells when 10 µM or higher concentrations were used.

Similar experiments can be performed using the following oligonucleotides:

```
FGF receptor:

Sense strand:       GAACTGGGATGTGGGGCTGG    (SEQ ID NO:5)

Antisense           CCAGCCCCACATCCCAGTTC    (SEQ ID NO:6)
strand:

FGF:

Sense strand:       GCCAGCGGCATCACCTCG      (SEQ ID NO:7)

Antisense           CGAGGTGATGCCGCTGGC      (SEQ ID NO:8)
strand:
```

The FGF receptor (FGFr) and FGF oligodeoxynucleotides are applied to cultures grown in EGF, and FGFr oligodeoxynucleotides are applied to cultures grown in bFGF.

Paradigm 3: Embryonic tissue is prepared as outlined in Example 1 and plated into 96 well plates. Complete Medium, containing 20 ng/ml of either EGF of bFGF is added to each well. 10 µl of diluted phorbol 12-myristate 13 acetate (PMA) is added once, at the beginning of the experiment, to each well of the 96 well plates, using an Eppendorf repeat pipetter with a 500 µl tip to give a final concentration of either 10, 20, 40, 100 or 200 µg/ml. Cells are incubated at 37° C. in a 5% CO$_2$ 100% humidity incubator. After a period of 10 to 12 days the number of neurospheres per well is counted and tabulated.

Paradigm 4: Embryonic tissue is prepared as outlined in Example 1 and plated into 96 well plates. 10 µl of diluted staurosporine is added to each well of a 96 well plate, using an Eppendorf repeat pipetter with a 500 µl tip to give a final concentration of either 10, 1, 0.1, or 0.001 µM of staurosporine. Cells are incubated at 37° C., in a 5% CO$_2$ 100% humidity incubator. After a period of 10 to 12 days, the number of neurospheres per well is counted and tabulated.

EXAMPLE 44

Adult Spinal Cord Stem Cell Proliferation—In Vitro Responses to Specific Biological Factors or Combinations of Factors Spinal cord tissue was removed from 6 week to 6 month old mice, as follows: cervical tissue was removed from the vertebral column region rostral to the first rib; thoracic spinal tissue was obtained from the region caudal to the first rib and approximately 5 mm rostral to the last rib; lumbar-sacral tissue constituted the remainder of the spinal cord. The dissected tissue was washed in regular artificial cerebrospinal fluid (aCSF), chopped into small pieces and then placed into a spinner flask containing oxygenated aCSF with high Mg$^{2+}$ and low Ca$^{2+}$ and a trypsin/hyaluronidase and kynurenic acid enzyme mix to facilitate dissociation of the tissue. The tissue was oxygenated, stirred and heated at 30° C. for 1½ hours, then transferred to a vial for treatment with a trypsin inhibitor in media solution (DMEM/12/hormone mix). The tissue was triturated 25–50 times with a fire narrow polished pipette. The dissociated cells were centrifuged at 400 r.p.m. for 5 minutes and then resuspended in fresh media solution. Cells were plated in 35 mm dishes (Costar) and allowed to settle. Most of the media was aspirated and fresh media was added. EGF alone, or EGF and bFGF were added to some of the dishes to give a final concentration of 20 ng/ml each, and bFGF (20 ng/ml) was added, together with 2 µg/ml of heparan sulfate, to the remainder of the dishes. The cells were incubated in 5% CO$_2$, 100% humidity, at 37° C. for $10^{-14}$ days. The numbers of neurospheres generated per well were counted and the results tabulated. EGF alone resulted in the generation of no neurospheres from any of the spinal cord regions. In the presence of EGF plus bFGF, neurospheres were generated from all regions of the spinal cord, in particular the lumbar sacral region. The combinations of EGF+FGF and FGF+heparan sulfate produced similar numbers of spheres in the cervical region, whereas the combination of bFGF plus heparan sulfate resulted in fewer neurospheres from the thoracic and lumbar regions.

EXAMPLE 45

Transplantation of Multipotent Neural Stem Cell Progeny in Animal Models

I. Transplantation Procedure

1. Neurosphere Preparation

Neural tissue was obtained from normal embryonic or adult CD1 mice and from embryonic or adult Rosa 26 mice (transgenic animals derived from C57/BL/6 mice, which express the β-galactosidase gene in all cells, thus allowing the transplanted cells to be easily detected in host tissue). Neurospheres were generated using the procedures described in Examples 1–5, passaged 2 to 8 times (see Example 6), and maintained in culture for 6–10 days after the last passage.

2. Labeling and Preparation of Neural Stem Cell Progeny 16 hours prior to transplantation, neurospheres derived from embryonic and adult tissue were labeled with BrdU by adding BrdU to the media for a total concentration of 1 μM and/or with fluorescent latex beads (Polysciences; 1:100 dilution of 0.75 μm beads). Neurospheres were detached from the substrate by gentle shaking, poured into 50 ml centrifuge tubes and spun down (5 minutes, 400 r.p.m., 15° C., no brake) to remove the proliferation-inducing media used for the proliferation culture. The neurospheres derived from embryonic tissue were then washed twice in Hank's buffered salt solution (HBSS), resuspended in 2 ml HBSS and dissociated by trituration (spheres drawn into a fire-polished pasteur pipette 40x). The neurospheres derived from adult tissue were trypsinized (0.05% in EDTA media; 5–10 min) and then a trypsin inhibitor (ovomucoid; 0.7–1.0 mg/ml in media) was added. The tubes were swirled and the neurospheres were recentrifuged (400 r.p.m., 15° C., no brake). Cells were resuspended in 2 ml media (DMEM F12/hormone mix) and dissociated by mechanical trituration (25×).

Live and dead cells obtained from neurospheres derived from embryonic and adult tissue were counted prior to being centrifuged to remove dead cells (10 min., 400 r.p.m., 15° C., no brake). The live cells were resuspended to appropriate cell density ($1$–$50 \times 10^6$ cells/ml). The cells were recounted to determine the number of live and dead cells and cell viability was calculated. The cells were then transferred to a microcentrifuge tube for storage on ice prior to transplantation. When ready for use, cells were resuspended prior to each cell injection by drawing cells into an eppendorf pipette tip (200 or 1000 μl).

3. Transplantation of Neural Stem Cell Progeny

The donor neural stem cell progeny were transplanted into selected sites in the brain of normal, healthy neonate or adult CD1 or C57BL/6 mice or adult Wistar or Sprague-Dawley rats. In some cases, embryonic cells from CD1 mice received in vitro gene transfer procedures prior to transplantation of the cells. The host animals were anaesthetized with sodium pentobarbital (65 mg/Kg) and placed into a stereotaxic apparatus. A skin incision was made to expose the surface of the skull or vertebrae. Injection sites were located using stereotaxic coordinates to locate the desired site. Burr holes were drilled in the skull and vertebrae at the coordinate sites. A 5 μl syringe was housed on a syringe pump and attached to a stainless steel cannula (30–31 gauge) via a short length of polyethylene tubing. A small air bubble and then 4–5 μl of the desired cell suspension was drawn into the cannula. The cannula was lowered to the desired location and 1–3 μl of the cell suspension was injected at a speed of 0.1–0.5 μl/min. Animals that received xenografts or allograft were treated with 0.1 mg/ml cyclosporin A in the drinking water to reduce the risk of tissue rejection.

4. Analysis of Transplanted Neural Stem Cell Progeny

The animals were allowed to survive for 2–12 weeks prior to sacrifice. At a specified time after transplantation, animals were perfused transcardially for aldehyde fixation of the brain and spinal cord tissue. A low-high pH perfusion protocol was used (Sloviter & Nilayer, (1987) *Brain Res.* Vol. 330:358–363). After perfusion, brains and spinal cords were removed, post-fixed, and then cryoprotected in sucrose/PBS for cutting in a cryostat. Sections of tissue (10 μM) were cut and mounted on microscope slides directly in a sequential way so that adjacent sections could be examined with different anatomical protocols.

Survival of transplanted cells labeled with fluorescent beads were identified by the localization of fluorescent beads within the cell cytoplasm. BrdU labeled cells (cells that had incorporated BrdU into their DNA during cell division in culture prior to transplantation) were identified using antibodies against BrdU (1:250–500; Monoclonal-Sera-lab; Polyclonal-Accurate Chem. & Sci). Antibodies against GFAP (1:250 Monoclona-Boehringer, Polyclonal-BTI), or NeuN (1:250–500; Monoclonal-R. J. Mullen) were then used to identify the differentiation of the transplanted cells. Cell transplants derived from transgenic animals expressing β-galactosidase were histochemically analyzed using methodology described by Turner and Cepko (1987) (*Nature* 328:131–136) and by immunohistochemical staining. For Rosa 26 cells, antibodies against β-galactosidase were used to identify the transplanted cells and antibodies to NeuN were used to identify cells that had differentiated into neurons. Human cells were identified with HLA antibodies (1:250, Monoclonal-Sera-labs). Antibodies were incubated with the tissue samples and detected using standard immunohistochemical protocols.

The results obtained from the animal models described below are summarized in Tables II–V.

A. Model of Huntington's Disease

Rats were anesthetized with nembutal (25 mg/kg i.p) and injected with atropine sulfate (2 mg/kg i.p.). Animals sustained an ibotenate lesion of the striatum, stimulating Huntington's Disease in the animals. 7 days after the lesion, the animals received an injection of cells prepared as in Examples 1–5 under stereotaxic control. Injections were made to the lesioned area via a 21-gauge cannula fitted with a teflon catheter to a microinjector. Injected cells were labelled with fluorescein-labelled microspheres. Animals were given behavioral tests before the lesion, after the lesion, and at various intervals after the transplant to determine the functionality of the grafted cells at various postoperative time points, then killed and perfused transcardially with 4% buffered paraformaldehyde, 0.1% glutaraldehyde and 5% sucrose solution at 4 C. The brains were frozen in liquid nitrogen and stored at −20° C. until use. Brains sections were sliced to 26 μm on a cryostat, fixed in 4% paraformaldehyde and stained using the M6 monoclonal antibody to stain for mouse neurons, and then reacted with a secondary anti-rat fluorescein-conjugated antibody. Neuronal and glial phenotype was identified by dual labeling of the cells with antibody to NSE and GFAP.

B. Parkinson's Disease

Two animal models of Parkinson's Disease were used. In the first model, unilateral dopamine neurons of the *substantia nigra* were lesioned by the stereotaxic administration of 6-OHDA into the *substantia nigra* in adult CD 1 (1–4 μg) and C57BL/6 mice (1 μg), and Wistar rats (16 μg). Mice were pretreated with desipramine (25 mg/Kg i.p.) and rats were pretreated with pargyline (50 mg/Kg i.p.) both of which prevent the action of 6-OHDA on noradrenergic neurons and allow the selective destruction of dopaminergic neurons. In one series of experiments, multipotent neural stem cell progeny obtained from embryonic Rosa 26 mice, were prepared using the procedures described in Examples 1 and 4. The neural stem cell progeny were labeled, prepared, and transplanted into the striatum of the lesioned C57BL/6 mice using the methods described above in this Example.

In a second series of experiments, the cells were administered to the same regions in the brains of adult 6-OHDA Wister rats. In a third series of experiments, proliferated fetal human cells (prepared as outlined in Example 9), were transplanted into the striatum of the 6OOHDA lesioned CD1 mice. After a survival period of 2 weeks, the host animals were sacrificed and their brains removed. The brain tissue was treated and analyzed as described above.

The second animal model used was the adult mutant Weaver mice (Jackson Labs, 3½ months), in which approximately 70% of the dopaminergic neurons of the substantia nigra are lost by the age of 3 months. Animals were anaesthetized and the proliferated progeny of multipotent neural stem cells derived from embryonic Rosa 26 mice were injected into the striatal region of the animals according to the methods described above. The animals were allowed to survive for 15 days prior to sacrifice and analysis of striatal tissue.

C. Cardiac Arrest

Transient forebrain ischemia was induced in adult Wistar rats by combining bilateral carotid occlusion with hypovolemic hypotension (Smith et al. (1984) *Acta Neurol Scand* 69:385–401). These procedures lesion the CA1 hippocampal pyramidal cells which is typical of damage observed in humans following cardiac arrest and the cause of severe memory and cognitive deficits. The progeny of proliferated multipotent neural stem cells, derived from embryonic Rosa 26 mice, were prepared as described above and transplanted into the striatal region of the ischemia lesioned rats. After 8 days, the animals were sacrificed and their brains were removed and analyzed. β-gal positive cells, indicating surviving cells from the Rosa 26 donor) were detected in the lesioned hippocampal region. In addition, double labeled β-gal/NeuN⁺ cells were found indicating that transplanted cells had differentiated into neurons.

D. Stroke

Occlusion of the carotid arteries precipitates the occurrence of ischemic damage similar to that which occurs during stroke. Adult Wistar rats, in which the middle cerebral artery has been occluded to produce symptomatic lesions in the caudal striatum and parietal cortex, have neural stem cell progeny implanted into the lesioned areas. After a survival period, the animals are tested for behavioral improvements and are then sacrificed and their brains analyzed.

E. Epilepsy

Implantation of an electrode into the amygdala is used to kindle the brain, inducing epileptic episodes and other symptoms of epilepsy. Neural stem cell progeny are transplanted into the hippocampal region. The animals are later tested for epileptic episodes and then sacrificed for analysis of the grafted tissue.

F. Alzheimer's Disease

Cognitive impairment is induced in rats and mice by ibotenic acid lesions of the nucleus basalis, or old animals, exhibiting signs of dementia, are used. Neural stem cell progeny are transplanted into the frontal cortex, medial septal nucleus and the nucleus of the diagonal band of the brains of the animals. After a survival period, the animals are tested for cognitive ability and are then sacrificed to allow analysis of brain tissue.

G. Spinal Cord Injury and Disease

Spasticity is a debilitating motor disorder that is a common consequence of disorders such as spinal cord injury, MS, and cerebral palsy. Transection of the spinal cord is used to produce muscular paralysis and is followed by the development of spasticity, which is characterized by debilitating hyperactive tendon reflexes, clonus and muscle spasms. Neural stem cell progeny are prepared and are transplanted into the lumbar lateral funiculus. After a survival period, the animals are examined for improvement in motor control and are then sacrificed to allow for analysis of spinal tissue.

TABLE III

| DONOR CELL SOURCE | HOST | TRANSPLANT REGION | BrdU | BrdU/ GFAP | BrdU/ NeuN |
|---|---|---|---|---|---|
| Embryonic CD1 Mouse | Neonate CD1 Mouse | striatum | + | + | + |
|  | | frontal cortex | + | + | + |
|  | Adult CD1 Mouse | striatum | + | + | + |
|  |  | hippocampus | + | + | + |
|  |  | frontal cortex | + | + | + |
|  |  | parietal cortex | + | + | + |
|  |  | MS/NDB | + | + | + |
|  | Adult Wistar Rat | spinal cord | + | + | + |
|  |  | hippocampus | + | + | + |
|  |  | parietal cortex | + | + |  |
| Adult CD1 Mouse | Adult CD1 Mouse | striatum | + | + |  |
|  |  | hippocampus | + |  |  |
|  |  | frontal cortex | + |  |  |
|  | Adult Wistar Rat | spinal cord | + |  |  |

TABLE IV

| Donor Cell Source | HOST | Transplant Region | β-Gal | BrdU | BrdU/ GFAP |
|---|---|---|---|---|---|
| Embryonic CD1 Mouse in vitro gene transfer | Adult CD1 Mouse | hippocampus | + | + | + |
|  |  | frontal cortex | + | + | + |
|  |  | parietal cortex | + | + | + |
|  |  | striatum | + | + | + |
|  |  | MS/NDB | + | + | + |
| Embryonic Rosa | Adult DC1 Mouse | striatum | + | + | + |
|  |  | parietal cortex | + | + | + |
|  |  | MS/NDB | + | + | + |
| Adult Rosa 26 | Adult C57/BL/6 Mouse | hippocampus | + |  |  |
|  |  | frontal cortex | + |  |  |
|  |  | MS/NDB | + |  |  |

TABLE V

| DONOR CELL SOURCE | HOST | β-Gal | BrdU/ GFAP |
|---|---|---|---|
| Embryonic Rosa 26 Mouse | Adult 6-OHDA lesioned C57BL/6 mouse (striatal injections) | + | + |
|  | Adult 6-OHDA lesioned Wistar rat (striatal injections) | + | + |
|  | Adult Mutant Weaver Mouse (striatal injections) | + | + |

All references, patents, and patent applications cited herein are incorporated herein by reference.

What is claimed is:

1. A method for producing myelin forming cells, comprising:
   (a) culturing a population of multipotent self-renewing central nervous system (CNS) neural stem cells in a culture medium containing one or more predetermined growth factors that induce multipotent CNS neural stem cell proliferation, wherein:
      (i) the cells of the population are derived from primary CNS neural tissue by growth in culture medium containing one or more predetermined growth factors effective for inducing multipotent CNS neural stem cell proliferation without requiring oncogenic immortalization of the CNS neural stem cell,
      (ii) the population comprises cells which stain positive for nestin, and
      (iii) in the presence of differentiation-inducing conditions, the cells of the population produce progeny cells that differentiate into neurons, astrocytes, and oligodendrocytes; and
   (b) causing a cell from the multipotent CNS neural stem cell population to come into contact with a demyelinated neuron, wherein the contact induces the cell to differentiate to a myelin-forming cell.

2. The method of claim 1, wherein the predetermined growth factor is selected from the group consisting of acidic fibroblast growth factor, basic fibroblast growth factor, epidermal growth factor, amphiregulin, transforming growth factor alpha, and combinations thereof.

3. The method of claim 1, wherein prior to causing the cell from the multipotent CNS neural stem cell population to come into contact with the demyelinated neuron, the cell is caused to differentiate into differentiated neural cells comprising oligodendrocytes.

4. The method of claim 1, wherein the growth factor in the culture medium is fibroblast growth factor.

5. The method of claim 4, wherein the culture medium additionally comprises epidermal growth factor.

6. The method of claim 3, wherein the differentiated neural cells additionally comprise type I astrocytes.

7. The method of claims 1 or 3, wherein in the presence of exogenously administered platelet-derived growth factor, the myelin-producing cell is capable of forming patches of myelin.

8. The method of claim 1, wherein the demyelinated neuron is located within a host.

9. The method of claim 8, wherein the multipotent CNS neural stem cell is obtained from the host.

10. The method of claim 1, wherein the culture medium is a defined culture medium.

11. The method of claim 3, wherein the cells of the multipotent CNS neural stem cell population are caused to differentiate in a culture medium that contains serum.

12. The method of claim 1, wherein the multipotent CNS neural stem cell is obtained from a primate.

13. The method of claim 12, wherein the primate is a human.

14. The method of claim 1, wherein the multipotent CNS neural stem cell is obtained from a juvenile or adult.

15. A method of using one or more cells from a multipotent self-renewing central nervous system neural stem (CNS) cell population to form patches of myelin, comprising:
   causing one or more cells from a multipotent self-renewing CNS neural stem cell population to come into contact with a demyelinated neuron to form patches of myelin, wherein:
   (i) the cells of the population are derived from primary CNS neural tissue by growth in culture medium containing one or more predetermined growth factors effective for inducing multipotent CNS neural stem cell proliferation without requiring oncogenic immortalization of the CNS neural stem cell,
   (ii) the population comprises cells which stain positive for nestin, and
   (iii) under suitable culture conditions, the cells produce progeny cells that differentiate into neurons that express neuron specific enolase or neurofilament and glia that express glial fibrillary acidic protein or galactocerebroside.

16. The method of claim 15, wherein the cells of the multipotent CNS neural stem cell population have been proliferated in a culture medium containing one or more predetermined growth factors selected from the group consisting of acidic fibroblast growth factor, basic fibroblast growth factor, epidermal growth factor, amphiregulin, transforming growth factor alpha, and combinations thereof prior to contacting the neuron.

17. The method of claim 15, wherein prior to causing the cells of the multipotent self-renewing CNS neural stem cell population to come into contact with the demyelinated neuron, the cells are caused to differentiate into differentiated neural cells comprising oligodendrocytes.

18. The method of claim 17, wherein the differentiated neural cells additionally comprise type I astrocytes.

19. The method of claims 15 or 17, wherein patches of myelin are formed in the presence of exogenously administered platelet-derived growth factor.

20. The method of claim 15, wherein the demyelinated neuron is located within a host.

21. The method of claim 20, wherein the multipotent CNS neural stem cell is obtained from the host.

22. The method of claim 15, wherein the culture medium is a defined culture medium.

23. The method of claim 15, wherein the multipotent CNS neural stem cell is obtained from a primate.

24. The method of claim 23, wherein the primate is a human.

25. The method of claim 1, wherein the culture medium is substantially serum-free.

26. The method of claim 1, wherein the cells of the multipotent CNS neural stem cell population includes undifferentiated cells which differentiate into oligodendrocytes in the presence of the demyelinated neuron.

27. The method of claim 15, wherein the multipotent CNS neural stem cell has not been cultured serum-containing medium.

28. The method of claim 15, wherein the cells of the multipotent CNS neural stem cell population include undifferentiated cells which differentiate into oligodendrocytes in the presence of the demyelinated neuron.

29. The method of claim 25, wherein prior to contacting the cells of the multipotent CNS neural stem cell population with the demyelinated neuron, at least one subsequent cell culture is prepared by combining the cells of the multipotent CNS neural stem cell population with fresh culture medium containing one or more predetermined growth factors, to induce further proliferation of the cells of the population.

30. The method of claim 27, wherein prior to contacting the cells of the multipotent CNS neural stem cell population with the demyelinated neuron, at least one subsequent cell culture is prepared by combining the cell of the multipotent CNS neural stem cell population with fresh culture medium containing one or more predetermined growth factors, to induce further proliferation of the cells of the population.

31. The method of claim 1, wherein prior to the causing one or more cell of the multipotent CNS neural stem cell population to come into contact with the neuron, at least one subsequent cell culture is prepared by combining the multipotent self-renewing CNS neural stem cell progeny with fresh culture medium containing one or more growth factors to induce further proliferation of the cells of said population of multipotent CNS neural stem cells.

32. The method of any one of claims 1 or 15, wherein the cells of the multipotent CNS neural stem cell population have been proliferated in a suspension culture prior to contacting the neuron.

33. A cell culture system for forming patches of myelin, comprising:
   (a) one or more multipotent self-renewing central nervous system (CNS) neural stem cells, wherein:
      (i) the cells of the population are derived from primary CNS neural tissue by growth in culture medium containing one or more predetermined growth factors effective for inducing multipotent CNS neural stem cell proliferation without requiring oncogenic immortalization of the CNS neural stem cell,
      (ii) the population comprises cells which stain positive for nestin, and
      (iii) under suitable culture conditions, the cells of the population differentiate into neurons that express neuron specific enolase or neurofilament and glia that express glial fibrillary acidic protein or galactocerebroside; and;
   (b) a culture medium containing one or more predetermined growth factors that induce multipotent CNS neural stem cell proliferation; and
   (c) a demyelinated neuron.

34. The cell culture system of claim 33, wherein the CNS neural stem cells have been proliferated in a culture medium containing one or more predetermined growth factors selected from the group consisting of acidic fibroblast growth factor, basic fibroblast growth factor, epidermal growth factor, amphiregulin, transforming growth factor alpha, and combinations thereof prior to contacting the neuron.

35. The cell culture system of claim 33, wherein the cells of the population have been caused to differentiate to differentiated neural cells comprising oligodendrocytes.

36. The cell culture system of claim 35, wherein the differentiated neural cells additionally comprise type I astrocytes.

37. The system of claim 34 wherein said demyelinated neuron is located within a recipient.

38. The system of claim 34 wherein said mammalian neural tissue is obtained from said recipient.

39. The system of claim 34 wherein said culture medium is defined.

40. The cell culture system of claim 34, wherein the multipotent CNS neural stem cell is a primate cell.

41. The cell culture system of claim 40, wherein the primate is a human.

42. The cell culture system of claim 34, wherein the multipotent CNS neural stem cells are proliferated in a suspension culture.

43. A method of treating a demyelination disease in a mammal, the method comprising administering an effective amount of a multipotent self-renewing central nervous system neural stem cell population to the mammal.

* * * * *